(12) United States Patent
Kovalchuk

(10) Patent No.: US 10,808,258 B2
(45) Date of Patent: Oct. 20, 2020

(54) HIGH THEBAINE POPPY AND METHODS OF PRODUCING THE SAME

(71) Applicant: API LABS INC., Lethbridge, Alberta (CA)

(72) Inventor: Igor Kovalchuk, Lethbridge (CA)

(73) Assignee: API LABS INC., Lethbridge, Alberta (CA)

(*) Notice: Subject to any disclaimer, the term of this patent is extended or adjusted under 35 U.S.C. 154(b) by 0 days.

(21) Appl. No.: 15/762,090

(22) PCT Filed: Aug. 11, 2017

(86) PCT No.: PCT/CA2017/050951
§ 371 (c)(1),
(2) Date: Mar. 21, 2018

(87) PCT Pub. No.: WO2018/027324
PCT Pub. Date: Feb. 15, 2018

(65) Prior Publication Data
US 2019/0169625 A1 Jun. 6, 2019

Related U.S. Application Data

(60) Provisional application No. 62/374,682, filed on Aug. 12, 2016.

(30) Foreign Application Priority Data

Sep. 7, 2016 (CA) ...................................... 2941315

(51) Int. Cl.
*C12N 15/82* (2006.01)
*A01H 6/64* (2018.01)

(52) U.S. Cl.
CPC ..... *C12N 15/8216* (2013.01); *C12N 15/8218* (2013.01); *C12N 15/8243* (2013.01); *C12N 15/8257* (2013.01); *C12Y 114/11031* (2013.01); *C12Y 114/11032* (2013.01)

(58) Field of Classification Search
None
See application file for complete search history.

(56) References Cited

U.S. PATENT DOCUMENTS

| | | |
|---|---|---|
| 6,723,894 B2 | 4/2004 | Fist et al. |
| 6,730,838 B1 | 5/2004 | Sharma et al. |
| 6,790,959 B1 | 9/2004 | Lin et al. |
| 6,864,370 B1 | 3/2005 | Lin et al. |
| 6,930,224 B1 | 8/2005 | Larkin et al. |
| 7,193,127 B1 | 3/2007 | Kutchan et al. |
| 7,312,376 B2 | 12/2007 | Apuya et al. |
| 7,390,642 B2 | 6/2008 | Kutchan et al. |
| 2006/0195934 A1 | 8/2006 | Apuya et al. |
| 2009/0227796 A1 | 9/2009 | Fist |
| 2010/0075385 A1 | 3/2010 | Kutchan et al. |
| 2010/0234600 A1 | 9/2010 | Fist et al. |

FOREIGN PATENT DOCUMENTS

| | | |
|---|---|---|
| EP | 1632565 A1 | 3/2006 |
| WO | 2009/109012 A1 | 9/2009 |
| WO | 2009/143574 A1 | 12/2009 |
| WO | 2011/058446 A3 | 5/2011 |

OTHER PUBLICATIONS

Hagel et al, 2010, Nature Chemical Biology, 6, 273-275.*
Wijekoon et al, 2012, The Plant Journal, 69:1052-1063.*
Milgate et al, 2004, Nature, 431:413-414.*
Facchini et al, 2005, Can. J. Bot., 83:1189-1206.*
Farrow et al., Dioxygenases Catalyze O-Demethylation and O,O-Demethylation with Widespread Roles in Benzylisoquinoline Alkaloid Metabolism in Opium Poppy, The Journal of Biological Chemistry, 2013, pp. 28997-29012, vol. 288, No. 40.
Australian Patent Office, Examination report No. 2 for standard patent application No. AU2017310339, dated Sep. 17, 2018, 7 pages.
Facchini, et al., 2005, "Opium poppy: a model system to investigate alkaloid biosynthesis in plants" *Canadian Journal of Botany*, 83(10):1189-1206.
Park, et al., 2002, "Antisense RNA-Mediated Suppression of Benzophenanthridine Alkaloid Biosynthesis in Transgenic Cell Cultures of California Poppy" *Plant Physiol.* 128(2):696-706.
Facchini, et al., 2003, "Developmental and inducible accumulation of gene transcripts involved in alkaloid biosynthesis in opium poppy" *Phytochem.* 64(1):177-186.
Desgagne-Penix, et al., 2009, "Mutagenesis as a Functional Genomics Platform for Pharmaceutical Alkaloid Biosynthetic Gene Discovery in Opium Poppy" *Plenary Session 22 Conference Paper: Food and Agriculture Organization of the United Nations.* Rome, 411-418.
Millgate, et al., 2004, "Analgesia: Morphine-pathway block in top1 poppies" *Nature* 431:413-414.
Allen, et al., *Nature Biotechnology* 22:1559-1566, 2004.
Kawano, et al., *Pharmaceuticals* 5: 133-154, 2012.
Wijekoon, et al., *Plant Journal* 69: 1052-1063, 2012.
Hagel, et al., Nature Chemical Biology 6: 273-275, 2010.
Allen et al., "Metabolic engineering of morphinan alkaloids by over-expression and RNAi suppression of salutaridinol 7-O-acetyltransferase in opium poppy," Plant Biotechnology Journal, 6, pp. 22-30 (2008).

* cited by examiner

*Primary Examiner* — Jason Deveau Rosen
(74) *Attorney, Agent, or Firm* — Mintz Levin Cohn Ferris Glovsky and Popeo, P.C.

(57) ABSTRACT

This disclosure relates to the production of opium poppy plants having high levels of thebaine. More particularly, the disclosure relates to the production of opium poppies having high levels of thebaine by simultaneously reducing the expression of genes encoding thebaine 6-0-demethylase (T6ODM) and codeine 3-0-demethylase (CODM).

20 Claims, 10 Drawing Sheets
Specification includes a Sequence Listing.

```
                              1                                               50
CODM GQ500141    (1)   ATGGAGACACCAATACTTATCAAGCTAGGCAATGGTTTGTCAATACCAAG
T6ODM GQ500139   (1)   ATGGAGAAAGCAAAACTTATGAAGCTAGGTAATGGTATGGAAATACCAAG
                              51                                              100
CODM GQ500141    (51)  TGTTCAGGAATTGGCTAAACTCACGCTTGCAGAAATTCCATCTCGATACA
T6ODM GQ500139   (51)  TGTTCAAGAATTGGCTAAACTCACGCTTGCCGAAATTCCATCTCGATACG
                              101                                             150
CODM GQ500141    (101) CATGCACCGGTGAAAGCCCGTTGAATAATATTGGTGCGTCTGTAACAGAT
T6ODM GQ500139   (101) TATGCGCCAATGAAAACCTTTGTTGCCTATGGGTGCATCTGTCATAAAT
                              151                                             200
CODM GQ500141    (151) GAT---GAAACAGTTCCTGTCATCGATTTGCAAAATTTACTATCTCCAGA
T6ODM GQ500139   (151) GATCATGAAACCATTCCTGTCATCGATATAGAAAATTTATTATCTCCAGA
                              201                                             250
CODM GQ500141    (198) ACCCGTAGTTGGAAAGTTAGAATTGGATAAGCTTCATTCTGCTTGCAAAG
T6ODM GQ500139   (201) ACCAATAATCGGAAAGTTAGAATTAGATAGGCTTCATTTGCTTGCAAAG
                              251                                             300
CODM GQ500141    (248) AATGGGGTTTCTTTCAGCTGGTTAACCATGGAGTCGACGCTTTACTGATG
T6ODM GQ500139   (251) AATGGGGTTTTTTTCAGGTAGTGAACCATGGAGTCGACGCTTCATTGGTG
                              301                                             350
CODM GQ500141    (298) GACAATATAAAATCAGAAATTAAAGGTTTCTTTAACCTTCCAATGAATGA
T6ODM GQ500139   (301) GATAGTGTAAAATCAGAAATTCAAGGTTTCTTTAACCTTTCTATGGATGA
                              351                                             400
CODM GQ500141    (348) GAAAACTAAATACGGACAGCAAGATGGAGATTTTGAAGGATTTGGACAAC
T6ODM GQ500139   (351) GAAAACTAAATATGAACAGGAAGATGGAGATGTGGAAGGATTTGGACAAG
                              401                                             450
CODM GQ500141    (398) CCTATATTGAATCGGAGGACCAAAGACTTGATTGGACTGAAGTGTTTAGC
T6ODM GQ500139   (401) GCTTTATTGAATCAGAGGACCAAACACTTGATTGGGCAGATATATTTATG
                              451                                             500
CODM GQ500141    (448) ATGTTAAGTCTTCCTCTCCATTTAAGGAAGCCTCATTTGTTTCCAGAACT
T6ODM GQ500139   (451) ATGTTCACTCTTCCACTCCATTTAAGGAAGCCTCACTTATTTTCAAAACT
                              501                                             550
CODM GQ500141    (498) CCCTCTGCCTTTCAGGGAGACACTGGAATCCTACCTATCAAAAATGAAAA
T6ODM GQ500139   (501) CCCAGTGCCTCTCAGGGAGACAATCGAATCCTACTCATCAGAAATGAAAA
                              551                                             600
```

FIG. 3

| | | |
|---|---|---|
| CODM GQ500141 | (548) | AACTATCAACGGTTGTCTTTGAGATGTTGGAAAAATCTCTACAATTA--- |
| T6ODM GQ500139 | (551) | AGTTATCCATGGTTCTCTTTAATAAGATGGAAAAAGCTCTACAAGTACAA |
| | | 601                                            650 |
| CODM GQ500141 | (595) | ---GTTGAGATTAAAGGTATGACAGACTTATTTGAAGATGGGTTGCAAAC |
| T6ODM GQ500139 | (601) | GCAGCCGAGATTAAGGGTATGTCAGAGGTGTTTATAGATGGGACACAAGC |
| | | 651                                            700 |
| CODM GQ500141 | (642) | AATGAGGATGAACTATTATCCCCTTGTCCTCACCAAACTGGATGG |
| T6ODM GQ500139 | (651) | AATGAGGATGAACTATTATCCCCTTGTCCTCACCAAACTGGATGG |
| | | 701                                            750 |
| CODM GQ500141 | (692) | GTCTTACGTCACACTCGGATTTTAGCGGTTTGACAATCCTCCTTCAATT |
| T6ODM GQ500139 | (701) | GTCTTACGTCCACTCGGATTTTGCGGTTTGACAATCCTCCTTCAAATC |
| | | 751                                            800 |
| CODM GQ500141 | (742) | AAAGAAGTAGAAGGATTACAAATAAAAAGAAGAGAATGGATTTCAAT |
| T6ODM GQ500139 | (751) | AACGAAGTAGAAGGATTACAAATAAAAAGAGAGAATGGATTTCAAT |
| | | 801                                            850 |
| CODM GQ500141 | (792) | CAAACCTCTACCTAATGCGTTCATAGTGAATGTTGGAGAAATTTTGGAGA |
| T6ODM GQ500139 | (801) | CAAACCTCTACCTAATGCGTTCTAGTGAATGTTGGAGAAATTTTGGAGA |
| | | 851                                            900 |
| CODM GQ500141 | (842) | TAATGACTAATGGAATTTACCATAGAGTCGAACACCGGGCAGTAGTAAAC |
| T6ODM GQ500139 | (851) | TAATGACTAATGGAATTTACCATAGAGTCGAACACCGGGCAGTAGTAAAC |
| | | 901                                            950 |
| CODM GQ500141 | (892) | TCAACAAAGGAGAGGCTCTCAATCGCAACATTTCATGACACTAAACTAGA |
| T6ODM GQ500139 | (901) | TCAACAAAGGAGAGGCTCTCAATCGCAACATTTCATGACACTASACTAGA |
| | | 951                                            1000 |
| CODM GQ500141 | (942) | GTCAGAATAGGCCCAATTTCAAGCTTGATAACACCAGAGACACCTGCTT |
| T6ODM GQ500139 | (951) | GTCGGAATAGGCCCAATTCAGCTTGATTACCAGAGACACCTGCTT |
| | | 1001                                           1050 |
| CODM GQ500141 | (992) | TGTTAAAAGAGG---TAGGTATGAGGATATTTTGAAGGAAAATCTTTCA |
| T6ODM GQ500139 | (1001)| TGTTAAAAGAGGCTACATATGGGGATCTTGTGGAGGAATGTAAAACA |
| | | 1051                                           1095 |
| CODM GQ500141 | (1039)| AGGAAGCTTGATGGAAAATCATTTCTCGACTACATGAGGATGTGA |
| T6ODM GQ500139 | (1051)| AGGAAGCTCGATGGAAAATCATTTCTTGACTCCATGAGGATTTGA |

FIG. 3 CONTINUED

HIGH THEBAINE POPPY AND METHODS OF PRODUCING THE SAME

BACKGROUND OF THE DISCLOSURE

1. Field of Disclosure

This disclosure relates to the production of opium poppies having high levels of thebaine. More particularly, the disclosure relates to the production of opium poppies having high levels of thebaine by simultaneously reducing the expression/activity of thebaine 6-O-demethylase (T6ODM) and codeine 3-O-demethylase (CODM).

2. Description of Related Art

Opioids are psychoactive substances derived from the opium poppy (*Papaver somniferum*), or their synthetic analogues. Opioids have the potential to cause substance dependence that is characterized by a strong desire to take opioids, impaired control over opioid use, persistent opioid use despite harmful consequences, a higher priority given to opioid use than to other activities and obligations, increased tolerance, and a physical withdrawal reaction when opioids are discontinued. As of 2014, there were an estimated 17 million people who suffer from opioid dependence (i.e. an addiction to opioids). The majority of people dependent on opioids use illicitly cultivated and manufactured heroin. Due to their pharmacological effects, opioids in high doses can cause respiratory depression and death. As of 2014, an estimated 69 000 people die worldwide from opioid overdose each year.

In the World Drug Report 2016, the United Nations Office on Drugs and Crime indicated that recent declines in opium production would not lead to major shortages in the global heroin market given the high opium production levels of previous years. Thus, it may take a period of sustained decline in opium production for the repercussions to be felt in the heroin market. It would be desirable to have a method of disrupting opium production by turning off poppy plant genes necessary for the production of psychoactive alkaloids in the field.

Hydroxymorphinans, such as oxycodone, naloxone, naltrexone, nalbuphine and nalmefene are important opiate derivatives due to their utility as potent analgesics and/or narcotic antagonists. The most practical synthetic routes to the preparation of these pharmaceuticals use the alkaloid, thebaine, as a starting material. Other important opiate derivatives such as the ring-C bridged compounds buprenorpine and etorphine are also most practically prepared from thebaine.

Unfortunately, thebaine is costly due to its limited availability. Total synthesis is difficult and, in poppy plants, thebaine typically accumulates to low levels of only 0.5 to 2% of the total alkaloids in opium poppy. Referring to FIG. 1, thebaine exists at a branch point of morphine biosynthesis, being the substrate for two competing enzymes. Thebaine 6-O-demethylase (T6ODM) converts thebaine to oripavine, and codeine 3-O-demethylase (CODM) converts thebaine to neopinone.

Mutants of opium poppy accumulating thebaine and oripavine rather than morphine and codeine have been reported, including the TOP1 variety derived through chemical mutagenesis (Millgate et al. 2004). Although the metabolic block in TOP1 was suggested to result from a defect in the enzyme catalyzing the 6-O-demethylation of thebaine and oripavine, the biochemical basis for the phenotype was not determined. Moreover, a microarray was used to identify 10 genes underexpressed in TOP1, which list did not include any enzymes theoretically capable of O-demethylation. A plant line containing the TOP1 mutation was deposited under the Budapest Treaty with the American Type Culture Collection on Mar. 20, 2008, under ATCC Patent Deposit Designation PTA-9110. WO2009/109012 discloses the mutagenesis of the line designated PTA-9110 to produce a further line accumulating high levels of thebaine, which was deposited under the Budapest Treaty with the American Type Culture Collection on Mar. 20, 2008, under ATCC® Patent Deposit Designation PTA-9109. However, the biochemical basis for the phenotype was not explored.

Researchers have been interested in using molecular approaches to engineer opium poppy to produce opioids of choice for several years, however, the results have at times been unexpected and frustrating. For example, Allen et al. (Nature Biotechnology 22:1559-1556) used RNA interference (RNAi) to silence the genes encoding codeinone reductase (COR), the penultimate enzyme of morphine biosynthesis. COR converts codeinone to codeine. However, rather than resulting in the accumulation of codeinone, elimination of COR activity resulted in accumulation of reticuline, i.e. seven enzymatic steps before COR. The surprising accumulation of reticuline suggests a feedback mechanism preventing intermediates from general benzylisoquinoline synthesis entering the morphine-specific branch.

SUMMARY

This disclosure relates to the production of opium poppies having high levels of thebaine. More particularly, the disclosure relates to the production of opium poppies having high levels of thebaine by simultaneously reducing the expression/activity of thebaine 6-O-demethylase (T6ODM) and codeine 3-O-demethylase (CODM).

Various aspects of the disclosure relate to a method of increasing accumulation of thebaine in an opium poppy plant, the method comprising genetically modifying the plant to simultaneously reduce the activity of thebaine 6-O-demethylase (T6ODM) and codeine 3-O-demethylase (CODM) in the poppy plant. The wild type T6ODM may have the amino acid sequence of SEQ ID NO: 1. The wild type CODM may have the amino acid sequence of SEQ ID NO: 3.

In some instances, genetically modifying the plant to simultaneously reduce the activity of T6ODM comprises introducing an expression construct to reduce the accumulation of transcripts from an endogenous gene encoding T6ODM. In some instances, the sequence of the expression construct to reduce the accumulation of transcripts from the endogenous gene encoding T6ODM comprises a portion of SEQ ID NO: 2 or SEQ ID NO: 4 In some instances, genetically modifying the plant to simultaneously reduce the activity of T6ODM comprises introducing a loss of function mutation in an endogenous gene encoding T6ODM.

In some instances, genetically modifying the plant to simultaneously reduce the activity of CODM comprises introducing an expression construct to reduce the accumulation of transcripts from an endogenous gene encoding CODM. In some instances, the sequence of the expression construct to reduce the accumulation of transcripts from the endogenous gene encoding CODM comprises a portion of SEQ ID NO: 2 or SEQ ID NO: 4. In some instances, genetically modifying the plant to simultaneously reduce the activity of CODM comprises introducing a loss of function mutation in an endogenous gene encoding CODM.

Various aspects of the disclosure relate to a method of producing an opium poppy plant with increased levels of thebaine relative to a wild type plant, the method comprising: crossing a first parent having at least one loss of function allele of the gene encoding thebaine 6-O-demethylase with a second parent having at least one loss of function allele of the gene encoding codeine 3-O-demethylase; and allowing progeny that have both the loss of function mutation allele of the gene encoding thebaine 6-O-demethylase and the loss of function allele of the gene encoding codeine 3-O-demethylase to self pollinate to produce a plant that is homozygous for the loss of function mutation allele of the gene encoding thebaine 6-O-demethylase and homozygous for the loss of function allele of the gene encoding codeine 3-O-demethylase.

Various aspects of the disclosure relate to a method for producing an opium poppy plant with increased thebaine content, the method comprising: decreasing the expression an endogenous gene encoding an endogenous thebaine 6-O-demethylase (T6ODM) in the plant; and decreasing the expression of an endogenous gene encoding codeine 3-O-demethylase (CODM) in the plant. In some instances, decreasing the expression of the endogenous gene encoding T6ODM comprises introducing or producing a loss of function allele in the endogenous gene encoding T6ODM. In some instances, decreasing the expression of the endogenous gene encoding CODM comprises introducing or producing a loss of function allele in the endogenous gene encoding CODM.

In some instances, decreasing the expression of the endogenous gene encoding T6ODM comprises expressing a first heterologous nucleic acid molecule homologous to a portion of the endogenous gene encoding T6ODM, wherein the first heterologous nucleic acid molecule decreases expression of the endogenous gene encoding T6ODM. In some instances, decreasing the expression of the endogenous gene encoding CODM comprises introducing or producing a loss of function allele in the endogenous gene encoding CODM. In some instances, decreasing expression of the endogenous gene encoding CODM comprises expressing a second heterologous nucleic acid molecule homologous to a portion of the endogenous gene encoding CODM, wherein the second heterologous nucleic acid molecule decreases expression of the endogenous gene encoding CODM.

In some instances, decreasing expression of the endogenous gene encoding CODM comprises expressing a heterologous nucleic acid molecule homologous to a portion of the endogenous gene encoding CODM, wherein the heterologous nucleic acid molecule decreases expression of the endogenous gene encoding CODM. In some instances, decreasing T6ODM activity comprises introducing or producing a loss of function allele in the endogenous gene encoding T6ODM.

In some instances, the loss of function allele comprises a disruption or point mutation in the gene. The disruption may be a deletion or an insertion. An insertion may be a T-DNA or a transposable element.

In some instances, the first heterologous nucleic acid molecule decreases expression of the endogenous gene encoding T6ODM by RNA interference.

In some instances, the second heterologous nucleic acid molecule decreases expression of the endogenous gene encoding CODM by RNA interference.

In some instances, the heterologous nucleic acid molecule decreases expression of the endogenous gene encoding CODM by RNA interference.

In some instances, the heterologous nucleic acid molecule comprises a portion of SEQ ID NO: 2 or SEQ ID NO: 4. In some instances, the heterologous nucleic acid molecule comprises a portion of SEQ ID NO: 7. In some instances, the heterologous nucleic acid molecule comprises a portion of SEQ ID NO: 8.

In some instances, the T6ODM has an amino acid sequence at least 95% identical to SEQ ID NO: 1 and the CODM has an amino acid sequence at least 95% identical to SEQ ID NO: 3.

Various aspects of the disclosure relate to a method of generating an opium poppy plant having increased thebaine content relative to a wild type opium poppy plan, the method comprising: i) using a molecular methodology to identify a first plant as comprising a loss of function allele in an endogenous gene encoding codeine 3-O-demethylase (CODM); ii) establishing a cross of said first plant to a second plant having a loss of function allele in an endogenous gene encoding thebaine 6-O-demethylase (T6ODM); iii) allowing progeny from the cross to self-fertilize; and iv) screening progeny from self-fertilized plants for a plant that is homozygous for both the loss of function allele in the endogenous gene encoding CODM and the loss of function allele in the endogenous gene encoding T6ODM.

In some instances, the second plant having the loss of function allele in the endogenous gene encoding T6ODM is identified using a molecular methodology. In some instances, the loss of function allele in the endogenous gene encoding T6ODM is generated by genetic modification of the second plant or an ancestor thereof. In some instances, the second plant having the loss of function allele in the endogenous gene encoding T6ODM is a plant of the line deposited as ATCC PTA-9110.

Various aspects of the disclosure relate to a method of generating an opium poppy plant having an thebaine content relative to a wild type opium poppy plant, the method comprising: i) using a molecular methodology to identify a first plant as comprising a loss of function allele in an endogenous gene encoding thebaine 6-O-demethylase (T6ODM); ii) establishing a cross of said first plant to a second plant having a loss of function allele in an endogenous gene encoding codeine 3-O-demethylase (CODM); iii) allowing progeny from the cross to self-fertilize; and iv) screening progeny from self-fertilized plants for a plant that is homozygous for both the loss of function allele in the endogenous gene encoding CODM and the loss of function allele in the endogenous gene encoding T6ODM. In some instances, the second plant having the loss of function allele in the endogenous gene encoding CODM is identified using a molecular methodology. In some instances, the loss of function allele in the endogenous gene encoding CODM is generated by genetic modification of the second plant or an ancestor thereof. In some instances, the second plant having the loss of function allele in the endogenous gene encoding CODM is a plant of the line deposited as ATCC PTA-9109.

Various aspects of the disclosure relate to a method of generating an opium poppy plant having increased thebaine content relative to a wild type opium poppy plant, the method comprising: i) using a molecular methodology to identify a plant as comprising a loss of function allele in an endogenous gene encoding thebaine 6-O-demethylase (T6ODM); ii) genetically modifying the plant to introduce a loss of function allele in an endogenous gene encoding codeine 3-O-demethylase (CODM); iii) allowing the plant to self-fertilize; and iv) screening progeny from the self-fertilized plant for a plant that is homozygous for both the loss of function allele in the endogenous gene encoding CODM and the loss of function allele in the endogenous gene encoding T6ODM.

Various aspects of the disclosure relate to a method of generating an opium poppy plant having increased thebaine content relative to a wild type opium poppy plant, the method comprising: i) using a molecular methodology to identify a plant as comprising a loss of function allele in an endogenous gene encoding codeine 3-O-demethylase (CODM); ii) genetically modifying the plant to introduce a loss of function allele in an endogenous gene encoding thebaine 6-O-demethylase (T6ODM) in the plant by genetic modification; iii) allowing the plant to self-fertilize; and iv) screening progeny from the self-fertilized plant for a plant that is homozygous for both the loss of function allele in the endogenous gene encoding CODM and the loss of function allele in the endogenous gene encoding T6ODM.

Various aspects of the disclosure relate to a method of generating an opium poppy plant having increased thebaine content relative to a wild type opium poppy plant, the method comprising: i) using a molecular methodology to identify a plant as comprising a loss of function allele in an endogenous gene encoding thebaine 6-O-demethylase (T6ODM); ii) genetically modifying the plant to reduce expression of an endogenous gene encoding codeine 3-O-demethylase (CODM); iii) allowing the plant to self-fertilize; and iv) screening progeny from the self-fertilized plant for a plant that is homozygous for the loss of function allele in the endogenous gene encoding T6ODM and has reduced expression of the endogenous gene encoding CODM. In some instances, genetically modifying the plant to reduce expression of the endogenous gene encoding CODM comprises introducing an expression construct to express a hairpin RNA targeting the endogenous gene encoding CODM.

Various aspects of the disclosure relate to a method of generating an opium poppy plant having increased thebaine content relative to a wild type opium poppy plant, the method comprising: i) using a molecular methodology to identify a plant as comprising a loss of function allele in an endogenous gene encoding codeine 3-O-demethylase (CODM); ii) genetically modifying the plant to reduce expression of an endogenous gene encoding thebaine 6-O-demethylase (T6ODM); iii) allowing the plant to self-fertilize; and iv) screening progeny from the self-fertilized plant for a plant that is homozygous for both the loss of function allele in the endogenous gene encoding CODM and has reduced expression of the endogenous gene encoding T6ODM. In some instances, genetically modifying the plant to reduce expression of the endogenous gene encoding T6ODM comprises introducing an expression construct to express a hairpin RNA targeting the endogenous gene encoding T6ODM.

In some instances, the molecular methodology comprises targeting induced local lesions in genomes (TILLING) methodology.

Various aspects of the disclosure relate to an opium poppy plant produced by a method as described above.

Various aspects of the disclosure relate to a genetically modified opium poppy plant or plant cell having reduced activity of thebaine 6-O-demethylase (T6ODM) and codeine 3-O-demethylase (CODM) relative to a wild type plant, wherein the opium poppy plant is genetically modified to have reduced expression of T6ODM, and CODM, or both.

In some instances, the plant comprises a first expression construct for reducing the expression of T6ODM and a second expression construct for reducing expression of CODM. In some instances, the first expression construct comprises a first nucleic acid molecule encoding a first hairpin RNA for reducing expression of an endogenous gene encoding T6ODM. In some instances, the endogenous gene encoding T6ODM encodes an mRNA comprising having the sequence of SEQ ID NO: 15. In some instances, the nucleic acid molecule encoding the first hairpin RNA comprises a portion of SEQ ID NO: 2.

In some instances, the second expression construct comprises a second nucleic acid molecule encoding a second hairpin RNA for reducing expression of an endogenous gene encoding CODM. In some instances, the endogenous gene encoding CODM encodes an mRNA comprising having the sequence of SEQ ID NO: 16. In some instances, the nucleic acid molecule encoding the second hairpin RNA comprises a portion of SEQ ID NO: 4.

In some instances, the plant or plant cell comprises an expression construct comprising a nucleic acid molecule for reducing the expression of T6ODM and CODM. In some instances, the nucleic acid molecule encodes a hairpin RNA for reducing expression of an endogenous gene encoding CODM. In some instances, the nucleic acid molecule encodes a hairpin RNA for reducing expression of an endogenous gene encoding T6ODM. In some instances, the nucleic acid molecule encodes a single hairpin RNA sufficient to reduce expression of endogenous genes encoding T6ODM and CODM. In some instances, the nucleic acid molecule comprises a portion of SEQ ID NO:2, SEQ ID NO:4, or both.

In some instances, the expression construct comprises a first nucleic acid molecule encoding a first hairpin RNA for reducing expression of an endogenous gene encoding T6ODM and a second nucleic acid molecule encoding a second hairpin RNA for reducing expression of an endogenous gene encoding CODM. In some instances, the endogenous gene encoding T6ODM encodes an mRNA comprising having the sequence of SEQ ID NO: 15. In some instances, the endogenous gene encoding T6ODM encodes a polypeptide having the sequence of SEQ ID NO 1. In some instances, the endogenous gene encoding CODM encodes an mRNA comprising having the sequence of SEQ ID NO: 16. In some instances, the endogenous gene encoding T6ODM encodes a polypeptide having the sequence of SEQ ID NO 3. In some instances, each of the first nucleic acid molecule and the second nucleic acid molecule comprise a portion of SEQ ID NO: 2, SEQ ID NO: 4, or both.

In some instances, the nucleic acid molecule encoding the hairpin RNA(s) comprises a portion of SEQ ID NO: 8. In some instances, the nucleic acid molecule encoding the hairpin RNA(s) comprises a portion of SEQ ID NO: 7.

In some instances, the first nucleic acid molecule comprises a portion of SEQ ID NO: 8. In some instances, the first nucleic acid molecule comprises a portion of SEQ ID NO: 7.

In some instances, the second nucleic acid molecule comprises a portion of SEQ ID NO: 8. In some instances, the second nucleic acid molecule comprises a portion of SEQ ID NO: 7.

In some instances, the plant or plant cell is genetically modified to have reduced activity of T6ODM, and the reduced activity of CODM is conferred by a mutation in the endogenous gene encoding CODM that was not introduced by genetic modification of the plant or plant cell. In some instances, mutation in the endogenous gene encoding CODM that was not introduced by genetic modification of the plant or plant cell is the mutation present in seeds of the plant deposited under Patent Deposit Designation PTA-9109.

In some instances, the plant is genetically modified to have reduced activity of CODM, and wherein reduced activity of T6ODM is conferred by a mutation in the endogenous gene encoding T6ODM that was not introduced by genetic modification of the plant or plant cell. In some instances, the mutation in the endogenous gene encoding T6ODM that was not introduced by genetic modification of the plant or plant cell is the mutation present in seeds of the plant deposited under Patent Deposit Designation PTA-9110.

Various aspects of the disclosure relate to a genetically modified poppy plant or plant cell having reduced expression of endogenous genes encoding 6-O-demethylase (T6ODM) and codeine 3-O-demethylase (CODM), the genetically modified plant comprising: a transgenic expression construct decreasing the expression of an endogenous gene encoding T6ODM in the plant or plant cell; and a transgenic expression construct decreasing the expression of an endogenous gene encoding CODM in the plant or plant cell.

Various aspects of the disclosure relate to seed of an opium poppy plant as described above.

Various aspects of the disclosure relate to use of a plant as described above for the production of thebaine.

Various aspects of the disclosure relate to poppy straw from a plant as described above.

Various aspects of the disclosure relate to latex isolated from a plant as defined above.

Various aspects of the disclosure relate to a method of producing thebaine, said method comprising isolating thebaine from latex or poppy straw harvested from a plant as described above.

Various aspects of the disclosure relate to an isolated nucleic acid molecule, wherein the sequence of the nucleic acid molecule comprises a portion of SEQ ID NO:7.

Various aspects of the disclosure relate to an expression vector for simultaneously reducing the expression of endogenous genes encoding thebaine 6-O-demethylase (T6ODM) and codeine 3-O-demethylase (CODM) in an opium poppy plant, the expression vector comprising a nucleic acid molecule that comprises a portion of SEQ ID NO:7.

Various aspects of the disclosure relate to use of a portion of a polynucleotide molecule having a sequence comprising a portion of SEQ ID NO: 2 or SEQ ID NO: 4 for simultaneously reducing the expression of endogenous genes encoding thebaine 6-O-demethylase (T6ODM) and codeine 3-O-demethylase (CODM) in an opium poppy plant.

Other aspects and features of the present invention will become apparent to those ordinarily skilled in the art upon review of the following description of specific embodiments of the invention in conjunction with the accompanying figures.

The methods disclosed herein may be useful for producing poppy plants having an increased ratio of thebaine:morphine.

Particular aspects of the disclosure relate to a method of increasing accumulation of thebaine in an opium poppy plant or plant cell, the method comprising genetically modifying the genome of the plant or plant cell to include one or more stable genetic modifications to simultaneously reduce the activity of thebaine 6-O-demethylase (T6ODM) and codeine 3-O-demethylase (CODM) in the poppy plant or plant cell.

Particular aspects of the disclosure relate to a genetically modified opium poppy plant or plant cell having reduced activity of thebaine 6-O-demethylase (T6ODM) and codeine 3-O-demethylase (CODM) relative to a wild type plant or plant cell, wherein the genetically modified opium poppy plant or plant cell comprises one or more stable genetic modifications to reduce expression of T6ODM, CODM, or both.

Particular aspects of the disclosure relate to a method for producing an opium poppy plant with increased thebaine content, the method comprising: (a) decreasing the expression of an endogenous gene encoding an endogenous thebaine 6-O-demethylase (T6ODM) in the plant; and (b) decreasing the expression of an endogenous gene encoding codeine 3-O-demethylase (CODM) in the plant, wherein decreasing the expression of the endogenous gene encoding T6ODM comprises genetically modifying the plant to have a loss of function allele in the endogenous gene encoding T6ODM.

Particular aspects of the disclosure relate to a method for producing an opium poppy plant with increased thebaine content, the method comprising: (a) decreasing the expression an endogenous gene encoding an endogenous thebaine 6-O-demethylase (T6ODM) in the plant; and (b) decreasing the expression of an endogenous gene encoding codeine 3-O-demethylase (CODM) in the plant, wherein decreasing the expression of the endogenous gene encoding T6ODM comprises expressing a heterologous nucleic acid molecule homologous to a portion of the endogenous gene encoding T6ODM, wherein expression of the heterologous nucleic acid molecule decreases expression of the endogenous gene encoding T6ODM.

Particular aspects of the disclosure to a method for producing an opium poppy plant with increased thebaine content, the method comprising: (a) decreasing the expression an endogenous gene encoding an endogenous thebaine 6-O-demethylase (T6ODM) in the plant; and (b) decreasing the expression of an endogenous gene encoding codeine 3-O-demethylase (CODM) in the plant, wherein decreasing the expression of the endogenous gene encoding CODM comprises genetically modifying the plant to have a loss of function allele in the endogenous gene encoding CODM.

Particular aspects of the disclosure to a method for producing an opium poppy plant with increased thebaine content, the method comprising: (a) decreasing the expression of an endogenous gene encoding an endogenous thebaine 6-O-demethylase (T6ODM) in the plant; and (b) decreasing the expression of an endogenous gene encoding codeine 3-O-demethylase (CODM) in the plant, wherein decreasing the expression of the endogenous gene encoding CODM comprises expressing a heterologous nucleic acid molecule homologous to a portion of the endogenous gene encoding CODM, wherein expression of the heterologous nucleic acid molecule decreases expression of the endogenous gene encoding CODM.

Particular aspects of the disclosure relate to a genetically modified poppy plant or plant cell having reduced expression of endogenous genes encoding 6-O-demethylase (T6ODM) and codeine 3-O-demethylase (CODM), the genetically modified plant comprising: a stably inherited transgenic expression construct for decreasing the expression of an endogenous gene encoding T6ODM in the plant or plant cell; and a stably inherited transgenic expression construct for decreasing the expression of an endogenous gene encoding CODM in the plant or plant cell.

Particular aspects of the disclosure relate to a method of generating an opium poppy plant having increased thebaine content relative to a wild type opium poppy plant, the method comprising: i) using a molecular methodology to identify a first plant as comprising a loss of function allele in an endogenous gene encoding codeine 3-O-demethylase (CODM); ii) establishing a cross of said first plant to a second plant having a loss of function allele in an endogenous gene encoding thebaine 6-O-demethylase (T6ODM); iii) allowing progeny from the cross to self-fertilize; and iv) screening progeny from self-fertilized plants for a plant that is homozygous for both the loss of function allele in the endogenous gene encoding CODM and the loss of function allele in the endogenous gene encoding T6ODM.

Particular aspects of the disclosure relate to a method of generating an opium poppy plant having increased thebaine content relative to a wild type opium poppy plant, the method comprising: i) using a molecular methodology to identify a first plant as comprising a loss of function allele in an endogenous gene encoding thebaine 6-O-demethylase (T6ODM); ii) establishing a cross of said first plant to a second plant having a loss of function allele in an endogenous gene encoding codeine 3-O-demethylase (CODM); iii) allowing progeny from the cross to self-fertilize; and iv) screening progeny from self-fertilized plants for a plant that is homozygous for both the loss of function allele in the endogenous gene encoding CODM and the loss of function allele in the endogenous gene encoding T6ODM.

Particular aspects of the disclosure relate to a method of generating an opium poppy plant having increased thebaine content relative to a wild type opium poppy plant, the method comprising: i) using a molecular methodology to identify a plant as comprising a loss of function allele in an endogenous gene encoding thebaine 6-O-demethylase (T6ODM); ii) genetically modifying the plant to introduce a loss of function allele in an endogenous gene encoding codeine 3-O-demethylase (CODM); iii) allowing the plant to self-fertilize; and iv) screening progeny from the self-fertilized plant for a plant that is homozygous for both the loss of function allele in the endogenous gene encoding CODM and the loss of function allele in the endogenous gene encoding T6ODM.

Particular aspects of the disclosure relate to a method of generating an opium poppy plant having increased thebaine content relative to a wild type opium poppy plant, the method comprising: i) using a molecular methodology to identify a plant as comprising a loss of function allele in an endogenous gene encoding codeine 3-O-demethylase (CODM); ii) genetically modifying the plant to introduce a loss of function allele in an endogenous gene encoding thebaine 6-O-demethylase (T6ODM) in the plant by genetic modification; iii) allowing the plant to self-fertilize; and iv) screening progeny from the self-fertilized plant for a plant that is homozygous for both the loss of function allele in the endogenous gene encoding CODM and the loss of function allele in the endogenous gene encoding T6ODM.

Particular aspects of the disclosure relate to a method of generating an opium poppy plant having increased thebaine content relative to a wild type opium poppy plant, the method comprising: i) using a molecular methodology to identify a plant as comprising a loss of function allele in an endogenous gene encoding thebaine 6-O-demethylase (T6ODM); ii) genetically modifying the plant to reduce expression of an endogenous gene encoding codeine 3-O-demethylase (CODM); iii) allowing the plant to self-fertilize; and iv) screening progeny from the self-fertilized plant for a plant that is homozygous for the loss of function allele in the endogenous gene encoding T6ODM and has reduced expression of the endogenous gene encoding CODM.

Particular aspects of the disclosure relate to a method of generating an opium poppy plant having increased thebaine content relative to a wild type opium poppy plant, the method comprising: i) using a molecular methodology to identify a plant as comprising a loss of function allele in an endogenous gene encoding codeine 3-O-demethylase (CODM); ii) genetically modifying the plant to reduce expression of an endogenous gene encoding thebaine 6-O-demethylase (T6ODM); iii) allowing the plant to self-fertilize; and iv) screening progeny from the self-fertilized plant for a plant that is homozygous for both the loss of function allele in the endogenous gene encoding CODM and has reduced expression of the endogenous gene encoding T6ODM.

Particular aspects of the disclosure relate to an isolated nucleic acid molecule, wherein the sequence of the nucleic acid molecule comprises SEQ ID NO:7.

Particular aspects of the disclosure relate to a use of a polynucleotide molecule having a sequence comprising a portion of SEQ ID NO: 2 or SEQ ID NO: 4 for simultaneously reducing the expression of endogenous genes encoding thebaine 6-O-demethylase (T6ODM) and codeine 3-O-demethylase (CODM) in an opium poppy plant.

Particular aspects of the disclosure relate to poppy straw harvest from a plant or plant cell as claimed.

Particular aspects of the disclosure related to latex harvested from a plant or a plant cell as claimed.

BRIEF DESCRIPTION OF THE DRAWINGS

In drawings which illustrate embodiments of the invention,

FIG. 3 is an alignment of cDNA sequences encoding CODM and T6ODM. The underlined portion identifies T6ODM sequences used in the creation of the hairpin RNA expression construct to reduce expression of both the endogenous gene encoding CODM and the endogenous gene encoding T6ODM. Differences between the T6ODM and CODM coding sequences within the underlined portion are highlighted in black.

DETAILED DESCRIPTION

Figure 1:
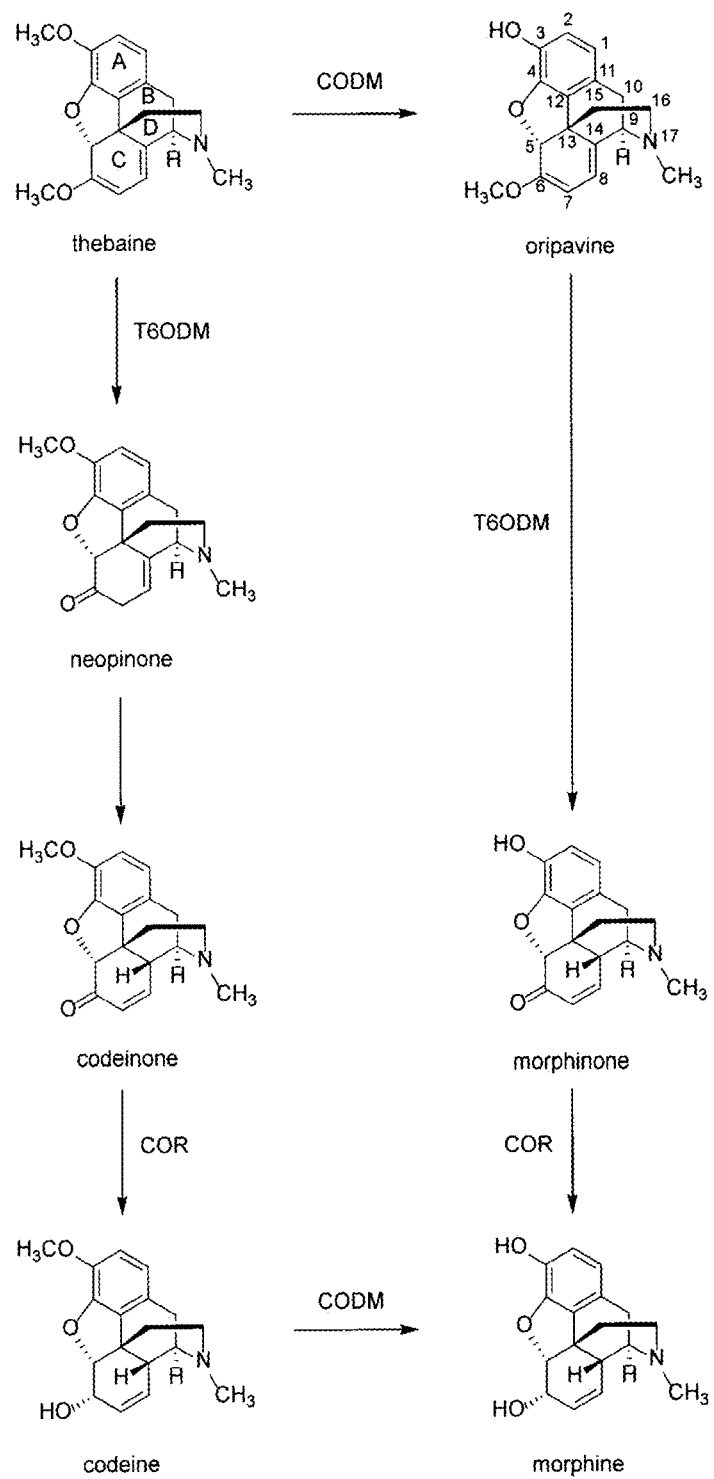
FIG. 1 is a schematic diagram of the morphine biosynthesis pathway in opium poppy, showing two routes from thebaine to morphine.

This disclosure relates to a genetically modified opium poppy plants, seeds, cells, straw, progeny thereof, or produced latex thereof, which genetically modified plant produces a latex having increased levels of thebaine relative to wild type plants due to the combined reduction in the activity of the enzymes thebaine 6-O-demethylase (T6ODM) and codeine 3-O-demethylase (CODM) during opiate biosynthesis. The disclosure also relates to methods of obtaining such genetically modified opium poppy plants.

Definitions

"Opium poppy plant" or "poppy plant" as used herein refers to a plant of the species *Papaver Somniferum*.

A "field" of plants as used herein, refers to a plurality of opium plants cultivated together in close proximity.

"Activity" or as used herein refers to the level of a particularly enzymatic function in a plant cell. In the context of the present disclosure, reduced T6ODM activity refers to a reduction in O-demethylation activity at position 6, whereas reduced CODM activity refers to a reduction in O-demethylation activity at position 3. Reduction in activity can be the result of diminished functionality of the protein due to, for example, mutation, or the result of reduced expression of the protein, for example, due to reduced translation.

A "genetic modification" as used herein broadly refers to any a novel combination of genetic material obtained with techniques of modern biotechnology. Genetic modifications include, but are not limited to, "transgenes" in which the genetic material has been altered by the insertion of exogenous genetic material. However, genetic modifications also include alterations (e.g. insertions, deletions, or substitutions) in endogenous genes introduced in a targeted manner with techniques such as CRISPR/Cas9, TALENS, etc. as discussed below. However, for the purposes of this disclosure "genetic modification" is not intended to include novel combinations of genetic material resulting from mutations generated by traditional means of random mutagenesis following by traditional means of breeding.

"Transgene" as used herein refers to a recombinant gene or genetic material that has been transferred by genetic engineering techniques into the plant cell. "Transgenic plants" or "transformed plants" as used herein refers to plants that have incorporated or integrated exogenous nucleic acid sequences or DNA fragments into the plant cell. A transgene may include a homologous or heterologous promoter operably linked to a DNA molecule encoding the RNA or polypeptide of interest.

"Operably linked" refers to a functional linkage between a promoter and a second DNA sequence, wherein the promoter sequence initiates and mediates transcription of the DNA sequence corresponding to the second DNA sequence. Generally, operably linked means that the nucleic acid sequences being linked are contiguous.

A "genetically modified" plant or plant cell as used herein broadly refers to any plant or plant cell that possesses a genetic modification as defined herein.

As used herein, the term "polypeptide" encompasses any chain of naturally or non-naturally occurring amino acids (either D- or L-amino acids), regardless of length (e.g., at least 5, 6, 8, 10, 12, 14, 16, 18, 20, 25, 30, 40, 50, 100 or more amino acids) or post-translational modification (e.g., glycosylation or phosphorylation) or the presence of e.g. one or more non-amino acyl groups (for example, sugar, lipid, etc.) covalently linked to the peptide, and includes, for example, natural proteins, synthetic or recombinant polypeptides and peptides, hybrid molecules, peptoids, peptidomimetics, etc. As used herein, the terms "polypeptide", "peptide" and "protein" may be used interchangeably.

"Nucleotide sequence", "polynucleotide sequence", "nucleic acid" or "nucleic acid molecule" as used herein refers to a polymer of DNA or RNA which can be single or double stranded and optionally containing synthetic, non-natural or altered nucleotide bases capable of incorporation into DNA or RNA polymers. "Nucleic acid", "nucleic acid sequence", "polynucleotide sequence" or "nucleic acid molecule" encompasses genes, cDNA, DNA and RNA encoded by a gene. Nucleic acids, nucleic acid sequences, polynucleotide sequence and nucleic acid molecule may comprise at least 3, at least 10, at least 100, at least 1000, at least 5000, or at least 10000 nucleotides or base pairs.

A "fragment", a "fragment thereof", "gene fragment" or a "gene fragment thereof" as used herein refers to a portion of a "nucleotide sequence", "polynucleotide sequence", "nucleic acid" or "nucleic acid molecule" that may still reduce expression of the gene(s) encoding CODM and/or T6ODM. In one embodiment, the fragment comprises at least 20, at least 40, at least 60, at least 80, at least 100, at least 150, at least 200, at least 150, at least 300, at least 350, at least 400, at least 450 or at least 500 contiguous nucleotides.

A "non-natural variant" as used herein refers to nucleic acid sequences native to an organism but comprising modifications to one or more of its nucleotides introduced by mutagenesis.

An "allele" or "allelic variant" as used herein refers to an alternate form of the same gene at a specific location of the genome.

"Wildtype" as used herein refers to a plant or plant material that was not transformed with a nucleic acid molecule or construct, genetically modified, or otherwise mutated as described herein. A "wildtype" may also refer to a plant or plant material in which T6ODM activity and CODM activity were not reduced.

The term "identity" as used herein refers to sequence similarity between two polypeptide or polynucleotide molecules. Identity can be determined by comparing each position in the aligned sequences. A degree of identity between amino acid or nucleic acid sequences is a function of the number of identical or matching amino acids or nucleic acids at positions shared by the sequences, for example, over a specified region. Optimal alignment of sequences for comparisons of identity may be conducted using a variety of algorithms, as are known in the art, including the Clustal W™ program, the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman, 1988, Proc. Natl. Acad. Sci. USA 85:2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm (e.g. BLASTn and BLASTp), described in Altschul et al., 1990, J. Mol. Biol. 215:403-10 (using the published default settings). Software for performing BLAST analysis is available through the National Center for Biotechnology Information. For instance, sequence identity between two nucleic acid sequences can be determined using the BLASTn algorithm at the following default settings: expect threshold 10; word size 11; match/mismatch scores 2, 3; gap costs existence 5, extension 2. Sequence identity between two amino acid sequences may be determined using the BLASTp algorithm at the following default settings: expect threshold 10; word size 3; matrix BLOSUM 62; gap costs existence 11, extension 1. In another embodiment, the person skilled in the art can readily and properly align any given sequence and deduce sequence identity/homology by mere visual inspection.

As used herein, "heterologous", "foreign" and "exogenous" DNA and RNA are used interchangeably and refer to DNA or RNA that does not occur naturally as part of the plant genome in which it is present or which is found in a location or locations in the genome that differ from that in which it occurs in nature. Thus, heterologous or foreign DNA or RNA is nucleic acid that is not normally found in the host genome in an identical context (i.e. linked to identical 5' and 3' sequences). In one aspect, heterologous DNA may be the same as the host DNA but introduced into a different place in the host genome and/or has been modified by methods known in the art, where the modifications include, but are not limited to, insertion in a vector, linked to a foreign promoter and/or other regulatory elements, or repeated at multiple copies. In another aspect, heterologous DNA may be from a different organism, a different species, a different genus or a different kingdom, as the host DNA. Further, the heterologous DNA may be a transgene. As used herein, "transgene" refers to a segment of DNA containing a gene sequence that has been isolated from one organism and introduced into a different organism. In the context of the present disclosure, the nucleic acid molecules may comprise nucleic acid that is heterologous to the plant in which CODM and T6ODM activity is reduced.

"Expression" or "expressing", as used herein refers to the process by which information from a gene is used in the synthesis of a functional gene product, and may relate to production of any detectable level of a product, or activity of a product, encoded by a gene. Gene expression may be modulated (i.e. initiated, increased, decreased, terminated, maintained or precluded) at many levels including transcription, RNA processing, translation, post-translational modification, protein degradation. Gene expression can also be modulated by the introduction of mutations that affect the activity of the gene product, e.g. the ability of a gene product to convert substrate. In the context of the present disclosure, reduced expression of the endogenous gene(s) encoding CODM and/or T6ODM, or reduced expression of the CODM and/or T6ODM polypeptides, can be effected by reduced transcription of the endogenous gene(s) encoding CODM and/or T6ODM, by reduced translation of mRNA transcripts coding for CODM and/or T6ODM, or by the introduction of mutations that either prevent the translation of functional polypeptides or result in the translation of polypeptides with reduced abilities to convert substrate. Such reduced expression of the endogenous genes may result from expression of transgenes comprising expression constructs designed to reduce expression of the endogenous genes.

"Poppy straw" as used herein refers to the straw material resulting from threshing of mature poppy capsules and the poppy capsule stems to remove the seeds.

"Latex" as used herein refer to the air-dried, milky exudation from lansed, unripe poppy capsules.

The term "increased thebaine content" or "increased level of thebaine" as used herein refers to a significantly increased levels of thebaine in one or more tissues as compared to the levels of thebaine in a corresponding wild type plant. The term "increased" also encompasses levels of thebaine that are significantly increased in one or more tissues compared to the same tissues of a wild type plant, while wild type levels of thebaine persist elsewhere in the plant.

The term "reduced morphine content" as used herein refers to a significantly decreased levels of morphine in one or more tissues as compared to the levels of morphine in a corresponding wild type plant. The term "reduced" also encompasses levels of morphine that are significantly reduced in one or more tissues compared to the same tissues of a wild type plant, while wild type levels of morphine persist elsewhere in the plant.

"Decreasing expression", "decreasing activity", "reducing expression", and "reducing activity" are intended to encompass well known equivalent terms regarding expression and activity such as "inhibiting", "down-regulating", "knocking out", "silencing", etc.

"substantially no" when referring to alkaloid content means that the particular alkaloid or combination of alkaloids constitutes less than 0.6% by weight, preferably, less than 0.5% by weight, more preferably, less than 0.4% by weight, or less than 0.2% by weight of the alkaloid combination of the poppy straw, concentrate of poppy straw or opium.

"Expression construct" as used herein refers to any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest into, for example, an siRNA.

An expression construct of the disclosure nucleic acid molecule may further comprise a promoter and other regulatory elements, for example, an enhancer, a silencer, a polyadenylation site, a transcription terminator, a selectable marker or a screenable marker.

As used herein, a "vector" or a "construct" may refer to any recombinant polynucleotide molecule such as a plasmid, cosmid, virus, vector, autonomously replicating polynucleotide molecule, phage, or linear or circular single-stranded or double-stranded DNA or RNA polynucleotide molecule, derived from any source. A "vector" or a "construct" may comprise a promoter, a polyadenylation site, an enhancer or silencer and a transcription terminator, in addition to a nucleotide sequence encoding a gene or a gene fragment of interest. As used herein, a "transformation vector" may refer to a vector used in the transformation of, or in the introduction of DNA into, cells, plants or plant materials.

As used herein, a "promoter" refers to a nucleotide sequence that directs the initiation and rate of transcription of a coding sequence (reviewed in Roeder, Trends Biochem Sci, 16: 402, 1991). The promoter contains the site at which RNA polymerase binds and also contains sites for the binding of other regulatory elements (such as transcription factors). Promoters may be naturally occurring or synthetic (see Datla et al. Biotech Ann. Rev 3:269, 1997 for review of plant promoters). Further, promoters may be species specific (for example, active only in *B. napus*); tissue specific (for example, the napin, phaseolin, zein, globulin, dlec2, γ-kafirin seed specific promoters); developmentally specific (for example, active only during embryogenesis); constitutive (for example maize ubiquitin, rice ubiquitin, rice actin, *Arabidopsis* actin, sugarcane bacilliform virus, CsVMV and CaMV 35S, *Arabidopsis* polyubiquitin, *Solanum bulbocastanum* polyubiquitin, *Agrobacterium tumefaciens*-derived nopaline synthase, octopine synthase, and mannopine synthase gene promoters); or inducible (for example the stilbene synthase promoter and promoters induced by light, heat, cold, drought, wounding, hormones, stress and chemicals). A promoter includes a minimal promoter that is a short DNA sequence comprised of a TATA box or an Inr element, and other sequences that serve to specify the site of transcription initiation, to which regulatory elements are added for control of expression. A promoter may also refer to a nucleotide sequence that includes a minimal promoter plus DNA elements that regulates the expression of a coding sequence, such as enhancers and silencers. Thus in one aspect, the expression of the constructs of the present disclosure may be regulated by selecting a species specific, a tissue specific, a development specific or an inducible promoter.

"Constitutive promoter" as used herein refers to a promoter which drives the expression of the downstream-located coding region in a plurality of or all tissues irrespective of environmental or developmental factors.

The skilled person will understand that it would be important to use a promoter that effectively directs the expression of the construct in the tissue in which thebaine is being synthesized. For example, the endogenous T6ODM or CODM promoters could be used. Alternatively, constitutive, tissue-specific, or inducible promoters useful under the appropriate conditions to direct high level expression of the introduced expression construct during opioid biosynthesis can be employed.

Enhancers and silencers are DNA elements that affect transcription of a linked promoter positively or negatively, respectively (reviewed in Blackwood and Kadonaga, Science, 281: 61, 1998).

Polyadenylation site refers to a DNA sequence that signals the RNA transcription machinery to add a series of the nucleotide A at about 30 bp downstream from the polyadenylation site.

Transcription terminators are DNA sequences that signal the termination of transcription. Transcription terminators are known in the art. The transcription terminator may be derived from *Agrobacterium tumefaciens*, such as those isolated from the nopaline synthase, mannopine synthase, octopine synthase genes and other open reading frame from Ti plasmids. Other terminators may include, without limitation, those isolated from CaMV and other DNA viruses, dlec2, zein, phaseolin, lipase, osmotin, peroxidase, PinII and ubiquitin genes, for example, from *Solanum tuberosum*.

In the context of the disclosure the nucleic acid construct may further comprise a selectable marker. Selectable markers may be used to select for plants or plant cells that contain the exogenous genetic material. The exogenous genetic material may include, but is not limited to, an enzyme that confers resistance to an agent such as a herbicide or an antibiotic, or a protein that reports the presence of the construct.

Numerous plant selectable marker systems are known in the art and are consistent with this invention. The following review article illustrates these well known systems: Miki and McHugh; Journal of Biotechnology 107: 193-232; Selectable marker genes in transgenic plants: applications, alternatives and biosafety (2004).

Examples of a selectable marker include, but are not limited to, a neo gene, which codes for kanamycin resistance and can be selected for using kanamycin, NptlI, G418, hpt etc.; an amp resistance gene for selection with the antibiotic ampicillin; an hygromycinR gene for hygromycin resistance; a BAR gene (encoding phosphinothricin acetyl transferase) which codes for bialaphos resistance including those described in WO/2008/070845; a mutant EPSP synthase gene, aadA, which encodes glyphosate resistance; a nitrilase gene, which confers resistance to bromoxynil; a mutant acetolactate synthase gene (ALS), which confers imidazolinone or sulphonylurea resistance, ALS, and a methotrexate resistant DHFR gene.

Further, screenable markers that may be used in the context of the invention include, but are not limited to, a β-glucuronidase or uidA gene (GUS), which encodes an enzyme for which various chromogenic substrates are known, green fluorescent protein (GFP), and luciferase (LUX).

Alkaloid Production in *Papaver somniferum*

FIG. 1 is a schematic diagram depicting two routes of morphine biosynthesis from thebaine. O-demethylation of thebaine at position 6 (ring C) is catalyzed by thebaine 6-O-demethylase (T6ODM) whereas O-demethylation at position 3 (ring A) is catalyzed by codeine O-demethylase (CODM). Thus, thebaine can undergo O-demethylation at position 6 or position 3 to yield neopinone or oripavine, respectively. Neopinone converts spontaneously to codeinone, which is then reduced to codeine by codeinone reductase (COR). Codeine is demethylated at position 3 by CODM to produce morphine. Demethylation of oripavine at position 6 by T6ODM yields morphinone, which is then reduced to morphine by COR.

The present inventor hypothesized that it may be possible to produce plants containing elevated levels of thebaine, and reduced levels of codeine and morphine, compared to parental plants by simultaneously reducing the activity of the T6ODM and CODM enzymes.

Wild type amino acid sequences of the T6ODM and CODM enzymes are presented in SEQ ID NOs: 1 and 3, respectively. The cDNA sequence corresponding to the endogenous gene coding for the T6ODM enzyme is presented as SEQ ID NO: 2, and the cDNA sequence corresponding to the endogenous gene coding for the CODM enzyme is presented as SEQ ID NO: 4. However, the skilled person will readily understand that naturally occurring variations in the T6ODM and CODM genes may exist between varieties, with slightly different nucleic acid sequences that encode the same functional protein.

Reduction of CODM and T6ODM Activity or Expression

CODM and T6ODM expression and/or activity in genetically modified plants of the present invention may be reduced by any method that results in reduced activity of these enzymes in the plant. This may be achieved by e.g. by altering CODM and T6ODM activity at the DNA, mRNA and/or protein levels.

As used herein, "activity" refers to the biochemical reaction of an enzyme with its cognate substrate. In the context of the invention, reduced T6ODM (or CODM) activity may result from reduced protein levels of T6ODM (or CODM) enzyme and/or the reduced rate at which a T6ODM (or CODM) enzyme catalyzes its reaction with thebaine.

Mutating Endogenous Genes Encoding CODM and T6ODM

In one aspect, the present disclosure relates to genetic modifications targeting the endogenous genes encoding CODM and T6ODM to alter CODM and T6ODM expression and/or activity. The endogenous CODM and T6ODM genes may be altered by, without limitation, knocking-out CODM and T6ODM genes; or knocking-in a heterologous DNA to disrupt CODM and T6ODM genes. The skilled person would understand that these approaches may be applied to the coding sequences, the promoter or other regulatory elements necessary for gene transcription. For example, technologies such as CRISPR/Cas9 and TALENS can be used to introduce loss of function mutations in both the endogenous genes encoding CODM and T6ODM. Plants having at least one allele of each gene comprising such loss of function mutations can then be self-fertilized to produce progeny homozygous for the loss of function alleles in the genes encoding CODM and T6ODM. In some embodiments, genetic modification of the endogenous gene encoding the CODM (or T6ODM) enzyme results in a polypeptide that differs in sequence by one or more amino acid insertions, deletions, or substitutions, and has diminished or no CODM (or T6ODM) activity.

Deletions involve lack one or more residues of the endogenous protein. For the purposes of this disclosure, a deletion variant includes embodiments in which no amino acids of the endogenous protein are translated, e.g. where the initial "start" methionine is substituted or deleted.

Insertional mutations typically involve the addition of material at a non-terminal point in the polypeptide, but may include fusion proteins comprising amino terminal and carboxy terminal additions. Substitutional variants typically involve a substitution of one amino acid for another at one or more sites within the protein, and may be designed to modulate one or more properties of the polypeptide. Substitutions of this kind may, in some embodiments, be conservative, i.e. where one amino acid is replaced with one of similar shape, size, charge, hydrophobicity, hydrophilicity, etc. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Accordingly, the CODM enzyme may have an amino acid sequence that possesses at least 60%, at least 70%, at least 80%, at least 90%, at least 95%, at least 96%, at least 97%, at least 98% or at least 99% sequence identity to SEQ ID NO: 1. Accordingly, the T6ODM enzyme may have an amino acid sequence that possesses at least 60%, at least 70%, at least 80%, at least 90%, at least 95%, at least 96%, at least 97%, at least 98% or at least 99% sequence identity to SEQ ID NO: 2.

Expression of Transgenes Targeting the Endogenous Genes

In another aspect, the present disclosure relates to reducing the expression and/or activity of CODM and T6ODM by targeting their respective mRNA transcripts. In this regard, levels of CODM and T6ODM T mRNA transcripts may be reduced by methods known in the art including, but not limited to, co-suppression, antisense expression, small hair pin (shRNA) expression, interfering RNA (RNAi) expression, double stranded (dsRNA) expression, inverted repeat dsRNA expression, micro interfering RNA (miRNA), simultaneous expression of sense and antisense sequences, or a combination thereof.

In one embodiment, the present disclosure relates to the use of nucleic acid molecules that are complementary, or essentially complementary, to at least a portion of the molecules set forth in SEQ ID NO:2 or SEQ ID NO:4. Nucleic acid molecules that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:2 or SEQ ID NO:4 under relatively stringent conditions such as those described herein. Nucleic acid molecules may be substantially complementary (or are homologues/have identity) if the two sequences hybridize to each other under moderately stringent, or preferably stringent, conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (see Ausubel, et al. (eds), 1989, Current Protocols in Molecular Biology, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, Laboratory Techniques in Biochemistry and Molecular Biology Hybridization with Nucleic Acid Probes, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH.

The phenomenon of co-suppression in plants relates to the introduction of transgenic copies of a gene resulting in reduced expression of the transgene as well as the endogenous gene. The observed effect depends on sequence identity between the transgene and the endogenous gene.

The term "RNA interference" (RNAi) refers to well-known methods for down-regulating or silencing expression of a naturally occurring gene in a host plant. RNAi employs a double-stranded RNA molecule or a short hairpin RNA to change the expression of a nucleic acid sequence with which they share substantial or total homology. For a review, see e.g. Agrawal, N. et al (2003) Microbiol Mol Biol Rev. 67(4): 657-685. RNA is both an initiator and target in the process. This mechanism targets RNA from viruses and transposons and also plays a role in regulating development and genome maintenance. Briefly, double stranded RNA is cleaved by the enzyme dicer resulting in short fragments of 21-23 bp (siRNA). One of the two strands of each fragment is incorporated into the RNA-induced silencing complex (RISC). The RISC associated RNA strand pairs with mRNA and induces cleavage of the mRNA. Alternatively, RISC associated RNA strand pairs with genomic DNA resulting in epigenetic changes that affect gene transcription. Micro RNA (miRNA) is a type of RNA transcribed from the genome itself and works in a similar way. Similarly, shRNA may be cleaved by dicer and associate with RISC resulting in mRNA cleavage.

Specific examples of gene silencing in poppy have been reported using RNAi approaches. In 2008, Allen et al. reported suppression of the gene encoding the morphinan pathway enzyme salutaridinol 7-O-acetyltransferase (SalAT) in opium poppy. Hairpin RNA-mediated suppression of SalAT resulted in the accumulation of salutaridine to 23% of total alkaloids. As discussed above in the Description of Related Art, Allen et al. (2004) silenced codeinone reductase (COR) in opium poppy using a chimeric hairpin RNA construct designed to silence all members of the multigene COR family through RNAi.

Antisense suppression of gene expression does not involve the catalysis of mRNA degradation, but instead involves single-stranded RNA fragments binding to mRNA and blocking protein translation.

Both antisense and sense suppression are mediated by silencing RNAs (sRNAs) produced from either a sense-antisense hybrid or double stranded RNA (dsRNA) generated by an RNA-dependant RNA polymerase. Major classes of sRNAs include short-interfering RNAs (siRNAs) and microRNAs (miRNAs) which differ in their biosynthesis.

Processing of dsRNA precursors by Dicer-Like complexes yields 21-nucleotide siRNAs and miRNAs guide cleavage of target transcripts from within RNA-induced silencing complexes (RISC).

T6ODM and CODM expression may be suppressed using a synthetic gene(s) or an unrelated gene(s) that contain about 21 bp regions or longer of high homology (preferably 100% homology) to the endogenous coding sequences for T6ODM and CODM.

See, for example, Jorgensen R A, Doetsch N, Muller A, Que Q, Gendler, K and Napoli C A (2006) A paragenetic perspective on integration of RNA silencing into the epigenome and in the biology of higher plants. Cold Spring Harb. Symp. Quant. Biol. 71:481-485. For a further review, see for example, Ossowski S, Schwab R and Weigel D (2008) Gene silencing in plants using artificial microRNAs and other small RNAs. The Plant Journal 53:674-690.

Nucleic acid molecules that are substantially identical to portions of the endogenous coding sequences for CODM and T6ODM may also be used in the context of the disclosure. As used herein, one nucleic acid molecule may be "substantially identical" to another if the two molecules have at least 60%, at least 70%, at least 80%, at least 82.5%, at least 85%, at least 87.5%, at least 90%, at least 92.5%, at least 95%, at least 96%, at least 97%, at least 98%, or at least 99% sequence identity. Thus, a nucleic acid sequence comprising a nucleic acid sequence that is at least 60%, at least 65%, at least 70%, at least 75%, at least 80%, at least 85%, at least 90%, at least 92.5%, at least 95%, at least 96%, at least 97%, at least 98% or at least 99% identical to SEQ ID NO: 2 or SEQ ID NO: 4 may be suitable for use in the context of this disclosure. In one embodiment, the two nucleic acid molecules each comprise at least 20 identical contiguous nucleotides.

Fragments of nucleic acid sequences encoding CODM or T6ODM may be used. Such fragments may have lengths of at least 20, at least 50, at least 100, at least 150, at least 200, at least 300 or at least 400 contiguous nucleotides of a nucleic acid sequence encoding a CODM or T6ODM as the case may be. Alternatively such fragments may have a minimum length of at least 20, at least 25, at least 30, at least 35, at least 40, at least 45, or at least 50 contiguous nucleotides and a maximum length less than 3000, less than 2000, less than 1750, less than 1500, less than 1250, less than 1000, less than 750 or less than 500 contiguous nucleotides or any combination of such minimum and maximum lengths of a nucleic acid sequence encoding CODM or T6ODM as the case may be.

In one embodiment, a genetically modified opium poppy plant of the disclosure comprises, stably integrated into its genome a first nucleic acid molecule heterologous to the plant. The first nucleic acid molecule encodes an RNA, e.g. a hairpin RNA, for reducing expression of the CODM enzyme. The genetically modified opium poppy plant further comprises and a second nucleic acid molecule heterologous to the plant. The second nucleic acid molecule encodes an RNA, e.g. a hairpin RNA, for reducing expression of the T6ODM enzyme.

The first and second nucleic acid molecules may be present in a single genetic construct or in multiple constructs. In one embodiment, the first and/or second nucleic acid molecules may be arranged in the sense orientation relative to a promoter. In another embodiment, the first and/or second nucleic acid molecules may be arranged in the anti-sense orientation relative to a promoter. In a further embodiment, a genetic construct may comprise at least two nucleic acid molecules in both the sense and anti-sense orientations, relative to a promoter. A genetic construct comprising nucleic acids in both the sense and anti-sense orientations may result in mRNA transcripts capable of forming stem-loop (hairpin) structures.

One or both of the nucleic acid molecules may be under transcriptional control of the same promoter.

In various instances, the first and second heterologous nucleic acid molecules respectively comprise:
  at least 20, at least 50, at least 100, at least 150, at least 200, at least 300 or at least 400 contiguous nucleotides of a nucleic acid sequence possessing at least 80%, at least 90% or 100% sequence identity to the nucleic acid sequence set forth in SEQ ID NO: 4;
  at least 20, at least 50, at least 100, at least 150, at least 200, at least 300 or at least 400 contiguous nucleotides of a nucleic acid sequence possessing at least 80%, at least 90% or 100% sequence identity to the nucleic acid sequence set forth in SEQ ID NO: 2.

In various instances, the first and second nucleic acid molecules respectively comprise:
  a nucleic acid molecule with a minimum length of at least 20, at least 25, at least 30, at least 35, at least 40, at least 45, or at least 50 contiguous nucleotides and a maximum length less than 1750, less than 1500, less than 1250, less than 1000, less than 750 or less than 500 contiguous nucleotides or any combination of such minimum and maximum lengths of a nucleic acid sequence possessing at least 80%, at least 90% or 100% sequence identity to the nucleic acid sequence set forth in SEQ ID NO:4; and a nucleic acid molecule with a minimum length of at least 20, at least 25, at least 30, at least 35, at least 40, at least 45, or at least 50 contiguous nucleotides and a maximum length less than 1750, less than 1500, less than 1250, less than 1000, less than 750 or less than 500 contiguous nucleotides or any combination of such minimum and maximum lengths of a nucleic acid sequence possessing at least 80%, at least 90% or 100% sequence identity to the nucleic acid sequence set forth in SEQ ID NO: 2.

The skilled person will also appreciate that the reduction in activity of CODM and T6ODM may not be limited by the number of different nucleic acid molecules introduced into a plant or plant cell. In one embodiment, one nucleic acid molecule may target one or both endogenous genes encoding the enzymes. Accordingly, in another embodiment, a genetically modified opium poppy plant of the disclosure comprises, stably integrated into its genome a nucleic acid molecule heterologous to the plant. The nucleic acid molecule encodes a single transcript comprising an RNA (e.g., a hairpin RNA) for reducing expression of the CODM enzyme and an RNA (e.g. a hairpin RNA) for reducing expression of the T6ODM enzyme. In the working embodiment specifically exemplified in this disclosure, the nucleic acid molecule encodes a single transcript comprising a single hairpin RNA for reducing expression of both the CODM enzyme and the T6ODM enzyme.

In one aspect, a nucleic acid molecule may comprise a portion(s) of the coding sequence for CODM (SEQ ID NO:

4); T6ODM (SEQ ID NO: 2); an allelic variant thereof; a non-natural variant thereof; a fragment thereof; or any combination thereof.

In one embodiment, a fragment of the coding sequence for T6ODM (SEQ ID NO: 2) is suitable for the production of an expression construct coding for an RNAi hairpin that targets expression of the endogenous coding sequences of both CODM and T6ODM. In the working embodiment specifically exemplified in this disclosure, such fragment comprises SEQ ID NO: 7. In the working embodiment specifically exemplified in this disclosure, such expression construct comprises SEQ ID NO: 5. In the working embodiment specifically exemplified in this disclosure, the RNAi hairpin is encoded by a nucleic acid comprising SEQ ID NO: 6.

An expression construct comprising nucleic acids in both orientations relative to a promoter may further comprise a spacer to separate the nucleic acid molecules in sense orientation and those in the anti-sense orientation. As used herein, a "spacer" may comprise at least 2, at least 5, at least 10, at least 20, at least 30, at least 40, at least 50, at least 75, at least 100, at least 150, or at least 200 nucleotides.

The skilled person will also readily understand that although in the foregoing illustrative examples partial CODM and T6ODM coding sequences were suggested for constructing the CODM and T6ODM constructs, complete CODM and T6ODM coding sequences, alternative CODM and/or T6ODM coding sequences, 5'UTR and/or 3'UTR, or mutated derivatives of these sequences can also be used. The maximum number of nucleic acid molecules that may be used in the context of the invention may be limited only by the maximum size of the construct that may be delivered to a target plant or plant cell using a given transformation method.

In various embodiments, genetically modified plants of the present disclosure may further comprise a third nucleic acid molecule heterologous to the plant. The third nucleic acid molecule is for increasing expression of Cyp80B3 to increase the total level of morphinans.

Expression of Transgenes Targeting the Endogenous CODM and T6ODM Polypeptides

In a further aspect, the disclosure relates to reducing CODM and/or T6ODM activity by targeting CODM and T6ODM at the protein level. For example, CODM (or T6ODM) activity may be reduced by affecting the post-translational modification of the enzyme; or by the introduction of a heterologous protein (e.g. a mutated form of CODM or (T6ODM) may be expressed such that it associates with the wildtype enzyme and alters its activity or outcompetes the wildtype enzyme for substrate without being able to convert the substrate; or an antibody that binds specifically to the CODM (or T6ODM) enzyme.

The skilled person would also appreciate that a nucleic acid molecule comprising the sequence of a CODM or T6ODM gene promoter and/or other regulatory elements may be used in the context of the invention. In an embodiment, a heterologous nucleic acid molecule comprising sequences of a CODM (or T6ODM as the case may be) gene promoter and/or regulatory element may be used to bias the cellular machinery away from an endogenous CODM (or T6ODM as the case may be) gene promoter thus resulting in reduced CODM (or T6ODM) expression.

The size or length of the nucleic acid construct or elements thereof, are not limited to the specific embodiments described herein. For example, the skilled person would appreciate that the size of a transgene element may be defined instead by transgene element function; and that the promoter element may be determined instead as one that was capable of driving transcription at a sufficient level and in the desired tissues. Similarly, the stem loop structure formed by the mRNA transcribed by a nucleic acid construct of the invention, may comprise a number of gene segments which may vary in length. For example, the stem loop may comprise 3 gene segments of about 21-30 basepairs each, in addition to a spacer, such as an intron (126 bp plus intron).

The skilled person would appreciate that the size of the gene segments may be established by the sum of the element sizes combined and may depend on the transformation method used to deliver the transgene into the target organism. For example, each transformation method (*Agrobacterium*, biolistics, VIGS-based delivery systems) may be limited to theoretical maximum transgene sizes.

Plant Transformation

The introduction of DNA into plant cells by *Agrobacterium* mediated transfer is well known to those skilled in the art. If, for example, the Ti or Ri plasmids are used for the transformation of the plant cell, at least the right border, although more often both the right and the left border of the T-DNA contained in the Ti or Ri plasmid must be linked to the genes to be inserted as flanking region. If agrobacteria are used for the transformation, the DNA to be integrated must be cloned into special plasmids and specifically either into an intermediate or a binary vector. The intermediate vectors may be integrated into the Ti or Ri plasmid of the agrobacteria by homologous recombination due to sequences, which are homologous to sequences in the T-DNA. This also contains the vir-region, which is required for T-DNA transfer. Intermediate vectors cannot replicate in agrobacteria. The intermediate vector can be transferred to *Agrobacterium tumefaciens* by means of a helper plasmid (conjugation). Binary vectors are able to replicate in *E. coli* as well as in agrobacteria. They contain a selection marker gene and a linker or polylinker framed by the right and left T-DNA border region. They can be transformed directly into agrobacteria. The *agrobacterium* acting as host cell should contain a plasmid carrying a vir-region. The vir-region is required for the transfer of the T-DNA into the plant cell. Additional T-DNA may be present. Such a transformed *agrobacterium* is used for the transformation of plant cells. The use of T-DNA for the transformation of plant cells has been intensively studied and has been adequately described in standard review articles and manuals on plant transformation. Plant explants cultivated for this purpose with *Agrobacterium tumefaciens* or *Agrobacterium rhizogenes* can be used for the transfer of DNA into the plant cell.

*Agrobacterium* transformation can be used to transform opium poppy plants (Chitty et al. (Meth. Molec. Biol, 344:383-391; Chitty et al. (Functional Plant Biol, 30: 1045-1058); Facchini et al. (Plant Cell Rep., 27(4):719-727)). Facchini et al. (2008) disclosed *A. tumefaciens*-mediated genetic transformation protocol via somatic embryogenesis for the production of fertile, herbicide-resistant opium poppy plants. Transformation was mediated using pCAMBIA3301, a transformation vector that harbors the phosphinothricin acetyltransferase (pat) gene driven by the cauliflower mosaic virus (CaMV) 35S promoter and the β-glucuronidase (GUS) gene also driven by the CaMV 35S promoter. Explants were co-cultivated with *A. tumefaciens* in the presence of 50 1M ATP and 50 1M MgCl2. Root explants pre-cultured on callus induction medium were then used for transformation. Herbicide-resistant, proliferating callus was obtained from explants on a medium containing both 2,4-dichlorophenoxyacetic acid (2,4-D) and 6-benzyladenine (BA). Globular embryo genie callus was induced by removal of the BA from the medium, and placed on a hormone-free medium to form somatic embryos. The somatic embryos were converted to plantlets under specific culture conditions and transferred to soil. Plants were allowed to mature and set seed. PAT and GUS transcripts and enzyme activities were detected in the transgenic lines tested.

Nevertheless, the present invention is not limited to any particular method for transforming plant cells, and the skilled person will readily understand that any other suitable method of DNA transfer into plant may be used. Methods for introducing nucleic acids into cells (also referred to herein as "transformation") are known in the art and include, but are not limited to: Viral methods (Clapp. Clin Perinatol, 20: 155-168, 1993; Lu et al. J Exp Med, 178: 2089-2096, 1993; Eglitis and Anderson. Biotechniques, 6: 608-614, 1988; Eglitis et al, Avd Exp Med Biol, 241: 19-27, 1988); physical methods such as microinjection (Capecchi. Cell, 22: 479-488, 1980), electroporation (Wong and Neumann. Biochim Biophys Res Commun, 107: 584-587, 1982; Fromm et al, Proc Natl Acad Sci USA, 82: 5824-5828, 1985; U.S. Pat. No. 5,384,253) and the gene gun (Johnston and Tang. Methods Cell Biol, 43: 353-365, 1994; Fynan et al. Proc Natl Acad Sci USA, 90: 11478-11482, 1993); chemical methods (Graham and van der Eb. Virology, 54: 536-539, 1973; Zatloukal et al. Ann NY Acad Sci, 660: 136-153, 1992); and receptor mediated methods (Curie) et al. Proc Natl Acad Sci USA, 88: 8850-8854, 1991; Curiel et al. Hum Gen Ther, 3: 147-154, 1992; Wagner et al. Proc Natl Acad Sci USA, 89: 6099-6103, 1992).

Another method for introducing DNA into plant cells is by biolistics. This method involves the bombardment of plant cells with microscopic particles (such as gold or tungsten particles) coated with DNA. The particles are rapidly accelerated, typically by gas or electrical discharge, through the cell wall and membranes, whereby the DNA is released into the cell and incorporated into the genome of the cell. This method is used for transformation of many crops, including corn, wheat, barley, rice, woody tree species and others. Biolistic bombardment has been proven effective in transfecting a wide variety of animal tissues as well as in both eukaryotic and prokaryotic microbes, mitochondria, and microbial and plant chloroplasts (Johnston. Nature, 346: 776-777, 1990; Klein et al. Bio/Technol, 10: 286-291, 1992; Pecorino and Lo. Curr Biol, 2: 30-32, 1992; Jiao et al, Bio/Technol, 11: 497-502, 1993).

Another method for introducing DNA into plant cells is by electroporation. This method involves a pulse of high voltage applied to protoplasts/cells/tissues resulting in transient pores in the plasma membrane which facilitates the uptake of foreign DNA. The foreign DNA enter through the holes into the cytoplasm and then to the nucleus.

Plant cells may be transformed by liposome mediated gene transfer. This method refers to the use of liposomes, circular lipid molecules with an aqueous interior, to deliver nucleic acids into cells. Liposomes encapsulate DNA fragments and then adhere to the cell membranes and fuse with them to transfer DNA fragments. Thus, the DNA enters the cell and then to the nucleus.

Other well-known methods for transforming plant cells which are consistent with the present invention include, but are not limited to, pollen transformation (See University of Toledo 1993 U.S. Pat. No. 5,177,010); Whiskers technology (See U.S. Pat. Nos. 5,464,765 and 5,302,523).

The nucleic acid constructs of the present invention may be introduced into plant protoplasts. Plant protoplasts are cells in which its cell wall is completely or partially removed using either mechanical or enzymatic means, and may be transformed with known methods including, calcium phosphate based precipitation, polyethylene glycol treatment and electroporation (see for example Potrykus et al., Mol. Gen. Genet., 199: 183, 1985; Marcotte et al., Nature, 335: 454, 1988). Polyethylene glycol (PEG) is a polymer of ethylene oxide. It is widely used as a polymeric gene carrier to induce DNA uptake into plant protoplasts. PEG may be used in combination with divalent cations to precipitate DNA and effect cellular uptake. Alternatively, PEG may be complexed with other polymers, such as poly(ethylene imine) and poly L lysine.

A nucleic acid molecule of the present invention may also be targeted into the genome of a plant cell by a number of methods including, but not limited to, targeting recombination, homologous recombination and site-specific recombination (see review Baszcynski et al. Transgenic Plants, 157: 157-178, 2003 for review of site-specific recombination systems in plants). Homologous recombination and gene targeting in plants (reviewed in Reiss. International Review of Cytology, 228: 85-139, 2003) and mammalian cells (reviewed in Sorrell and Kolb. Biotechnology Advances, 23: 431-469, 2005) are known in the art.

As used herein, "targeted recombination" refers to integration of a nucleic acid construct into a site on the genome, where the integration is facilitated by a construct comprising sequences corresponding to the site of integration.

Homologous recombination relies on sequence identity between a piece of DNA that is introduced into a cell and the cell's genome. Homologous recombination is an extremely rare event in higher eukaryotes. However, the frequency of homologous recombination may be increased with strategies involving the introduction of DNA double-strand breaks, triplex forming oligonucleotides or adeno-associated virus.

As used herein, "site-specific recombination" refers to the enzymatic recombination that occurs when at least two discrete DNA sequences interact to combine into a single nucleic acid sequence in the presence of the enzyme. Site-specific recombination relies on enzymes such as recombinases, transposases and integrases, which catalyse DNA strand exchange between DNA molecules that have only limited sequence homology. Mechanisms of site specific recombination are known in the art (reviewed in Grindley et al. Annu Rev Biochem, 75: 567-605, 2006). The recognition sites of site-specific recombinases (for example Cre and att sites) are usually 30-50 bp. The pairs of sites between which the recombination occurs are usually identical, but there are exceptions e.g. attP and attB of λ integrase (Landy. Ann Rev Biochem, 58: 913-949, 1989).

Additional methods might be selected from the resent years of development of methods and compositions to target and cleave genomic DNA by site specific nucleases e.g. Zinc Finger Nucleases, ZFNs, Meganucleases, Transcription Activator-Like Effector Nucleases, TALENS and Clustered Regularly Interspaced Short Palindromic Repeats/CRISPR-associated nuclease (CRISPR/Cas) with an engineered crRNA/tracr RNA), to induce targeted mutagenesis, induce targeted deletions of cellular DNA sequences, and facilitate targeted recombination of an exogenous donor DNA polynucleotide within a predetermined genomic locus. Current methods for targeted insertion of exogenous DNA typically involve co-transformation of plant tissue with a donor DNA polynucleotide containing at least one transgene and a site specific nuclease, e.g., ZFN, which is designed to bind and cleave a specific genomic locus of an actively transcribed coding sequence. This causes the donor DNA polynucleotide to stably insert within the cleaved genomic locus resulting in targeted gene addition at a specified genomic locus comprising an actively transcribed coding sequence.

As used herein the term "zinc fingers," defines regions of amino acid sequence within a DNA binding protein binding domain whose structure is stabilized through coordination of a zinc ion.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. (U.S. Pat. No. 6,453,242; see also WO 98/53058).

A "TALE DNA binding domain" or "TALE" is a polypeptide comprising one or more TALE repeat domains/units. The repeat domains are involved in binding of the TALE to its cognate target DNA sequence. A single "repeat unit", also referred to as a "repeat", is typically 33-35 amino acids in length and exhibits at least some sequence homology with other TALE repeat sequences within a naturally occurring TALE protein. (U.S. Patent Publication No. 2011/0301073).

The CRISPR (Clustered Regularly Interspaced Short Palindromic Repeats)/Cas (CRISPR Associated) nuclease system. Briefly, a "CRISPR DNA binding domain" is a short stranded RNA molecule that acting in concert with the CAS enzyme can selectively recognize, bind, and cleave genomic DNA. The CRISPR/Cas system can be engineered to create a double-stranded break (DSB) at a desired target in a genome, and repair of the DSB can be influenced by the use of repair inhibitors to cause an increase in error prone repair. (Jinek et al (2012) Science 337, p. 816-821).

Zinc finger, CRISPR and TALE binding domains can be "engineered" to bind to a predetermined nucleotide sequence, for example via engineering (altering one or more amino acids) of the recognition helix region of a naturally occurring zinc finger. Similarly, TALEs can be "engineered" to bind to a predetermined nucleotide sequence, for example by engineering of the amino acids involved in DNA binding (the repeat variable diresidue or RVD region). Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. (U.S. Pat. No. 6,453,242; see also WO 98/53058; and U.S. Publication Nos. 2011/0301073).

A "selected" zinc finger protein, CRISPR or TALE is a protein not found in nature whose production results primarily from an empirical process such as phage display, interaction trap or hybrid selection.

In one embodiment, the polynucleotide encodes a zinc finger protein that binds to a gene encoding a T6ODM or a CODM polypeptide, resulting in reduced expression of the gene. In particular embodiments, the zinc finger protein binds to a regulatory region of a gene encoding T6ODM or CODM. In other embodiments, the zinc finger protein binds to a messenger RNA encoding a T6ODM or a CODM polypeptide and prevents its translation. Methods of selecting sites for targeting by zinc finger proteins have been described, for example, in U.S. Pat. No. 6,453,242, and methods for using zinc finger proteins to inhibit the expression of genes in plants are described, for example, in US2003/0037355, each of which is herein incorporated by reference. Methods of selecting sites for targeting by TALE proteins have been described in e.g. Moscou M J, Bogdanove A J, 2009, A simple cipher governs DNA recognition by TAL effectors. Science 326:1501.

The nucleic acid molecule becomes stably integrated into the plant genome such that it is heritable to daughter cells in order that successive generations of plant cells have reduced CODM and T6ODM expression. This may involve the nucleic acid molecules of the present invention integrating, for instance integrating randomly, into the plant cell genome. Alternatively, the nucleic acid molecules of the present invention may remain as exogenous, self-replicating DNA that is heritable to daughter cells. As used herein, exogenous, self-replicating DNA that is heritable to daughter cells is also considered to be "stably integrated into the plant genome".

Testing for Reduction of CODM and T6ODM Activity or Expression

Disruption of endogenous genes encoding CODM and T6ODM, their expression, or CODM and T6ODM enzymatic activity may be confirmed by methods known in the art of molecular biology. For example, disruption of endogenous genes may be assessed by PCR followed by Southern blot analysis. CODM and T6ODM mRNA levels may, for example, be measured by real time PCR, RT-PCR, Northern blot analysis, micro-array gene analysis, and RNAse protection. CODM and T6ODM protein levels may, without limitation, be measured by enzyme activity assays, ELISA and Western blot analysis. CODM and T6ODM expression, or lack thereof, may be used as a predictor of increased thebaine accumulation. CODM and/or T6ODM enzymatic activity may be assessed biochemically or functionally.

For example, CODM (and/or T6ODM) activity may be measured biochemically by methods known in the art including, but not limited to, the detection of products formed by the enzyme in the presence of any number of heterologous substrates, for example, thebaine. CODM (and/or T6ODM) activity may also be measured functionally, for example, by assessing thebaine levels in the poppy tissues.

A genetically modified opium poppy plant of the present disclosure may result in the reduction of CODM and/or T6ODM activity in said plant or its seed, seedling, straw, capsules, or progeny thereof, by at least 57%, at least 60%, at least 65%, at least 70%, at least 75%, at least 80%, at least 85%, at least 90%, at least 95%, or 100% relative to a wild type seed, seedling, straw, capsules, or progeny thereof.

Targeted Screening for Loss of Function Mutations in CODM and/or T6ODM.

This disclosure further relates to methods of generating opium poppy plants with high levels of thebaine that involve targeted screening for loss of function mutations in the endogenous genes encoding CODM and/or T6ODM and subsequent breeding of plants to combine the mutations to obtain plants homozygous for the loss of function mutations at both loci. Opium poppy breeders have used a variety of selection techniques in the development of improved cultivars. However, the most successful breeding method involving the hybridization of parents with a variety of different desired characteristics. Such approach has been used successfully to increase capsule numbers, seed and opium yield, morphine content, and lodging resistance.

The term "T-DNA insertion" refers to methods utilizing transfer-DNA (T-DNA) for disrupting genes via insertional mutagenesis. Down-regulating or silencing expression of the endogenous gene(s) encoding CODM and/or T6ODM in an opium poppy plant can thus be achieved by T-DNA mutagenesis, wherein the T-DNA is used to randomly inserting in the plant genome to introduce mutations. Subsequently, plants can be screen for T-DNA insertions in the genes encoding CODM and/or T6ODM by PCR, using a primer pair comprising one primer specific for the T-DNA and one primer specific for the gene encoding CODM (or T6ODM as the case may be), or other high-throughput technologies. For a review of T-DNA as an insertional mutagen, see e.g. Krysan, P. J. et al. (1999) Plant Cell, 11: 2283-2290. Insertional mutagenesis using transposons could also be employed.

Mutations (including deletions, insertions, and point mutations) can also be introduced randomly into the genome of a plant cell by various forms of mutagenesis to produce non-natural variants. Methods for mutagenesis of plant materials, including seeds, and subsequent screening or selection for desired phenotypes are well known, as described in WO2009109012. Mutagenized plants and plant cells can also be specifically screened for mutations in the genes encoding CODM and/or T6ODM, for example, by TILLING (Targeting Induced Local Lesions IN Genomes). Loss of function mutations present in natural plant populations can be identified by EcoTILLING.

Once the loss of function mutations in the endogenous genes encoding CODM and T6ODM have been identified, they can be combined through traditional breeding processes to produce plants homozygous for the loss of function mutations at both loci. Alternatively, a loss of function mutation identified in the endogenous gene encoding CODM can be combined with mutations in the endogenous gene encoding T6ODM that are introduced by genetic modification, and vice versa. Alternatively, a loss of function mutation identified in the endogenous gene encoding CODM can be combined with genetic modification comprising an expression construct designed to reduce expression of T6ODM as described above, and vice versa.

Alkaloid Collection and Analysis

Opium poppy cultivation and opium harvesting traditionally involved the processes of manually lancing the seed capsule and collecting the latex. However, methods to extract morphine and related compounds from opium poppy straw circumvented the traditional technique and makes it possible to obtain high quality seeds and pharmaceutically valuable raw materials simultaneously. Recovering thebaine from poppy straw or latex of an opium poppy plant is well known in the art as discussed in WO2009109012. IN addition to the particular methods described below, methods of analyzing alkaloid extracts from opium poppy straw or latex are also discussed in WO2009109012.

Examples

Figure 2:
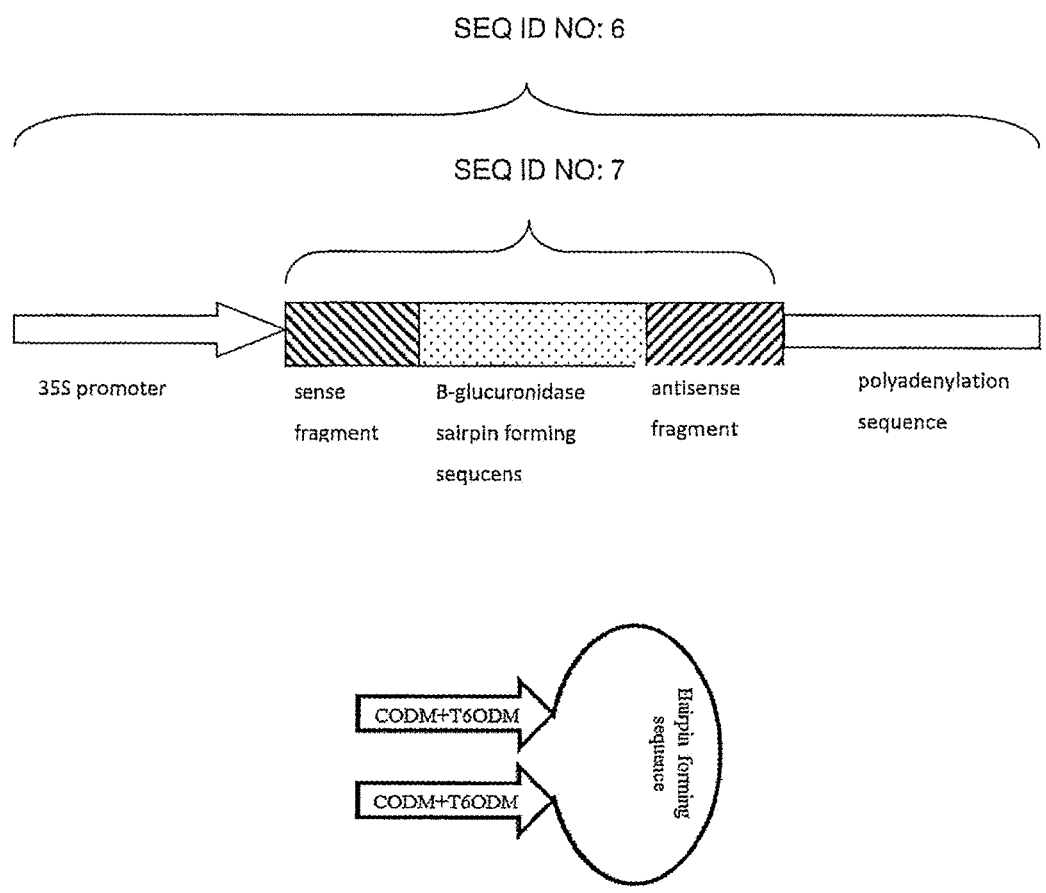
FIG. 2 is a schematic diagram of a hairpin RNA expression cassette for expressing a hairpin RNA comprising T6ODM sequences for simultaneous reduction of expression of the genes encoding CODM and T6ODM.

Referring to FIG. 2, the inventor used a single hairpin construct targeting genes coding for CODM and T6ODM enzymes to test the hypothesis that plants containing elevated levels of thebaine (and reduced levels of codeine and morphine) compared to parental plants can be produced by simultaneously reducing the activity of the T6ODM and CODM enzymes.

Referring to FIG. 3, the coding sequences for CODM and T6ODM genes have very high level of identity. Accordingly, the inventor created a single expression construct to target both the endogenous gene encoding CODM and the endogenous gene encoding T6ODM from a portion of the T6ODM coding sequence by RNAi. The portion of the T6ODM coding sequence used for the sense and antisense portions of the RNAi gene construct depicted in FIG. 2 is underlined in FIG. 3. A 342 base pair sense fragment was amplified from cDNA isolated from opium poppy plant material using primers SEQ ID NO: 17: AAAGGCGCGCCCCTTGTCCT-CAACCAAAT and SEQ ID NO: 18: AAAATTTAAATTC-CACTTTTAAACAAAGC). A 342 base pair antisense fragment was amplified from cDNA isolated from opium poppy plant material using primers SEQ ID NO: 19: AAAACTAGTCCTTGTCCTCAACCAAAT), OPP026 (SEQ ID NO: 20: AAAGGATCCTCCACTTT-TAAACAAAGC). These two fragments were used to create a nucleotide molecule with these to fragments interposed by sequences from β-glucuronidase.

The sequence of the nucleic acid molecule to be transcribed to produce a hairpin RNA is provided as SEQ ID NO: 6. The T6ODM sequences are underlined, whereas the intervening "hairpin" sequence between the T6ODM sequences is derived from coding sequences for β-glucuronidase.

The complete expression construct comprising SEQ ID NO: 6 along with the Cauliflower Mosaic Virus 35S promoter and transcription and translation termination sequences from octopine synthase was cloned into a TDNA transfer vector. The sequences between the left and right boarders of the vector are provided as provided as SEQ ID NO: 5. The sequence 5' to the first underlined region (i.e. the "sense" T6ODM-specific sequence) comprises the 35S promoter sequence, whereas the sequences 3' to the second underlined region (i.e. the "antisense" T6ODM-specific sequence) comprises the transcription and translation termination sequences from octopine synthase.

While this expression construct was generated using a combination of traditional polymerase chain reaction (PCR) and cloning techniques (e.g. with restriction enzymes and ligations), the skilled person will understand that various conventional techniques could be used to produce the construct, including overlap extension PCR cloning or direct synthesis.

The sequence of the entire T-DNA comprising SEQ ID NO:6, from Right Border to Left Border, is provided as SEQ ID NO: 4.

Virus-induced gene silencing (VIGS) was used to transiently test the ability of the gene cassette to silence the endogenous genes encoding T6ODM and CODM. VIGS is a plant RNA-silencing technique that uses viral vectors carrying a fragment of a gene of interest to generate double-stranded RNA, which initiates the silencing of the target gene. pTRV1 (helper plasmid) and pTRV2 (binary vector) TRV-based VIGS vectors to express the expression construct. Tissues were taken in 48 hrs, 72 hrs, 5 day, 7 days, and 2 weeks after infiltration. As indicated in FIGS. 4a and 4b, transient expression of the expression construct resulted in substantial downregulation of transcripts from the endogenous genes encoding CODM and
T6ODM at 48 h post transformation (first bar from the right in both FIGS. 3a and 3b above).

Plants stably transformed with the expression construct were then generated according to the following protocol.

Transformation Protocol

Transformation of Poppy Hypocotyls/Roots

Media Required:
LB
Agrobacterium Suspension Medium
B5 salts and vitamins containing 20 g/l sucrose, pH 5.6 5.8±0.2.
Shoot Germination Medium
Half strength Murashige and Skoog basal medium supplemented with 20 g/l sucrose, 8 g/l agar. pH 5.8±0.2.
Primary Callus Induction Medium
B5 medium containing 30 g/l sucrose, 2.0 mg/l NAA, and 0.1 mg/l BAP, 8 g/l agar.
Somatic Embryo Induction Medium
B5 medium containing 1.0 mg/l NAA, 0.5 mg/l BAP, 50 mg/l paromomycin, 300 mg/l timentin and 8 g/l agar.
Embryo Induction Medium
Murashige and Skoog basal medium supplemented with 30 g/l sucrose, 0.25 g/l MES, 0.2 g/l myo-inositol, 1 mg/l 2,4-D, 2.5 mg/l $AgNO_3$, 8 g/l agar. pH 5.6±0.2. (Plus antibiotic—Timentin 300 mg/l)
Embryo Maturation and Germination
Murashige and Skoog basal medium supplemented with 30 g/l sucrose, 0.25 g/l MES, 0.2 g/l myo-inositol, 1 mg/l Benzyl adenine, 1 mg/l Zeatin, 2.5 mg/l $AgNO_3$, 8 g/l agar. pH 5.6±0.2. (Plus antibiotic—Timentin 300 mg/l)
Phytohormone-Free Plant Regeneration Medium
B5 medium containing 50 mg/L paromomycin, 300 mg/L timentin, and 8 g/L agar
Shoot Elongation Medium
Murashige and Skoog basal medium supplemented with 30 g/l sucrose, 0.25 g/l MES, 0.2 g/l myo-inositol, 0.5 mg/l Benzyl adenine, 2.5 mg/l $AgNO_3$, 8 g/l agar. pH 5.6±0.2. (Plus antibiotic—Timentin 300 mg/l)
Rooting Medium
Murashige and Skoog basal medium supplemented with 30 g/l sucrose, 0.25 g/l MES, 0.2 g/l myo-inositol, 2.5 mg/l $AgNO_3$, 8 g/l agar. pH 5.6±0.2. (Plus antibiotic Timentin 300 mg/l)
Seed Sterilization and Germination
The seeds were surface-sterilized with 70% (vv-$^1$) ethanol for 30 s and 1% (vv-$^1$) sodium hypochlorite solution for 2 min each three times, then rinsed five times in sterile water. Approximately 50 seeds were placed on 25 ml of agar-solidified culture medium in jars. The basal medium consisted of ½ Murashige and Skoog basal medium supplemented with 30 g/l sucrose (Gamborg et al. 1968) and solidified with 0.8% (wv-$^1$) agar. The medium was adjusted to pH 5.6-5.8 before adding the agar, and then sterilized by autoclaving. The seeds were germinated in a growth chamber at 25° C. under standard cool white fluorescent tubes and a 16-h photoperiod.
Preparation of Agrobacterium tumefaciens
The binary vector pORE::ALM-MIRMAC was mobilized by electroporation in Agrobacterium tumefaciens strain EHA105. A. tumefaciens cultures were grown at 28° C. on a gyratory shaker at 180 rpm in liquid Luria-Bertani medium [1% tryptone, 0.5% yeast extract, and 1% NaCl, pH 7.0] containing 50 mg/l kanamycin and rifampicin 100 mg/l, to $A_{600}$=0.8. The bacterial cells were collected by centrifugation for 10 min at 4000 rpm and resuspended at a cell density of $A_{600}$=0.5 in liquid inoculation medium (B5 salts and vitamins containing 20 g/l sucrose).

Production of Transgenic Plants

Excised cotyledons from 12-day-old seedlings, line 118, were isolated by longitudinal bisection of the hypocotyl. The hypocotyls were dipped into the A. tumefaciens culture in liquid inoculation medium for 15 min, blotted dry on sterile filter paper, and incubated in the dark at 25° C. on primary callus induction medium. After 2 days of co-cultivation with A. tumefaciens, the hypocotyls were transferred to fresh primary callus induction medium containing 50 mg/L paromomycin and 300 mg/L timentin. After 4-5 weeks of incubation, primary calli were subcultured on somatic embryo induction medium. After 3 weeks of cultivation on induction medium, somatic embryos were transferred to phytohormone-free plant regeneration medium. Mature embryos were placed on phytohormone-free medium and immature embryos were transferred to embryo maturation and germination medium. Then, when first cotyledons appeared they were transplanted onto shoot elongation medium. Finally, when shoots were about 0.5-1 cm, they were placed on rooting medium. Regenerated putative transgenic plantlets were grown in a growth chamber at 25° C. under standard cool-white conditions and a 16-h photoperiod. Rooted plantlets were then transferred to pots containing autoclaved soil, covered with polyethylene bags for 1 week to sustain high humidity, and maintained in the growth chamber at 25° C. for 1-2 weeks before the plants were transferred to the greenhouse.

Method:
1. Pick a single colony of the desired construct in Agrobacterium and inoculate it in 2 ml LB liquid medium containing appropriate antibiotics; culture overnight at 28° C. to prepare a starter culture.
2. Inoculate 100 ml LB liquid medium containing appropriate antibiotics with the starter culture and incubate overnight at 28° C. Incubate cells until a desired $OD_{600}$=0.5-0.8 is attained.
3. Pellet the cells by centrifugation at 4000 rpm for 10 mins.
4. Resuspend the cells in Agrobacterium suspension medium to a final $OD_{600}$=0.5.
5. Roots and hypocotyl segments from 12 day old seedlings were cut into ~5 mm segments while dipping in the Agrobacterium suspension.
6. Incubate the roots and hypocotyl segments on Petri dish for 15 mins in the Agrobacterium suspension with occasional swirling.
7. Blot dry the roots and hypocotyl segments on a sterile filter paper and transfer to plates containing primary callus induction medium. Incubate the plates for 2 days at 22±2° C. in a growth cabinet under dark (covered with aluminium foil).
8. After 2 days of co-cultivation, wash the root and hypocotyl segments with sterile distilled water, blot dry on a sterile filter paper and transfer to plates containing primary callus induction medium (antibiotic paromomycin was added).
9. Incubate the plates in growth chamber at standard conditions (16/8 h photoperiod) in dark (covered with aluminium foil) for approximately 4-5 weeks.
10. After 4-5 weeks of incubation, primary calli were subcultured on somatic embryo induction medium (antibiotic paromomycin was added).
11. After 3 weeks of cultivation on induction medium, mature somatic embryos were transferred to phytohormone free medium (no antibiotic). Immature embryos were placed to another round of selection on embryo maturation and germination medium (no antibiotic) and incubated at 22±2° C. in a growth cabinet under 16/8 h photoperiod until embryos matured and started germinating.

12. Transfer the germinating embryos to plates containing shoot elongation medium until shoots appear and subsequently transfer to rooting medium.
13. Transfer ~0.5-1.0 cm shoots to rooting medium.
14. Rooted plantlets are washed under tap water to remove the entire adhering agar and then are transferred to sterile soil in small pots, covered with saran wrap and incubated in a growth cabinet for acclimatization.
15. Obtained putative transformants are analysed for transgene presence and expression.

Notes:—no antibiotic in rooting media.

Chemicals 1. 50 mg/ml Paromomycin sulfate stock: Prepare by dissolving powder in water and sterilize by filtration, aliquot, and store at −20 C.
2. 50 mg/ml Kanamycin stock: Prepare by dissolving powder in water and sterilize by filtration, aliquot, and store at −20 C.
3. 100 mg/ml Rifampicin stock: Prepare by dissolving powder in DMSO, aliquot, and store at −20 C.
4. 300 mg/ml Timentin stock: Prepare by dissolving powder in water and sterilize by filtration, aliquot, and store at −20 C.
5. 2.0 mg/ml NAA stock: Prepare by dissolving powder in 1N NaOH, adjust volume with water and sterilize by filtration, aliquot, and store at −20 C.
6. 2.0 mg/ml BAP stock: Prepare by dissolving powder in 1N NaOH, adjust volume with water and sterilize by filtration, aliquot, and store at −20 C.
7. 5 mg/ml AgNO3 stock: Prepare by dissolving powder in water and sterilize by filtration, and store at +4 C.
8. 1.0 mg/ml Zeatin stock: Prepare by dissolving powder in 1N NaOH, adjust volume with water and sterilize by filtration, aliquot, and store at −20 C.
9. All the chemicals used for media are added to autoclaved medium once it has cooled to about 50 C. Swirl to mix thoroughly the medium before pouring into 90×25-mm Petri dishes.

Characterization of Regenerated Transgenic Plants

The T-DNA comprising the expression construct included the nptII gene, which confers resistance to paromycin. Six plantlets (AM1 to AM6) were identified as resistant to paromomycin, suggesting that these plants were transformed with the expression construct. Polymerase chain reaction on genomic DNA isolated from these plantlets using primers specific for the hairpin expression construct (SEQ ID NO: 9, TAACCGACTTGCTGCCCCGA; SEQ ID NO: 10, AAATAGAGATGCTTGCAGAAGATCCCG) showed that plants AM1, AM2 and AM3 contain amplicon from genomic DNA. Primers for actin (SEQ ID NO: 11, CGTTTGAATCT-TGCTGGCCGTGAT; SEQ ID NO: 12, TAGACGAGCT-GCCTTTGGAAGTGT) were used as a positive control to confirm that the samples contained genomic DNA from *Papaver somniferum*.

Figure 4:
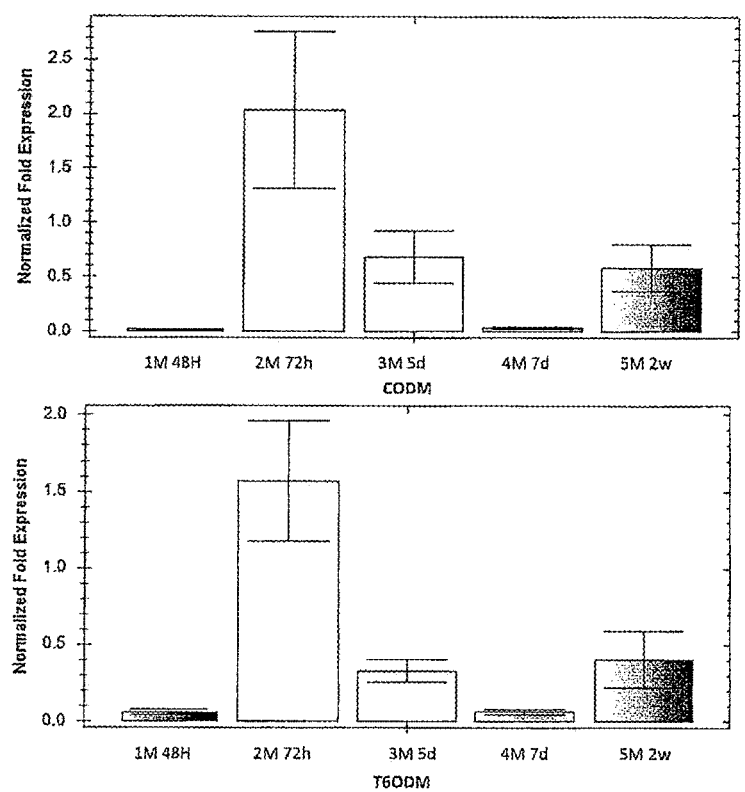
FIG. 4 are histograms showing the expression of the endogenous genes encoding CODM and T6ODM after transient expression of the expression construct.

Referring to FIG. 4 reverse transcription polymerase chain reaction (RT-PCR) was performed on RNA extracts from plants AM1 to AM6 was performed using primers specific for the hairpin (SEQ ID NO: 9, TAACCGACTT-GCTGCCCCGA; SEQ ID NO: 10, AAATAGAGATGCTT-GCAGAAGATCCCG), and demonstrated that the expression construct was expressed in plants AM1, AM2, and AM3.

Figure 5:
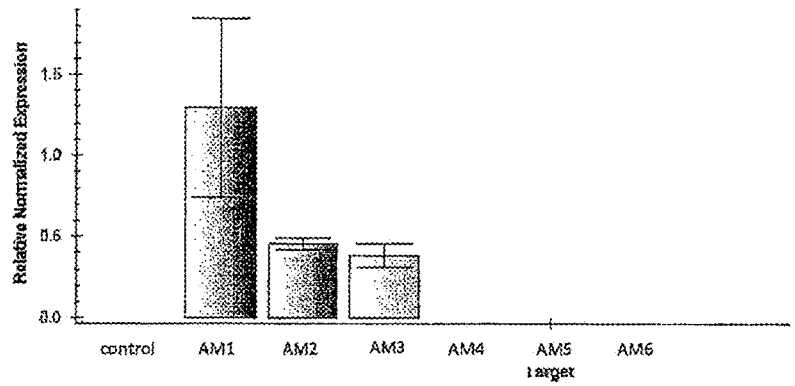
FIG. 5 is a histogram showing expression of the expression construct in transgenic lines AM1, AM2, and AM3.
Figure 6A:
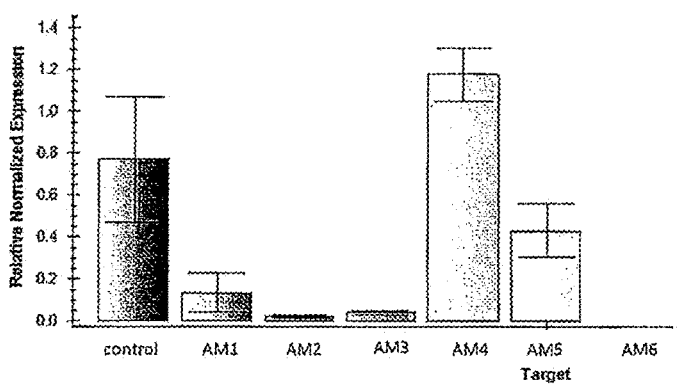
FIGS. 6 A-B are histograms showing reduced expression of the endogenous genes encoding T6ODM in FIG. 6A and CODM in FIG. 6B, in lines AM1, AM2, and AM3.
Figure 6B:
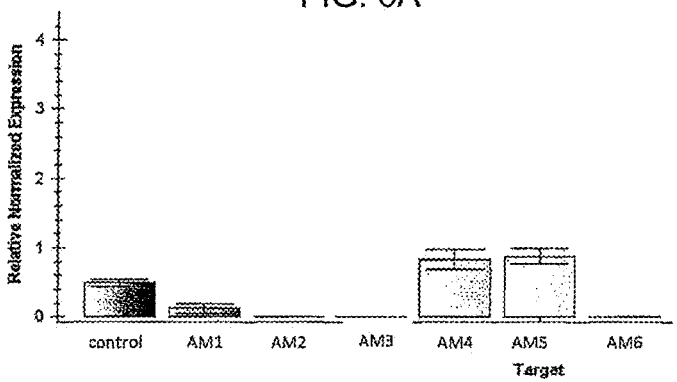
Figure 7A:
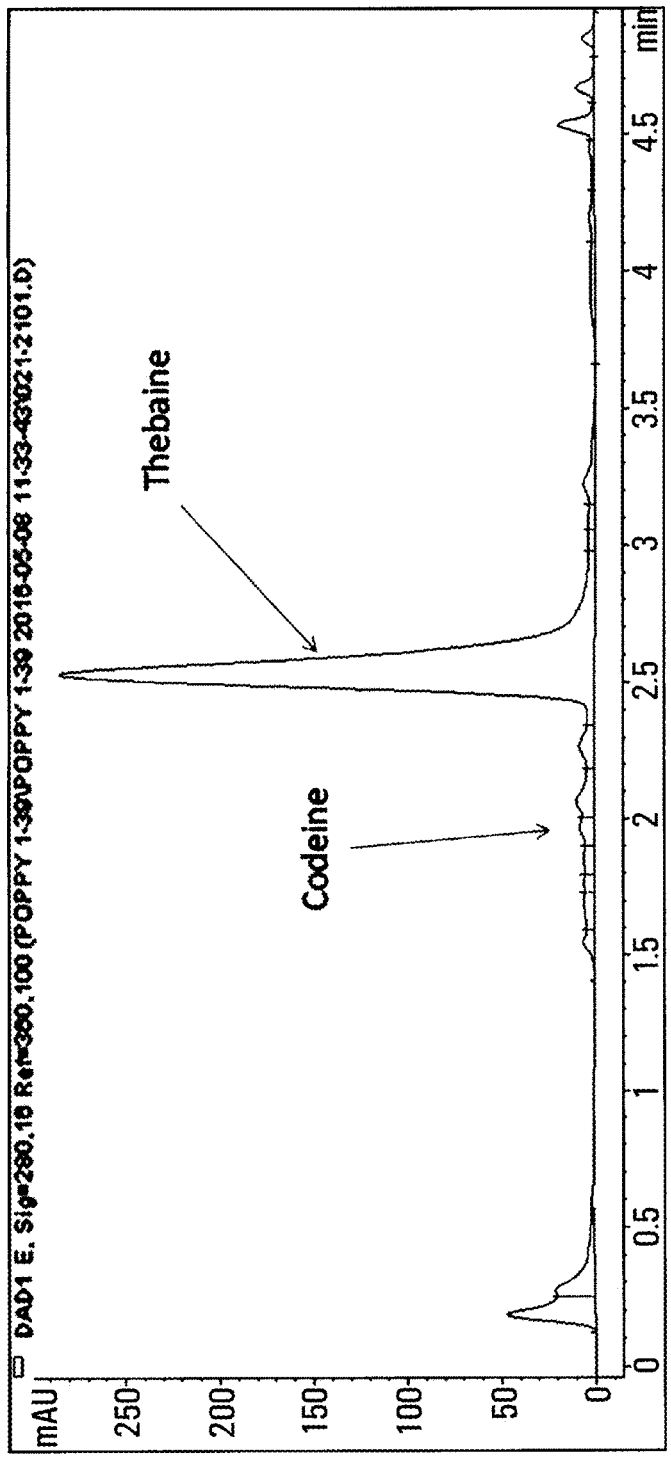
FIGS. 7A-D are chromatographs showing the accumulation of thebaine in lines AM1 in FIG. 7A, AM2 in FIG. 7B, and AM3 in FIG. 7C, relative to line AM10 in FIG. 7D that does not have the expression construct.
Figure 7B:
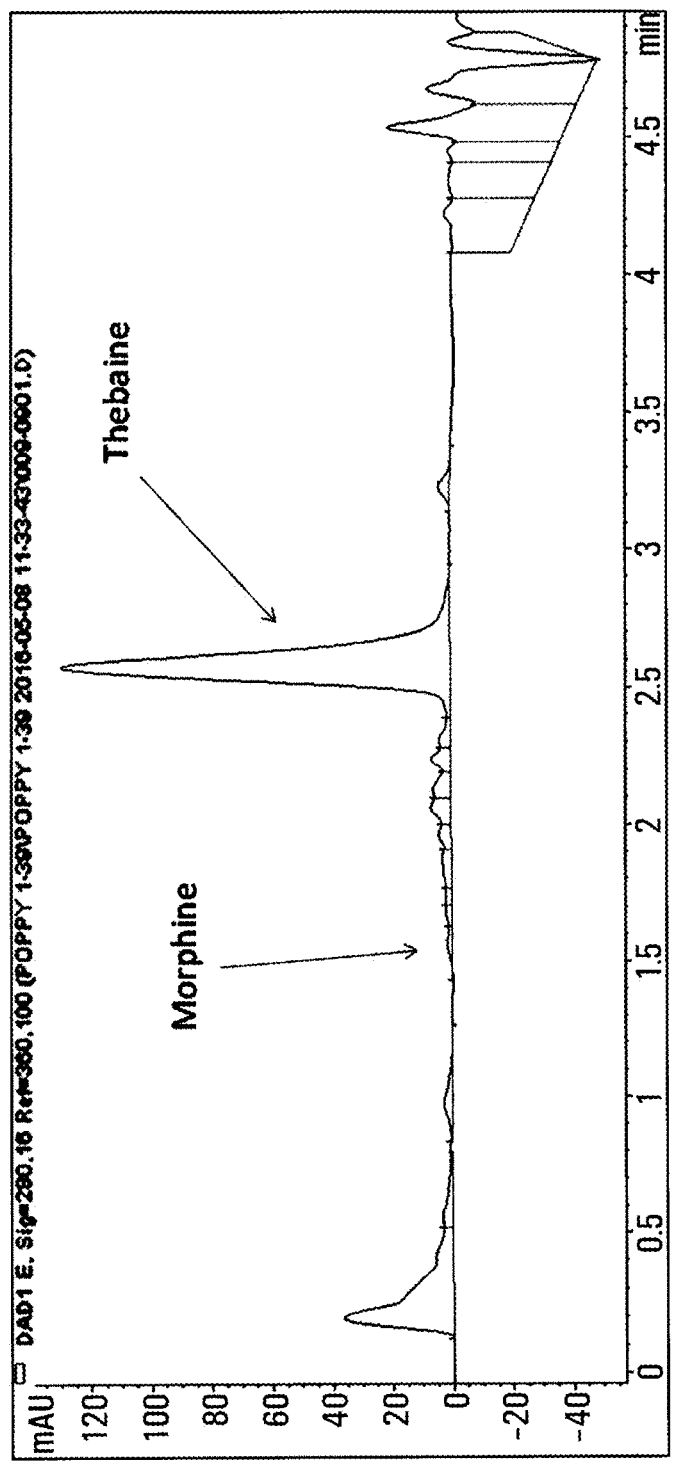
Figure 7C:
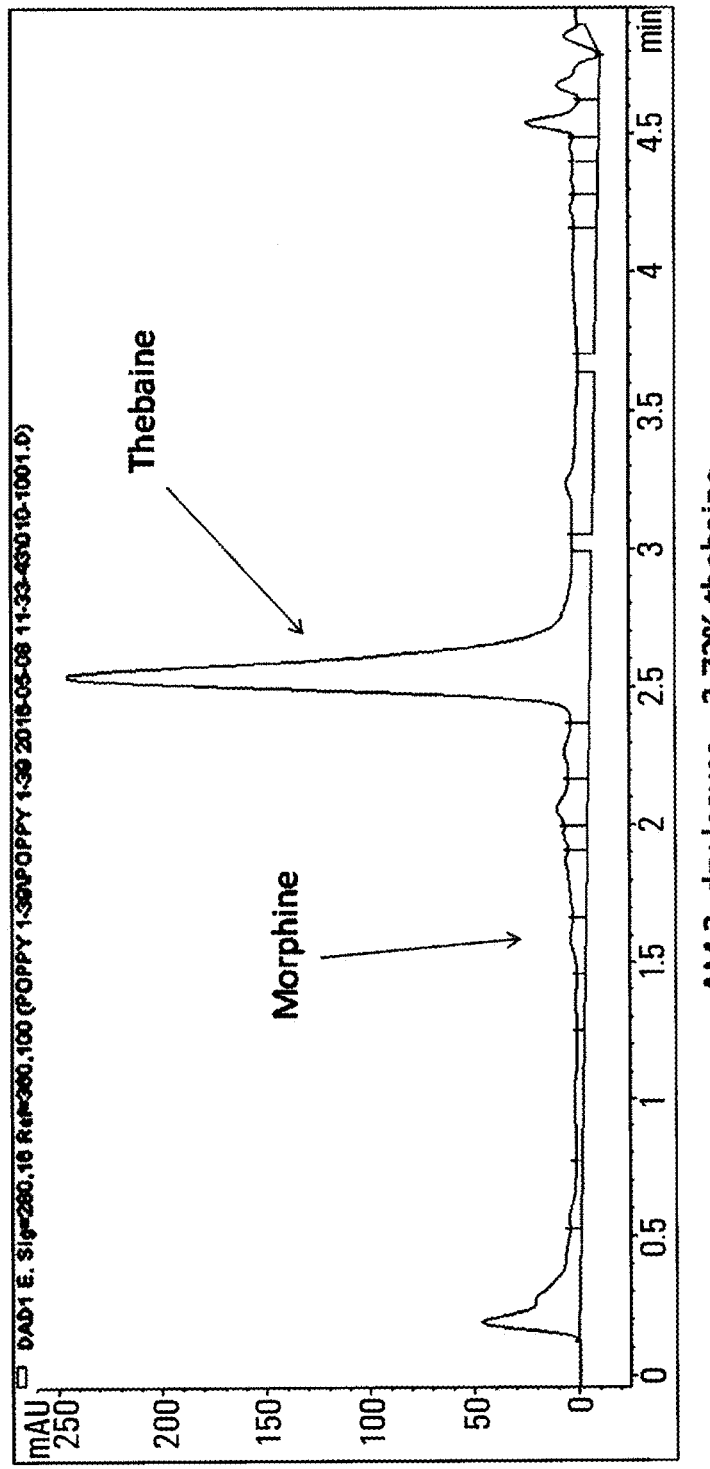
Figure 7D:
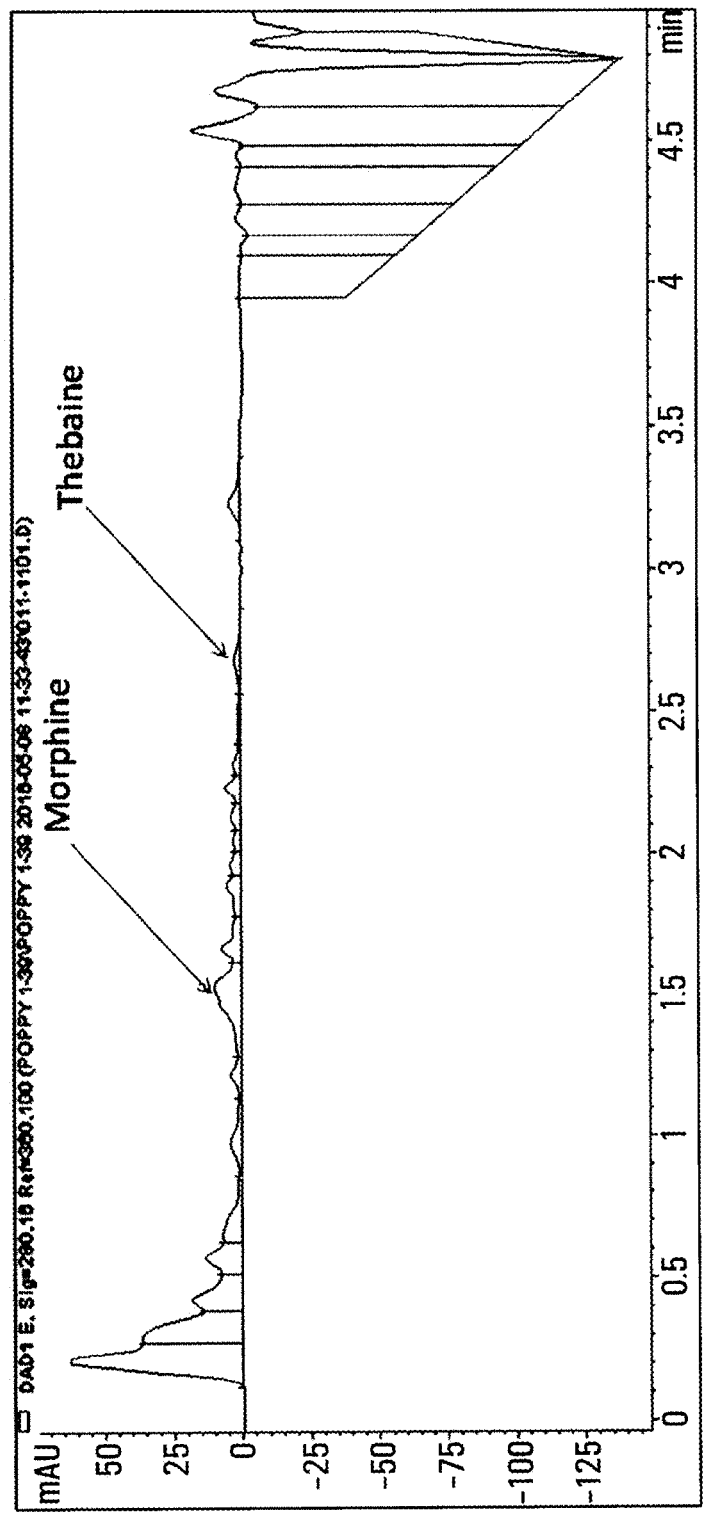

RT-PCR was performed on the RNA extracts from plants AM1 to AM6 using primers specific for endogenous transcripts encoding CODM and T6ODM. Referring to FIG. 5, expression of the expression construct appeared sufficient to downregulate the expression of the endogenous gene encoding T6ODM relative to plants that did not express the expression construct. Referring to FIG. 6, expression of the expression construct appeared sufficient to downregulate the expression of the endogenous gene encoding CODM relative to plants that did not express the expression construct.

Alkaloid Analysis

Acidic extraction: 0.100 g of ground capsule or stems (from poppy) was mixed with 5 ml of a solution of 10% acetic acid, 10% water and 80% methanol followed by agitation for 30 minutes, and then filtered. The filtrate was directly injected into the HPLC.

All samples were run on an HPLC Gradient System having an Kinetex 2.6 um C18, 50×2.1 mm column, with a 2 microliter injection volume, operating at 280 nm at a temperature of 45° C. and a flow rate of 0.8 ml/min. Eluent A was 10 mM Ammonium acetate Buffer, pH 5.5, whereas Eluent B was Acetonitrile (100%). The gradient profile is as follows

| Step No. | Time (min) | Pct A | Pct B |
|---|---|---|---|
| 1 | 0 | 95 | 5 |
| 2 | 0.25 | 85 | 15 |
| 3 | 2.00 | 60 | 40 |
| 4 | 2.01 | 95 | 5 |
| 5 | 3.00 | 20 | 80 |
| 6 | 4.00 | 10 | 90 |
| 7 | 5.00 | 0 | 100 |

The reported figures are percent by weight of the dry starting material.

Referring to FIGS. 7A to 7D, analysis of alkaloids in the capsule of AM 1 and the leaves of AM2 and AM3 indicated increased accumulation of thebaine and decreased accumulation of morphine compared to a plant in which the expression construct was not present and had a wild type level of T6ODM and CODM expression. Subsequent analysis of alkaloids in the capsules of the AM2 and AM3 plants showed that thebaine accumulated to 4.82% of alkaloids in the AM2 capsules and to 3.13% of total alkaloids in the AM3 capsules. Substantially no morphine was detected in AM1, AM2, and AM3 plants.

TABLE 1

Concentration of alkaloids in transgenic plants per 100 mg dry capsule.

|  | Codeine (Conc. wt %) | Thebaine (Conc. wt %) |
|---|---|---|
| AM1 | 0.23 | 3.87 |
| AM2 | 0.11 | 4.82 |
| AM3 | 0.12 | 3.13 |

The progeny of the self-fertilized AM1, AM2, and AM3 transformants appear to segregate 3:1, indicating that the transgenes are stably integrated and inherited.

Six additional individual transformants that carry the expression construct, and in which the endogenous CODM and T6ODM transcripts could not be detected, were isolated (AM12, AM13, AM16, AM17, and AM19). Analysis in the capsules of these additional plants showed that thebaine accumulated to as much as 8.28% of alkaloids in the capsules (see Table 2).

TABLE 2

Concentration of thebaine in transgenic plants per 100 mg dry capsule.

| | Thebaine (Conc. wt %) |
|---|---|
| AM12 | 5.87 |
| AM13 | 6.20 |
| AM16 | 8.28 |
| AM17 | 7.18 |
| AM19 | 4.95 |

Plants were grown from progeny seed of AM1 that contained the expression construct. The concentration of morphine, oripavine, codeine, and morphine in poppy straw from six AM1 progeny carrying the expression construct are provided in Table 3.

TABLE 3

Concentration of thebaine, codeine, oripavine, and morphine in poppy straw of progeny of AM1.

| | Amount of Each Component (% w/w) | | | |
|---|---|---|---|---|
| Individual | Morphine | Oripavine | Codeine | Thebaine |
| AM1-1 | 0.07 | 0.01 | 0.09 | 4.94 |
| AM1-13 | 0.05 | 0.20 | 0.10 | 4.46 |
| AM1-28 | 0.10 | 0.01 | 0.08 | 3.69 |
| AM1-30 | 0.07 | 0.02 | 0.14 | 6.68 |
| AM1-38 | 0.05 | 0.01 | 0.07 | 3.20 |
| AM1-82 | 0.06 | 0.03 | 0.13 | 5.31 |

Operation

While specific embodiments of the invention have been described and illustrated, such embodiments should be considered illustrative of the invention only and not as limiting the invention as construed in accordance with the accompanying claims.

This description contains a sequence listing in electronic form in ASCII text format. The sequences in the sequence listing are reproduced in the following Table.

```
Sequence Table
SEQ ID NO: 1 (T6ODM)
Met Glu Lys Ala Lys Leu Met Lys Leu Gly Asn Gly Met Glu Ile Pro
1               5                   10                  15

Ser Val Gln Glu Leu Ala Lys Leu Thr Leu Ala Glu Ile Pro Ser Arg
                20                  25                  30

Tyr Val Cys Ala Asn Glu Asn Leu Leu Leu Pro Met Gly Ala Ser Val
            35                  40                  45

Ile Asn Asp His Glu Thr Ile Pro Val Ile Asp Ile Glu Asn Leu Leu
        50                  55                  60

Ser Pro Glu Pro Ile Ile Gly Lys Leu Glu Leu Asp Arg Leu His Phe
65                  70                  75                  80

Ala Cys Lys Glu Trp Gly Phe Phe Gln Val Val Asn His Gly Val Asp
                85                  90                  95

Ala Ser Leu Val Asp Ser Val Lys Ser Glu Ile Gln Gly Phe Phe Asn
            100                 105                 110

Leu Ser Met Asp Glu Lys Thr Lys Tyr Glu Gln Glu Asp Gly Asp Val
        115                 120                 125

Glu Gly Phe Gly Gln Gly Phe Ile Glu Ser Glu Asp Gln Thr Leu Asp
    130                 135                 140

Trp Ala Asp Ile Phe Met Met Phe Thr Leu Pro Leu His Leu Arg Lys
145                 150                 155                 160

Pro His Leu Phe Ser Lys Leu Pro Val Pro Leu Arg Glu Thr Ile Glu
                165                 170                 175

Ser Tyr Ser Ser Glu Met Lys Lys Leu Ser Met Val Leu Phe Asn Lys
            180                 185                 190

Met Glu Lys Ala Leu Gln Val Gln Ala Ala Glu Ile Lys Gly Met Ser
        195                 200                 205

Glu Val Phe Ile Asp Gly Thr Gln Ala Met Arg Met Asn Tyr Tyr Pro
    210                 215                 220

Pro Cys Pro Gln Pro Asn Leu Ala Ile Gly Leu Thr Ser His Ser Asp
225                 230                 235                 240

Phe Gly Gly Leu Thr Ile Leu Leu Gln Ile Asn Glu Val Glu Gly Leu
                245                 250                 255

Gln Ile Lys Arg Glu Gly Thr Trp Ile Ser Val Lys Pro Leu Pro Asn
            260                 265                 270
```

```
Ala Phe Val Val Asn Val Gly Asp Ile Leu Glu Ile Met Thr Asn Gly
            275                 280                 285

Ile Tyr His Ser Val Asp His Arg Ala Val Val Asn Ser Thr Asn Glu
290                 295                 300

Arg Leu Ser Ile Ala Thr Phe His Asp Pro Ser Leu Glu Ser Val Ile
305                 310                 315                 320

Gly Pro Ile Ser Ser Leu Ile Thr Pro Glu Thr Pro Ala Leu Phe Lys
            325                 330                 335

Ser Gly Ser Thr Tyr Gly Asp Leu Val Glu Glu Cys Lys Thr Arg Lys
            340                 345                 350

Leu Asp Gly Lys Ser Phe Leu Asp Ser Met Arg Ile
            355                 360
```

SEQ ID NO: 2 (T6ODM)
```
gttcttaatt cattaattaa tttagaaaaa tcatggagaa agcaaaactt atgaagctag     60
gtaatggtat ggaaatacca gtgttcaag aattggctaa actcacgctt gccgaaattc    120
catctcgata cgtatgcgcc aatgaaaacc ttttgttgcc tatgggtgca tctgtcataa   180
atgatcatga aaccattcct gtcatcgata tagaaaattt attatctcca gaaccaataa   240
tcggaaagtt agaattagat aggcttcatt ttgcttgcaa agaatggggt ttttttcagg   300
tagtgaacca tggagtcgac gcttcattgg tggatagtgt aaaatcagaa attcaaggtt   360
tctttaacct ttctatggat gagaaaacta aatatgaaca ggaagatgga gatgtggaag   420
gatttggaca aggctttatt gaatcagagg accaaacact tgattgggca gatatattta   480
tgatgttcac tcttccactc catttaagga agcctcactt attttcaaaa ctcccagtgc   540
ctctcaggga gacaatcgaa tcctactcat cagaaatgaa aaagttatcc atggttctct   600
ttaataagat ggaaaaagct ctacaagtac aagcagccga gattaagggt atgtcagagg   660
tgtttataga tgggacacaa gcaatgagga tgaactatta tcccccttgt cctcaaccaa   720
atctcgccat cggtcttacg tcgcactcgg attttggcgg tttgacaatc ctccttcaaa   780
tcaacgaagt ggaaggatta cagataaaaa gagaggggac atggatttca gtcaaacctc   840
tacctaatgc gttcgtagtg aatgttggag atattttgga gataatgact aatggaattt   900
accatagtgt cgatcaccgg gcagtagtaa actcaacaaa tgagaggctc tcaatcgcaa   960
catttcatga ccctagtcta gagtcggtaa taggcccaat atcaagcttg attactccag  1020
agacacctgc tttgtttaaa agtggatcta catatgggga tcttgtggag gaatgtaaaa  1080
caaggaagct cgatggaaaa tcatttcttg actccatgag gatttgaaaa ctcaagaaaa  1140
aataatacga cgtgattgca tgtcagattc aactatcctt ttgtcgtttt ttggtgctcg  1200
agtcctttaat tgttttgatc attgcttttg attctaatta ataagacttt tctcaagaac  1260
cacatgtaat gtacctttac tttcagaaaa taaaaagtat tgaggcacaa atgagaaaat  1320
tgagagagtg cttgagaagt gtaatttctc gaaagtgcgt tgtgtttgaa aaaaaaaaa   1380
aaaaaa                                                             1386
```

SEQ ID NO: 3 (CODM)
```
Met Glu Thr Pro Ile Leu Ile Lys Leu Gly Asn Gly Leu Ser Ile Pro
1               5                   10                  15

Ser Val Gln Glu Leu Ala Lys Leu Thr Leu Ala Glu Ile Pro Ser Arg
            20                  25                  30

Tyr Thr Cys Thr Gly Glu Ser Pro Leu Asn Asn Ile Gly Ala Ser Val
            35                  40                  45

Thr Asp Asp Glu Thr Val Pro Val Ile Asp Leu Gln Asn Leu Leu Ser
50                  55                  60
```

```
Pro Glu Pro Val Val Gly Lys Leu Glu Leu Asp Lys Leu His Ser Ala
 65                  70                  75                  80

Cys Lys Glu Trp Gly Phe Phe Gln Leu Val Asn His Gly Val Asp Ala
             85                  90                  95

Leu Leu Met Asp Asn Ile Lys Ser Glu Ile Lys Gly Phe Phe Asn Leu
            100                 105                 110

Pro Met Asn Glu Lys Thr Lys Tyr Gly Gln Gln Asp Gly Asp Phe Glu
        115                 120                 125

Gly Phe Gly Gln Pro Tyr Ile Glu Ser Glu Asp Gln Arg Leu Asp Trp
    130                 135                 140

Thr Glu Val Phe Ser Met Leu Ser Leu Pro Leu His Leu Arg Lys Pro
145                 150                 155                 160

His Leu Phe Pro Glu Leu Pro Leu Pro Phe Arg Glu Thr Leu Glu Ser
                165                 170                 175

Tyr Leu Ser Lys Met Lys Lys Leu Ser Thr Val Val Phe Glu Met Leu
            180                 185                 190

Glu Lys Ser Leu Gln Leu Val Glu Ile Lys Gly Met Thr Asp Leu Phe
        195                 200                 205

Glu Asp Gly Leu Gln Thr Met Arg Met Asn Tyr Tyr Pro Pro Cys Pro
    210                 215                 220

Arg Pro Glu Leu Val Leu Gly Leu Thr Ser His Ser Asp Phe Ser Gly
225                 230                 235                 240

Leu Thr Ile Leu Leu Gln Leu Asn Glu Val Glu Gly Leu Gln Ile Arg
                245                 250                 255

Lys Glu Glu Arg Trp Ile Ser Ile Lys Pro Leu Pro Asp Ala Phe Ile
            260                 265                 270

Val Asn Val Gly Asp Ile Leu Glu Ile Met Thr Asn Gly Ile Tyr Arg
        275                 280                 285

Ser Val Glu His Arg Ala Val Val Asn Ser Thr Lys Glu Arg Leu Ser
    290                 295                 300

Ile Ala Thr Phe His Asp Ser Lys Leu Glu Ser Glu Ile Gly Pro Ile
305                 310                 315                 320

Ser Ser Leu Val Thr Pro Glu Thr Pro Ala Leu Phe Lys Arg Gly Arg
                325                 330                 335

Tyr Glu Asp Ile Leu Lys Glu Asn Leu Ser Arg Lys Leu Asp Gly Lys
            340                 345                 350

Ser Phe Leu Asp Tyr Met Arg Met
            355                 360

SEQ ID NO: 4 (CODM)
gtaaagattg atatatgatc tgaagatctg acaagaaagt tcatcaaata tagagttcat    60
ggagacacca atacttatca agctaggcaa tggtttgtca ataccaagtg ttcaggaatt   120
ggctaaactc acgcttgcag aaattccatc tcgatacaca tgcaccggtg aaagcccgtt   180
gaataatatt ggtgcgtctg taacagatga tgaaacagtt cctgtcatcg atttgcaaaa   240
tttactatct ccagaacccg tagttggaaa gttagaattg ataagcttc attctgcttg    300 caaagaatgg ggtttctttc agctggttaa ccatggagtc gacgctttac tgatggacaa   360
tataaaatca gaaattaaag gtttctttaa ccttccaatg aatgagaaaa ctaaatacgg   420
acagcaagat ggagattttg aaggatttgg acaaccctat attgaatcgg aggaccaaag   480
acttgattgg actgaagtgt ttagcatgtt aagtcttcct ctccatttaa ggaagcctca   540
tttgtttcca gaactccctc tgcctttcag ggagacactg gaatcctacc tatcaaaaat   600
gaaaaaacta tcaacggttg tctttgagat gttggaaaaa tctctacaat tagttgagat   660
taaaggtatg acagacttat ttgaagatgg gttgcaaaca atgaggatga actattatcc   720
```

-continued

```
tccttgtcct cgaccagagc ttgtacttgg tcttacgtca cactcggatt ttagcggttt    780
gacaattctc cttcaactta atgaagttga aggattacaa ataagaaaag aagagaggtg    840
gatttcaatc aaacctctac ctgatgcgtt catagtgaat gttggagaca ttttggagat    900
aatgactaat gggatttacc gtagcgtcga gcaccgggca gtagtaaact caacaaagga    960
gaggctctca atcgcgacat ttcatgactc taaactagag tcagaaatag gcccaatttc   1020
gagcttggtc acaccagaga cacctgcttt gttcaaaaga ggtaggtatg aggatatttt   1080
gaaggaaaat ctttcaagga agcttgatgg aaaatcattt ctcgactaca tgaggatgtg   1140
agaaagtgtg aacatatatt atactccaca ttgtgtttaa tatatgatga ataagttgc    1200 ttttgaagta tgatgaaata agttggtttt gaagaattca tattgtgctt aaatttcgtg   1260
gatgactgag agatttatta tgtaataata atgtattggt ttgaagattc tcgtctcact   1320
atatgtaaga ctctgtttgg gtcaagtgat gtaatcacgg ttgaaataag ttgcttttga   1380
agaattcata tggtgcttaa tattatgtaa taaataatgt attggattga aaaaaaaaa    1440 aaaaaaaaa aa                                                       1452
```

SEQ ID NO: 5

```
tcctgtggttggcatgcacatacaaatggacgaacggataaaccttttcacgccctttta aatatccgattattct aataaacgctcttttctcttaggtttacccgccaatatatcctgtcaaacactgatagtt taaactgaaggcggga aacgacaatctgctagtggatctcccagtcacgacgttgtaaaacgggcgccccgcggaa agcttgctagccaatt ggggcccaacgttctcgagaacgtggatacttggcagtggttacttggcttttccttta ttttcttttggacggaa gcggtggttactttgtcacacatttaaaaaaaacacgtgtttctcacttttttctattcc cgtcacaaacaattta agaaagatccatctatcgtgatctttctatcaaacaaagaaaaaaggtcttcatagtaac gctacaacatcaaat atgtggttgctctgacatcagtcgggaaataaggatatggcggcattggccacatctatt ggggtcccaacttcc tttcacaaaaaattaaattgggtgtcccaacttttatctttgatatagtgacatgagta tcgggagcattggaca atggataaaatgagaactaaaaaaattctggttaattttttgatcattgttatttaaaagg ttatttatctataat ctacccatattgatcagttttatttaaatttgtttagctaccgctccacgagagagat cctcatcttaaaaatgga atatggaaattacacacgaccccaaaagtatattttttctctggagaatgctatttagag ctttgactatatggtc tgaattagaaagacgggaaataaaatctgctaagtgatataagctctaagtaggcgatgt gtgatggagaacacct tttctttaacagtcttcatgttttacagattcgcgaacttcgaatatccctatacggtct gtctaaccctcgtgtg tcttttgagtccaagataaaggccattattgagtaacatagacatgctggaatccaacca ttgaagtcacaactgt ccatgtagattctttggagaatctgaaaagtcttaataaaggtggtgtttcaaagaaaa caaaacaaatgagttaa gaaaaaaaaatatcatgtagtggtcgagtattatgttatttattgtgtagctaccaatct ttattctttaaatctg acataaaatgctacaaactttttacctcgtctatagccccaaaaaaacctaaccacggtt ctaaaaccacacacagt gattttggttgacgacaatgcctctccttcctcaaaacgatttattttacatttttaa atcaaatgttacattta taccataattaagtcttttttacagaatacttagatggaagagatgtataaaaaggagga aattgtaaaaaacata tttcgatcaattaaaccaggattcataaaaatataagtatatatataaatgatgtttcgt ttagcgatgaacttca ctcatatgataatacttaacaatataagtacataaaaaataaaataaaattaattgtttac gaaaagtctacaaat actgcatgtataattaatgttctctttatttatttatttataccttaccaagatatatct ataaccgcatagaaat agaaggcgaagagataaatttccaaaaacaagaaaaacctctaagctcaaaagtctagaag gccttggatccaccca tggaggttgtcacagtatcacttgtagcagttgtgatcactactttcttatacttaatct tcagagattcaagtcc taaaggtttgccaccaggtccaaaaccctggccaatagttggaaaccttcttcaacttgg tgagaaacctcattct cagtttgctcagcttgctgaaacctatggtgatctcttttcactgaaactaggaagtgaa acggttgttgtagctt caactccattagcagctagcgagattctaaagacgcatgatcgtgttctctctggtcgat acgtgtttcaaagttt
```

-continued ccgggtaaaggaacatgtggagaactctattgtgtggtctgaatgtaatgaaacatggaagaaactgcggaaagtt tgtagaacggaacttttttacgcagaagatgattgaaagtcaagctgaagttagagaaagtaaggctatggaaatgg tggagtatttgaagaaaaatgtaggaaatgaagtgaaaattgctgaagttgtatttgggacgttggtgaatatatt cggtaacttgatattttcacaaaatattttcaagttgggtgatgaaagtagtggaagtgtagaaatgaaagaacat ctatggagaatgctggaattggggaactcgacaaatccagctgattattttccattttgggtaaattcgatttgt ttggacaaagaaaagatgttgctgattgtctgcaagggatttatagtgtttgggtgctatgctcaaagaaagaaa aatagccaagcagcataacaacagcaagaagaatgattttgttgagattttgctcgattccggactcgatgaccag cagattaatgccttgctcatggaaatatttggtgcgggaacagagacaagtgcatctacaatagaatgggcgttgt ctgagctcacaaaaaaccctcaagtaacagccaatatgcggttggaattgttatctgtggtagggaagaggccggt taaggaatccgacataccaaacatgccttatcttcaagcttttgttaaagaaactctacggcttcatccagcaact cctctgctgcttccacgtcgagcacttgagacctgcaaagttttgaactatacgatcccgaaagagtgtcagatta tggtgaacgcctggggcattggtcgggatccaaaaaggtggactgatccattgaagttttcaccagagaggttctt gaattcgagcattgatttcaaagggaacgacttcgagttgataccatttggtgcagggagaaggatatgtcctggt gtgcccttggcaactcaatttattagtcttattgtgtctagtttggtacagaattttgattggggattaccgaagg gaatggatcctagccaactgatcatggaagagaaatttgggtgacactgcaaaaggaaccacctctgtatattgtt cctaaaactcgggattaagggagaattcgtcgactttgcggccgcatcgatactgcaggagctcggtaccttttac tagtgatatccctgtgtgaaattgttatccgctacgcgtgatcgttcaaacatttggcaataaagtttcttaagat tgaatcctgttgccggtcttgcgatgattatcatataaatttctgttgaattacgttaagcatgtaataattaacat gtaatgcatgacgttatttatgagatgggtttttatgattagagtcccgcaattatacatttaatacgcgatagaa aacaaaatatagcgcgcaaactaggataaattatcgcgcgcggtgtcatctatgttactagatcccatgggaagtt cctattccgaagttcctattctctgaaagtataggaact<u>tcagcgatcgctccaatcccacaaaaatctgagctt</u>

<u>aacagcacagttgctcctctcagagcagaatcgggtattcaacaccctcatatcaactactacgttgtgtataacg</u>

<u>gtccacatgccggtatatacgatgactggggttgtacaaaggcggcaacaaacggcgttcccggagttgcacacaa</u>

<u>gaaatttgccactattacagaggcaagagcagcagctgacgcgtacacaacaagtcagcaaacagacaggttgaac</u>

<u>ttcatcccaaaggagaagctcaactcaagcccaagagctttgctaaggccctaacaagcccaccaaagcaaaaag</u>

<u>cccactggctcacgctaggaaccaaaaggcccagcagtgatccagccccaaaagagactcctttgccccggagatt</u>

<u>acaatggacgatttcctctatctttacgatctaggaaggaagttcgaaggtgaaggtgacgacactatgttcacca</u>

<u>ctgataatgagaaggttagcctcttcaatttcagaaagaatgctgacccacagatggttagagaggcctacgcagc</u>

<u>aggtctcatcaagacgatctacccgagtaacaatctccaggagatcaaataccttcccaagaaggttaaagatgca</u>

<u>gtcaaaagattcaggactaattgcatcaagaacacagagaaagacatatttctcaagatcagaagtactattccag</u>

<u>tatggacgattcaaggcttgcttcataaaccaaggcaagtaatagagattggagtctctaaaaaggtagttcctac</u>

<u>tgaatctaaggccatgcatggagtctaagattcaaatcgaggatctaacagaactcgccgtgaagactggcgaaca</u>

<u>gttcatacagagtcttttacgactcaatgacaagaagaaaatcttcgtcaacatggtggagcacgacactctggtc</u>

<u>tactccaaaaatgtcaaagatacagtctcagaagaccaaagggctattgagacttttcaacaaaggataaatttcgg</u>

<u>gaaacctcctcggattccattgcccagctatctgtcacttcatcgaaaggacagtagaaaaggaaggtggctccta</u>

<u>caaatgccatcattgcgataaaggaaaggctatcattcaagatctctctgccgacagtggtcccaaagatggaccc</u>

<u>ccacccacgaggagcatcgtggaaaaagaagacgttccaaccacgtcttcaaagcaagtggattgatgtgacatct</u>

<u>ccactgacgtaagggatgacgcacaatcccactatccttcgcaagacccttcctctatataaggaagttcatttca</u>

<u>tttggagaggacacgctcgagtataagagctctattttacaacaattaccaacaacaacaaacaacaaacaacat</u>

<u>tacaattacatttacaattaccatggggcgcgcccttgtcctcaaccaaatctcgccatcggtcttacgtcgcac</u>

<u>tcggattttggcggtttgacaatcctccttcaaatcaacgaagtggaaggattacagataaaaagagagggacat</u>

-continued

```
ggatttcagtcaaacctctacctaatgcgttcgtagtgaatgttggagatattttggagataatgactaatggaat ttaccatagtgtcgatcaccgggcagtagtaaactcaacaaatgagaggctctcaatcgcaacatttcatgaccct agtctagagtcggtaataggcccaatatcaagcttgattactccagagacacctgctttgtttaaaagtggaattt aaatccccagatgaacatggcatcgtggtgattgatgaaactgctgctgtcggctttaacctctctttaggcattg gtttcgaagcgggcaacaagccgaaagaactgtacagcgaagaggcagtcaacggggaaactcagcaagcgcactt acaggcgattaaagagctgatagcgcgtgacaaaaaccacccaagcgtggtgatgtggagtattgccaacgaaccg gatacccgtccgcaaggtgcacgggaatatttcgcgccactggcggaagcaacgcgtaaactcgacccgacgcgtc cgatcacctgcgtcaatgtaatgttctgcgacgctcacaccgataccatcagcgatctctttgatgggatcctcc acttttaaacaaagcaggtgtctctggagtaatcaagcttgatattgggcctattaccgactctagactagggtca tgaaatgttgcgattgagagcctctcatttgttgagtttactactgcccggtgatcgacactatggtaaattccat tagtcattatctccaaaatatctccaacattcactacgaacgcattaggtagaggtttgactgaaatccatgtccc ctctcttttatctgtaatccttccacttcgttgatttgaaggaggattgtcaaaccgccaaaatccgagtgcgac gtaagaccgatggcgagatttggttgaggacaaggactagtccctagagtcctgctttaatgagatatgcgagacg cctatgatcgcatgatatttgctttcaattctgttgtgcacgttgtaaaaaacctgagcatgtgtagctcagatcc ttaccgccggtttcggttcattctaatgaatgaatatatcacccgttactatcgtatttttatgaataatattctc cgttcaatttactgattgtaccctactacttatatgtacaatattaaaatgaaaacaatatattgtgctgaatagg tttatagcgacatctatgatagagcgccacaataacaaacaattgcgttttattattacaaatccaattttaaaaa aagcggcagaaccggtcaaacctaaaagactgattacataaatcttattcaaatttcaaaagtgcccagggcta gtatctacgacacaccgagcggcgaactaataacgctcactgaagggaactccggttccccgccggcgcgcatggg tgagattccttgaagttgagtattggccgtccgctctaccgaaagttacgggcaccattcaacccggtccagcacg gcggccgggtaaccgacttgctgccccgagaattatgcagcattttttggtgtatgtgggcccaaatgaagtgc aggtcaaaccttgacagtgacgacaaatcgttgggcgggtccagggcgaattttgcgacaacatgtcgaggctcag cagggcgatcgcagacgtcgggatcttctgcaagcatctctatttcctgaaggtctaacctcgaagatttaagatt taattacgtttataattacaaaattgattctagtatctttaatttaatgcttatacattattaattaatttagtac tttcaatttgttttcagaaattatttactattttttataaaataaaagggagaaaatggctatttaaatactagc ctattttatttcaattttagcttaaaatcagccccaattagccccaatttcaaattcaaatggtccagcccaattc ctaaataacccaccctaacccgccggtttccccttttgatccatgcagtcaacgcccagaatttccctatataa tttttttaattcccaaacacccctaactctatcccatttctcaccaaccgccacatagatctatcctcttatctctc aaactctctcgaaccttcccctaaccctagcagcctctcatcatcctcacctcaaaacccaccggggccggccatg attgaacaagatggattgcacgcaggttctccggccgcttgggtggagaggctattcggctatgactgggcacaac agacaatcggctgctctgatgccgccgtgttccggctgtcagcgcaggggaggccggttcttttttgtcaagaccga cctgtccggtgccctgaatgaacttcaagacgaggcagcgcggctatcgtggctggccacgacgggcgttccttgc gcagctgtgctcgacgttgtcactgaagcgggaagggactggctgctattgggcgaagtgccggggcaggatctcc tgtcatctcaccttgctcctgccgagaaagtatccatcatggctgatgcaatgcggcggctgcatacgcttgatcc ggctacctgcccattcgaccaccaagcgaaacatcgcatcgagcgagcacgtactcggatggaagccggtcttgtc gatcaggatgatctggacgaagagcatcaggggctcgcgccagccgaactgttcgccaggctcaaggcgcgcatgc ccgacggcgaggatctcgtcgtgactcatggcgatgcctgcttgccgaatatcatggtggaaaatggccgcttttc tggattcatcgactgtggccggctgggtgtggcggaccgctatcaggacatagcgttggctacccgtgatattgct gaagagcttggcggcgaatgggctgaccgcttcctcgtgctttacggtatcgccgctcccgattcgcagcgcatcg ccttctatcgccttcttgacgagttcttctgaggcgcgccgatcgttcaaacatttggcaataaagtttcttaaga ttgaatcctgttgccggtcttgcgatgattatcatataatttctgttgaattacgttaagcatgtaataattaaca
```

-continued tgtaatgcatgacgttatttatgagatgggttttatgattagagtcccgcaattatacatttaatacgcgataga
aaacaaaatatagcgcgcaaactaggataaattatcgcgcgcggtgtcatctatgttactagatccctagggaagt
tcctattccgaagttcctattctctgaaaagtataggaacttctttgcgtattgggcgctcttggccttttggcc
accggtcgtacggttaaaaccaccccagtacattaaaaacgtccgcaatgtgttattaagttgtctaagcgtcaat
ttgtttacaccacaatatatcctgccaccagccagccaacagctccccgaccggcagctcggcacaaaatcaccac
tcgatacaggcagcccatcagtcc

SEQ ID NO: 6 gcgatcgctccaatcccacaaaaatctgagcttaacagcacagttgctcctctcagagcagaatcgggtattcaac
accctcatatcaactactacgttgtgtataacggtccacatgccggtatatacgatgactggggttgtacaaaggc
ggcaacaaacggcgttcccggagttgcacacaagaaatttgccactattacagaggcaagagcagcagctgacgcg
tacacaacaagtcagcaaacagacaggttgaacttcatccccaaaggagaagctcaactcaagcccaagagctttg
ctaaggccctaacaagcccaccaaagcaaaaagcccactggctcacgctaggaaccaaaaggcccagcagtgatcc
agcccccaaaagagactcctttgccccggagattacaatggacgatttcctctatctttacgatctaggaaggaagt
tcgaaggtgaaggtgacgacactatgttcaccactgataatgagaaggttagcctcttcaatttcagaaagaatgc
tgacccacagatggttagagaggcctacgcagcaggtctcatcaagacgatctacccgagtaacaatctccaggag
atcaaataccttcccaagaaggttaaagatgcagtcaaaagattcaggactaattgcatcaagaacacagagaaag
acatatttctcaagatcagaagtactattccagtatggacgattcaaggcttgcttcataaaccaaggcaagtaat
agagattggagtctctaaaaaggtagttcctactgaatctaaggccatgcatggagtctaagattcaaatcgagga
tctaacagaactcgccgtgaagactggcgaacagttcatacagagtcttttacgactcaatgacaagaagaaaatc
ttcgtcaacatggtggagcacgacactctggtctactccaaaaatgtcaaagatacagtctcagaagaccaaaggg
ctattgagacttttcaacaaaggataatttcgggaaacctcctcggattccattgcccagctatctgtcacttcat
cgaaaggacagtagaaaaggaaggtggctcctacaaatgccatcattgcgataaaggaaaggctatcattcaagat
ctctctgccgacagtggtcccaaagatggaccccacccacgaggagcatcgtggaaaaagaagacgttccaacca
cgtcttcaaagcaagtggattgatgtgacatctccactgacgtaagggatgacgcacaatcccactatccttcgca
agacccttcctctatataaggaagttcatttcatttggagaggacacgctcgagtataagagctctattttacaa
caattaccaacaacaacaaacaacaaacaacattacaattacatttacaattaccatggggcgcg<u>cccccttgtcct</u>
<u>caaccaaatctcgccatcggtcttacgtcgcactcggattttggcggtttgacaatcctccttcaaatcaacgaag</u>
<u>tggaaggattacagataaaaagagaggggacatggatttcagtcaaacctctacctaatgcgttcgtagtgaatgt</u>
<u>tggagatattttggagataatgactaatggaatttaccatagtgtcgatcaccgggcagtagtaaactcaacaaat</u>
<u>gagaggctctcaatcgcaacatttcatgaccctagtctagagtcggtaataggcccaatatcaagcttgattactc</u>
<u>cagagacacctgctttgtttaaaagtggaatttaaatccccagatgaacatggcatcgtggtgattgatgaaactg</u>
ctgctgtcggctttaacctctcttaggcattggtttcgaagcgggcaacaagccgaaagaactgtacagcgaaga
ggcagtcaacggggaaactcagcaagcgcacttacaggcgattaaagagctgatagcgcgtgacaaaaaccaccca
agcgtggtgatgtggagtattgccaacgaaccggatacccgtccgcaaggtgcacgggaatatttcgcgccactgg
cggaagcaacgcgtaaactcgacccgacgcgtccgatcacctgcgtcaatgtaatgttctgcgacgctcacaccga
taccatcagcgatctctttgatgggga<u>tctccacttttaaacaaagcaggtgtctctggagtaatcaagcttgat</u>
<u>attgggcctattaccgactctagactagggtcatgaaatgttgcgattgagagcctctcatttgttgagtttacta</u>
<u>ctgcccggtgatcgacactatggtaaattccattagtcattatctccaaaatatctccaacattcactacgaacgc</u>
<u>attaggtagaggtttgactgaaatccatgtcccctctcttttttatctgtaatccttccacttcgttgatttgaagg</u>
<u>aggattgtcaaaccgccaaaatccgagtgcgacgtaagaccgatggcgagatttggttgaggacaaggactagtcc</u>
ctagagtcctgctttaatgagatatgcgagacgcctatgatcgcatgatatttgctttcaattctgttgtgcacgt -continued tgtaaaaaacctgagcatgtgtagctcagatccttaccgccggtttcggttcattctaatgaatgaatatatcacc
cgttactatcgtatttttatgaataatattctccgttcaatttactgattgtaccctactacttatatgtacaata
ttaaaatgaaaacaatatattgtgctgaataggtttatagcgacatctatgatagagcgccacaataacaaacaat
tgcgttttattattacaaatccaattttaaaaaaagcggcagaaccggtcaaacctaaaagactgattacataaat
cttattcaaatttcaaaagtgccccaggggctagtatctacgacacaccgagcggcgaactaataacgctcactga
agggaactccggttccccgccggcgcgcatgggtgagattccttgaagttgagtattggccgtccgctctaccgaa
agttacgggcaccattcaacccggtccagcacggcggccgggtaaccgacttgctgccccgagaattatgcagcat
ttttttggtgtatgtgggccccaaatgaagtgcaggtcaaaccttgacagtgacgacaaatcgttgggcgggtcca
gggcgaattttgcgacaacatgtcgaggctcagcagggcgatcgca SEQ ID NO: 7
<u>cccctttgtcctcaaccaaatctcgccatcggtcttacgtcgcactcggattttggcggtttgacaatcctccttca</u>
<u>aatcaacgaagtggaaggattacagataaaaagagagggacatggatttcagtcaaacctctacctaatgcgttc</u>
<u>gtagtgaatgttggagatattttggagataatgactaatggaatttaccatagtgtcgatcaccgggcagtagtaa</u>
<u>actcaacaaatgagaggctctcaatcgcaacatttcatgaccctagtctagagtcggtaataggcccaatatcaag</u>
<u>cttgattactccagagacacctgctttgtttaaaagtgga</u>atttaaatccccagatgaacatggcatcgtggtgat
tgatgaaactgctgctgtcggctttaacctctctttaggcattggtttcgaagcgggcaacaagccgaaagaactg
tacagcgaagaggcagtcaacggggaaactcagcaagcgcacttacaggcgattaaagagctgatagcgcgtgaca
aaaccacccaagcgtggtgatgtggagtattgccaacgaaccggatacccgtccgcaaggtgcacgggaatattt
cgcgccactggcggaagcaacgcgtaaactcgacccgacgcgtccgatcacctgcgtcaatgtaatgttctgcgac
gctcacaccgataccatcagcgatctctttgatggggatc<u>ctccacttttaaacaaagcaggtgtctctggagtaa</u>
<u>tcaagcttgatattgggcctattaccgactctagactagggtcatgaaatgttgcgattgagagcctctcatttgt</u>
<u>tgagtttactactgcccggtgatcgacactatggtaaattccattagtcattatctccaaaatatctccaacattc</u>
<u>actacgaacgcattaggtagaggtttgactgaaatccatgtcccctctcttttatctgtaatccttccacttcgt</u>
<u>tgatttgaaggaggattgtcaaaccgccaaaatccgagtgcgacgtaagaccgatggcgagatttggttgaggaca</u>
<u>agg</u>

SEQ ID NO: 8
ccttgtcctcaaccaaatctcgccatcggtcttacgtcgcactcggattttggcggtttgacaatcctccttcaaa
tcaacgaagtggaaggattacagataaaaagagaggggacatggatttcagtcaaacctctacctaatgcgttcgt
agtgaatgttggagatattttggagataatgactaatggaatttaccatagtgtcgatcaccgggcagtagtaaac
tcaacaaatgagaggctctcaatcgcaacatttcatgaccctagtctagagtcggtaataggcccaatatcaagct
tgattactccagagacacctgctttgtttaaaagtgga

SEQ ID NO: 9
TAACCGACTTGCTGCCCCGA

SEQ ID NO: 10
AAATAGAGATGCTTGCAGAAGATCCCG

SEQ ID NO: 11
CGTTTGAATCTTGCTGGCCGTGAT

SEQ ID NO: 12
TAGACGAGCTGCCTTTGGAAGTGT

SEQ ID NO: 13:
CGTCTTGCGCACTGATTTGAA

SEQ ID NO 14:
CGTTTGAATCTTGCTGGCCGTGAT

-continued

SEQ ID NO: 15 (T6ODM)
```
guucuuaauu cauuaauuaa uuuagaaaaa ucauggagaa agcaaaacuu augaagcuag      60
guaaugguau ggaaauacca aguguucaag aauuggcuaa acucacgcuu gccgaaauuc     120
caucucgaua cguaugcgcc aaugaaaacc uuuuguugcc uaugggugca ucugucauaa     180
augaucauga aaccauuccu gucaucgaua uagaaaauuu auuaucucca gaaccaauaa     240
ucggaaaguu agaauuagau aggcuucauu uugcuugcaa agaaugggguu uuuuucagg     300
uagugaacca uggagucgac gcuucauugg uggauagugu aaaaucagaa auucaagguu     360
ucuuuaaccu uucuauggau gagaaaacua aauaugaaca ggaagaugga gaugguggaag    420
gauuuggaca aggcuuuauu gaaucagagg accaaacacu ugauugggca gauauauuua    480
ugauguucac ucuuccacuc cauuuaagga agccuacacuu auuucaaaa cucccagugc    540
cucucaggga gacaaucgaa uccuacucau cagaaaugaa aaaguuaucc augguucucu    600
uuaauaagau ggaaaaagcu cuacaaguac aagcagccga gauuaagggu augucagagg    660
uguuuauaga ugggacacaa gcaaugagga ugaacuauua uccccccuugu ccucaaccaa    720
aucucgccau cggucuuacg ucgcacucgg auuuuggcgg uuugacaauc ucccuucaaa    780
ucaacgaagu ggaaggauua cagauaaaaa gagaggggac auggauuuca gucaaaccuc    840
uaccuaaugc guucguagug aauguuggag auauuuugga gauaaugacu aauggaauuu    900
accauagugu cgaucaccgg gcaguaguaa acucaacaaa ugagaggcuc ucaaucgcaa    960
cauuucauga cccuagucua gagucgguaa uaggcccaau aucaagcuug auuacuccag   1020
agacaccugc uuuguuuaaa aguggaucua cauauggggga ucuuguggag gaauguaaaa   1080
caaggaagcu cgauggaaaa ucauucuug acuccaugag gauuugaaaa ucaagaaaaa   1140
aauaauacga cgugauugca ugucagauuc aacuauccuu uugucguuuu uggugcucg   1200
aguccuuaau uguuugauc auugcuuuug auucaauua auaagacuuu ucucaagaac   1260
cacauguaau guaccuuuac uuucagaaaa uaaaaaguau ugaggcacaa augaaaaau   1320
ugagagagug cuugagaagu guaauuucuc gaaagugcgu ugguguugaa aaaaaaaaa   1380
aaaaaa                                                             1386
```
SEQ ID NO: 16 (CODM)
```
guaaagauug auauaugauc ugaagaucug acaagaaagu caucaaauua uagaguucau      60
ggagacacca auacuuauca agcuaggcaa uggguuuguca auaccaagug uucaggaauu    120
ggcuaaacuc acgcuugcag aaauuccauc ucgauacaca ugcaccggug aaagcccguu    180
gaauaauauu ggugcgucug uaacagauga ugaaacaguu ccugucaucg auuugcaaaa    240
uuuacuaucu ccagaacccg uaguuggaaa guuagaauug auaagcuuc auucugcuug    300
caaagaaugg gguuucuuuc agcugguuaa ccaggagucu gacgcuuuac ugauggacaa    360
uauaaaauca gaaauuaaag guuucuuuaa ccuuccaaug aaugagaaaa cuaaauacgg    420
acagcaagau ggagauuuug aaggauuugg acaacccuau auugaaucgg aggaccaaag    480
acuugauugg acgaagugu uuagcauguu aagucuuccu cuccauuuaa ggaagccuca    540
uuuguuccaa gaacucccuc ugccuuucag ggagacacug gaauccuacc uaucaaaaau    600
gaaaaaacua ucaacgguug ucuuugagau guugaaaaa ucucuacaau aguugagau     660
uaaagguaug acagcuuuau uugaagaugg guugcaaaca augaggauga acuauuuacc    720
uccuugccu cgaccagagc uuguacuugg ucuuacguca cacucggauu uuagcgguuu    780
gacaauucuc cuucaacuua augaaguuga aggauuacaa auaagaaaag aagagaggug    840
gauuucaauc aaaccucuac cugaugcguu cauagugaau guuggagaca uuuggagau    900
aaugacuaau gggauuuacc uagcgucga gcaccgggca guauaaaacu caacaaagga    960
```

```
gaggcucuca aucgcgacau uucaugacuc uaaacuagag ucagaaauag gcccaauuuc    1020
gagcuugguc acaccagaga caccugcuuu guucaaaaga gguagguaug aggauauuuu    1080
gaaggaaaau cuuucaagga agcuugaugg aaaaucauuu cucgacuaca ugaggaugug    1140
agaaagugug aacauauauu auacuccaca uuguguuuaa uauaugauga aauaaguugc    1200
uuuugaagua ugaugaaaua aguggguuuu gaagaauuca uauugugcuu aaauuucgug    1260
gaugacugag agauuauua uguaauaaua auguauggu uugaagauuc ucgucucacu      1320
auauguaaga cucuguuugg gucaagugau guaaucacgg uugaaauaag uugcuuuuga    1380
agaauucaua uggugcuuaa uauuauguaa uaauaaugu auuggauuga aaaaaaaaaa     1440
aaaaaaaaaa aa                                                         1452
```

---

What is claimed is:

1. A method of increasing accumulation of thebaine in an opium poppy plant, the method comprising genetically modifying the genome of the plant to include a nucleic acid molecule encoding a hairpin RNA for simultaneous reducing the activity of thebaine 6-O-demethylase (T6ODM) and codeine 3-O-demethylase (CODM) in the poppy plant, wherein the nucleic acid molecule comprises SEQ ID NO: 7.

2. The method of claim 1, wherein T6ODM has an amino acid sequence at least 95% identical to the amino acid sequence of SEQ ID NO: 1.

3. A genetically modified opium poppy plant having reduced activity of thebaine 6-O-demethylase (T6ODM) and codeine 3-O-demethylase (CODM) relative to a wild type plant, wherein the genetically modified opium poppy plant comprises a nucleic acid molecule encoding a hairpin RNA for simultaneously reducing the activity of thebaine 6-O-demethylase (T6ODM) and codeine 3-O-demethylase (CODM) in the poppy plant, wherein the nucleic acid molecule comprises SEQ ID 7.

4. An isolated nucleic acid molecule, wherein the sequence of the nucleic acid molecule comprises SEQ ID NO:7.

5. An expression vector for simultaneously reducing the expression of endogenous genes encoding thebaine 6-O-demethylase (T6ODM) and codeine 3-O-demethylase (CODM) in an opium poppy plant, the expression vector comprising an isolated nucleic acid as defined in claim 4.

6. Poppy straw from a plant as defined in claim 3.

7. Latex from a plant as defined in claim 3.

8. The method of claim 1, wherein CODM has an amino acid sequence at least 95% identical to the amino acid sequence of SEQ ID NO: 3.

9. The method of claim 1, wherein T6ODM has an amino acid sequence at least 95% identical to the amino acid sequence of SEQ ID NO: 1 and CODM has an amino acid sequence at least 95% identical to the amino acid sequence of SEQ ID NO: 3.

10. The method of claim 1, wherein simultaneously reducing the activity of T6ODM and CODM comprises reducing the accumulation of transcripts from an endogenous gene encoding T6ODM and an endogenous gene encoding CODM.

11. The method of claim 10, wherein the endogenous gene encoding T6ODM encodes an mRNA comprising a nucleic acid sequence at least 95% identical to the sequence of SEQ ID NO: 15.

12. The method of claim 10, wherein the endogenous gene encoding CODM encodes an mRNA comprising a nucleic acid sequence at least 95% identical to the sequence of SEQ ID NO: 16.

13. The plant of claim 3, wherein simultaneously reducing the activity of T6ODM and CODM comprises reducing the accumulation of transcripts from an endogenous gene encoding T6ODM and an endogenous gene encoding CODM.

14. The plant of claim 13, wherein the endogenous gene encoding CODM encodes an mRNA comprising a nucleic acid sequence at least 95% identical to the sequence of SEQ ID NO: 16.

15. The plant of claim 13, wherein the endogenous gene encoding T6ODM encodes an mRNA comprising a nucleic acid sequence at least 95% identical to the sequence of SEQ ID NO: 15.

16. The plant of claim 13, wherein the endogenous gene encoding CODM encodes a polypeptide comprising an amino acid sequence at least 95% identical to the sequence of SEQ ID NO 3.

17. The plant of claim 13, wherein the endogenous gene encoding T6ODM encodes a polypeptide of of SEQ ID NO: 1 and the endogenous gene encoding CODM encodes a polypeptide comprising an amino acid sequence at least 95% identical of SEQ ID NO: 3.

18. The plant of claim 13, wherein the endogenous gene encoding T6ODM encodes an mRNA comprising a nucleic acid sequence at least 95% identical to the sequence of SEQ ID NO: 15 and the endogenous gene encoding CODM encodes an mRNA comprising a nucleic acid sequence at least 95% identical to the sequence of SEQ ID NO: 16.

19. The plant of claim 13, wherein the endogenous gene encoding T6ODM encodes a polypeptide having an amino acid sequence at least 95% identical to the sequence of SEQ ID NO: 1.

20. The expression vector of claim 5, wherein the endogenous gene encoding T6ODM encodes a polypeptide of SEQ ID NO: 1 and the endogenous gene encoding CODM encodes a polypeptide comprising an amino acid sequence at least 95% identical of SEQ ID NO: 3.

* * * * *

SEQUENCE LISTING

<160> NUMBER OF SEQ ID NOS: 16

<210> SEQ ID NO 1
<211> LENGTH: 364
<212> TYPE: PRT
<213> ORGANISM: Papaver somniferum T6ODM

<400> SEQUENCE: 1

```
Met Glu Lys Ala Lys Leu Met Lys Leu Gly Asn Gly Met Glu Ile Pro
1               5                   10                  15

Ser Val Gln Glu Leu Ala Lys Leu Thr Leu Ala Glu Ile Pro Ser Arg
            20                  25                  30

Tyr Val Cys Ala Asn Glu Asn Leu Leu Leu Pro Met Gly Ala Ser Val
        35                  40                  45

Ile Asn Asp His Glu Thr Ile Pro Val Ile Asp Ile Glu Asn Leu Leu
    50                  55                  60

Ser Pro Glu Pro Ile Ile Gly Lys Leu Glu Leu Asp Arg Leu His Phe
65                  70                  75                  80

Ala Cys Lys Glu Trp Gly Phe Phe Gln Val Val Asn His Gly Val Asp
                85                  90                  95

Ala Ser Leu Val Asp Ser Val Lys Ser Glu Ile Gln Gly Phe Phe Asn
            100                 105                 110

Leu Ser Met Asp Glu Lys Thr Lys Tyr Glu Gln Glu Asp Gly Asp Val
        115                 120                 125

Glu Gly Phe Gly Gln Gly Phe Ile Glu Ser Glu Asp Gln Thr Leu Asp
    130                 135                 140

Trp Ala Asp Ile Phe Met Met Phe Thr Leu Pro Leu His Leu Arg Lys
145                 150                 155                 160

Pro His Leu Phe Ser Lys Leu Pro Val Pro Leu Arg Glu Thr Ile Glu
                165                 170                 175

Ser Tyr Ser Ser Glu Met Lys Lys Leu Ser Met Val Leu Phe Asn Lys
            180                 185                 190

Met Glu Lys Ala Leu Gln Val Gln Ala Ala Glu Ile Lys Gly Met Ser
        195                 200                 205

Glu Val Phe Ile Asp Gly Thr Gln Ala Met Arg Met Asn Tyr Tyr Pro
    210                 215                 220

Pro Cys Pro Gln Pro Asn Leu Ala Ile Gly Leu Thr Ser His Ser Asp
225                 230                 235                 240

Phe Gly Gly Leu Thr Ile Leu Leu Gln Ile Asn Glu Val Glu Gly Leu
                245                 250                 255
```

```
Gln Ile Lys Arg Glu Gly Thr Trp Ile Ser Val Lys Pro Leu Pro Asn
            260                 265                 270

Ala Phe Val Val Asn Val Gly Asp Ile Leu Glu Ile Met Thr Asn Gly
        275                 280                 285

Ile Tyr His Ser Val Asp His Arg Ala Val Val Asn Ser Thr Asn Glu
    290                 295                 300

Arg Leu Ser Ile Ala Thr Phe His Asp Pro Ser Leu Glu Ser Val Ile
305                 310                 315                 320

Gly Pro Ile Ser Ser Leu Ile Thr Pro Glu Thr Pro Ala Leu Phe Lys
                325                 330                 335

Ser Gly Ser Thr Tyr Gly Asp Leu Val Glu Glu Cys Lys Thr Arg Lys
            340                 345                 350

Leu Asp Gly Lys Ser Phe Leu Asp Ser Met Arg Ile
            355                 360

<210> SEQ ID NO 2
<211> LENGTH: 1386
<212> TYPE: DNA
<213> ORGANISM: Papaver somniferum T6ODM

<400> SEQUENCE: 2
gttcttaatt cattaattaa tttagaaaaa tcatggagaa agcaaaactt atgaagctag     60
gtaatggtat ggaaatacca agtgttcaag aattggctaa actcacgctt gccgaaattc    120
catctcgata cgtatgcgcc aatgaaaacc ttttgttgcc tatgggtgca tctgtcataa    180
atgatcatga aaccattcct gtcatcgata tagaaaattt attatctcca gaaccaataa    240
tcggaaagtt agaattagat aggcttcatt ttgcttgcaa agaatggggt ttttttcagg    300
tagtgaacca tggagtcgac gcttcattgg tggatagtgt aaaatcagaa attcaaggtt    360
tctttaacct ttctatggat gagaaaacta aatatgaaca ggaagatgga gatgtggaag    420
gatttggaca aggcttttat tgaatcagagg accaaacact tgattgggca gatatattta    480
tgatgttcac tcttccactc catttaagga agcctcactt attttcaaaa ctcccagtgc    540
ctctcaggga gacaatcgaa tcctactcat cagaaatgaa aaagttatcc atggttctct    600
ttaataagat ggaaaaagct ctacaagtac aagcagccga gattaagggt atgtcagagg    660
tgtttataga tgggacacaa gcaatgagga tgaactatta tccccccttgt cctcaaccaa    720 atctcgccat cggtcttacg tcgcactcgg attttggcgg tttgacaatc ctccttcaaa    780
tcaacgaagt ggaaggatta cagataaaaa gagagggggac atggatttca gtcaaacctc    840
tacctaatgc gttcgtagtg aatgttggag atattttgga gataatgact aatggaattt    900
accatagtgt cgatcaccgg gcagtagtaa actcaacaaa tgagaggctc tcaatcgcaa    960
catttcatga ccctagtcta gagtcggtaa taggcccaat atcaagcttg attactccag   1020
agacacctgc tttgttttaaa agtggatcta catatgggga tcttgtggag gaatgtaaaa   1080
caaggaagct cgatggaaaa tcatttcttg actccatgag gatttgaaaa ctcaagaaaa   1140
aataatacga cgtgattgca tgtcagattc aactatcctt ttgtcgttttt ttggtgctcg   1200 agtccttaat tgtttttgatc attgctttttg attctaatta ataagacttt tctcaagaac   1260
cacatgtaat gtacctttac tttcagaaaa taaaaagtat tgaggcacaa atgagaaaat   1320
tgagagagtg cttgagaagt gtaatttctc gaaagtgcgt tgtgtttgaa aaaaaaaaaaa   1380 aaaaaa                                                              1386
```

```
<210> SEQ ID NO 3
<211> LENGTH: 360
<212> TYPE: PRT
<213> ORGANISM: Papaver somniferum CODM

<400> SEQUENCE: 3

Met Glu Thr Pro Ile Leu Ile Lys Leu Gly Asn Gly Leu Ser Ile Pro
1               5                   10                  15

Ser Val Gln Glu Leu Ala Lys Leu Thr Leu Ala Glu Ile Pro Ser Arg
            20                  25                  30

Tyr Thr Cys Thr Gly Glu Ser Pro Leu Asn Asn Ile Gly Ala Ser Val
        35                  40                  45

Thr Asp Asp Glu Thr Val Pro Val Ile Asp Leu Gln Asn Leu Leu Ser
    50                  55                  60

Pro Glu Pro Val Val Gly Lys Leu Glu Leu Asp Lys Leu His Ser Ala
65                  70                  75                  80

Cys Lys Glu Trp Gly Phe Phe Gln Leu Val Asn His Gly Val Asp Ala
                85                  90                  95

Leu Leu Met Asp Asn Ile Lys Ser Glu Ile Lys Gly Phe Phe Asn Leu
            100                 105                 110

Pro Met Asn Glu Lys Thr Lys Tyr Gly Gln Gln Asp Gly Asp Phe Glu
        115                 120                 125

Gly Phe Gly Gln Pro Tyr Ile Glu Ser Glu Asp Gln Arg Leu Asp Trp
    130                 135                 140

Thr Glu Val Phe Ser Met Leu Ser Leu Pro Leu His Leu Arg Lys Pro
145                 150                 155                 160

His Leu Phe Pro Glu Leu Pro Leu Pro Phe Arg Glu Thr Leu Glu Ser
                165                 170                 175

Tyr Leu Ser Lys Met Lys Lys Leu Ser Thr Val Val Phe Glu Met Leu
            180                 185                 190

Glu Lys Ser Leu Gln Leu Val Glu Ile Lys Gly Met Thr Asp Leu Phe
        195                 200                 205

Glu Asp Gly Leu Gln Thr Met Arg Met Asn Tyr Tyr Pro Pro Cys Pro
    210                 215                 220

Arg Pro Glu Leu Val Leu Gly Leu Thr Ser His Ser Asp Phe Ser Gly
225                 230                 235                 240

Leu Thr Ile Leu Leu Gln Leu Asn Glu Val Glu Gly Leu Gln Ile Arg
                245                 250                 255

Lys Glu Glu Arg Trp Ile Ser Ile Lys Pro Leu Pro Asp Ala Phe Ile
            260                 265                 270

Val Asn Val Gly Asp Ile Leu Glu Ile Met Thr Asn Gly Ile Tyr Arg
        275                 280                 285

Ser Val Glu His Arg Ala Val Asn Ser Thr Lys Glu Arg Leu Ser
    290                 295                 300

Ile Ala Thr Phe His Asp Ser Lys Leu Glu Ser Glu Ile Gly Pro Ile
305                 310                 315                 320

Ser Ser Leu Val Thr Pro Glu Thr Pro Ala Leu Phe Lys Arg Gly Arg
                325                 330                 335

Tyr Glu Asp Ile Leu Lys Glu Asn Leu Ser Arg Lys Leu Asp Gly Lys
            340                 345                 350

Ser Phe Leu Asp Tyr Met Arg Met
        355                 360
```

```
<210> SEQ ID NO 4
<211> LENGTH: 1452
<212> TYPE: DNA
<213> ORGANISM: Papaver somniferum CODM

<400> SEQUENCE: 4
gtaaagattg atatatgatc tgaagatctg acaagaaagt tcatcaaata tagagttcat      60
ggagacacca atacttatca agctaggcaa tggtttgtca ataccaagtg ttcaggaatt     120
ggctaaactc acgcttgcag aaattccatc tcgatacaca tgcaccggtg aaagcccgtt     180
gaataatatt ggtgcgtctg taacagatga tgaaacagtt cctgtcatcg atttgcaaaa     240
tttactatct ccagaacccg tagttggaaa gttagaattg ataagcttc attctgcttg      300
caaagaatgg ggtttctttc agctggttaa ccatggagtc gacgctttac tgatggacaa     360
tataaaatca gaaattaaag gtttctttaa ccttccaatg aatgagaaaa ctaaatacgg     420
acagcaagat ggagattttg aaggatttgg acaaccctat attgaatcgg aggaccaaag     480
acttgattgg actgaagtgt ttagcatgtt aagtcttcct ctccatttaa ggaagcctca     540
tttgtttcca gaactccctc tgcctttcag ggagacactg gaatcctacc tatcaaaaat     600
gaaaaaacta tcaacggttg tctttgagat gttggaaaaa tctctacaat tagttgagat     660
taaaggtatg acagacttat ttgaagatgg gttgcaaaca atgaggatga actattatcc     720
tccttgtcct cgaccagagc ttgtacttgg tcttacgtca cactcggatt ttagcggttt     780
gacaattctc cttcaactta tgaagttga aggattacaa ataagaaaag aagagaggtg     840
gatttcaatc aaacctctac ctgatgcgtt catagtgaat gttggagaca ttttggagat     900
aatgactaat gggatttacc gtagcgtcga gcaccgggca gtagtaaact caacaaagga     960
gaggctctca atcgcgacat ttcatgactc taaactagag tcagaaatag cccaatttc     1020
gagcttggtc acaccagaga cacctgcttt gttcaaaaga ggtaggtatg aggatatttt    1080
gaaggaaaat ctttcaagga agcttgatgg aaaatcattt ctcgactaca tgaggatgtg    1140
agaaagtgtg aacatatatt atactccaca ttgtgtttaa tatatgatga aataagttgc    1200
ttttgaagta tgatgaaata agttggtttt gaagaattca tattgtgctt aaatttcgtg    1260
gatgactgag agatttatta tgtaataata atgtattggt ttgaagattc tcgtctcact    1320
atatgtaaga ctctgtttgg gtcaagtgat gtaatcacgg ttgaaataag ttgcttttga    1380
agaattcata tggtgcttaa tattatgtaa taaataatgt attggattga aaaaaaaaa    1440
aaaaaaaaaa aa                                                       1452

<210> SEQ ID NO 5
<211> LENGTH: 8688
<212> TYPE: DNA
<213> ORGANISM: Artificial Sequence
<220> FEATURE:
<223> OTHER INFORMATION: TDNA sequence

<400> SEQUENCE: 5
tcctgtggtt ggcatgcaca tacaaatgga cgaacggata aaccttttca cgcccttta       60
aatatccgat tattctaata aacgctcttt tctcttaggt ttacccgcca atatatcctg     120
tcaaacactg atagtttaaa ctgaaggcgg gaaacgacaa tctgctagtg gatctcccag     180
tcacgacgtt gtaaaacggg cgccccgcgg aaagcttgct agccaattgg ggcccaacgt     240
tctcgagaac gtggatactt ggcagtggtt acttggcttt ccttattt ctttttggac       300
ggaagcggtg gttactttgt cacacattta aaaaaacacg tgtttctcac tttttctat     360
```

```
tcccgtcaca aacaatttta agaaagatcc atctatcgtg atctttctat caaacaaaag    420
aaaaaaggtc ttcatagtaa cgctacaaca tcaaatatgt ggttgctctg acatcagtcg    480
ggaaaataag gatatggcgg cattggccac atctattggg gtcccaactt cctttcacaa    540
aaaaattaaa ttgggtgtcc caacttttat ctttgatata gtgacatgag tatcgggagc    600
attggacaat ggataaaatg agaactaaaa aaattctggt taattttga tcattgttat     660 ttaaaaggtt atttatcta taatctaccc atattgatca gttttattta aatttgttta    720
gctaccgctc cacgagagag atcctcatct taaaaatgga atatggaaat tacacacgac    780
cccaaaagta tattttttct ctggagaatg ctatttagag ctttgactat atggtctgaa    840
ttagaaagac gggaaataaa atctgctaag tgatataagc tctaagtagg cgatgtgtga    900
tggagaacac ctttctttta acagtcttca tgttttacag attcgcgaac ttcgaatatc    960
cctatacggt ctgtctaacc ctcgtgtgtc ttttgagtcc aagataaagg ccattattga   1020
gtaacataga catgctggaa tccaaccatt gaagtcacaa ctgtccatgt agattctttg   1080
gagaatctga aaagtcttaa taaggtggt gtttcaaga aaacaaaaca aatgagttaa    1140
gaaaaaaaaa tatcatgtag tggtcgagta ttatgttatt tattgtgtag ctaccaatct   1200
ttattcttta aatctgacat aaaatgctac aaacttttta cctcgtctat agccccaaaa   1260 aacctaaccca cggttctaaa accacacaca gtgattttgg ttgacgacaa tgcctctcct   1320
tcctcaaaac gatttattta catttttaa atcaaatgtt acattttata ccataattaa    1380 gtcttttac agaatactta gatggaagag atgtataaaa aaggaggaaa ttgtaaaaaa   1440
catatttcga tcaattaaac caggattcat aaaaatataa gtatatatat aaatgatgtt   1500
tcgtttagcg atgaacttca ctcatatgat aatacttaac aatataagta cataaaaaat   1560
aaaataaaat taattgttta cgaaaagtct acaaatactg catgtataat taatgttctc   1620
tttatttatt tatttatacc ttaccaagat atatctataa ccgcatagaa atagaaggcg   1680
aagagataat ttccaaaaac aagaaaaacc tctaagctca aaagtctaga aggccttgga   1740
tccacccatg gaggttgtca cagtatcact tgtagcagtt gtgatcacta ctttcttata   1800
cttaatcttc agagattcaa gtcctaaagg tttgccacca ggtccaaaac cctggccaat   1860
agttggaaac cttcttcaac ttggtgagaa acctcattct cagtttgctc agcttgctga   1920
aacctatggt gatctctttt cactgaaact aggaagtgaa acggttgttg tagcttcaac   1980
tccattagca gctagcgaga ttctaaagac gcatgatcgt gttctctctg gtcgatacgt   2040
gtttcaaagt ttccgggtaa aggaacatgt ggagaactct attgtgtggt ctgaatgtaa   2100
tgaaacatgg aagaaactgc ggaaagtttg tagaacggaa cttttacgc agaagatgat    2160 tgaaagtcaa gctgaagtta gagaaagtaa ggctatggaa atggtggagt atttgaagaa   2220
aaatgtagga aatgaagtga aaattgctga agttgtattt gggacgttgg tgaatatatt   2280
cggtaacttg atattttcac aaaatatttt caagttgggt gatgaaagta gtggaagtgt   2340
agaaatgaaa gaacatctat ggagaatgct ggaattgggg aactcgacaa atccagctga   2400
ttattttcca ttttggggta aattcgattt gtttggacaa agaaaagatg ttgctgattg   2460
tctgcaaggg atttatagtg tttggggtgc tatgctcaaa gaaagaaaaa tagccaagca   2520
gcataacaac agcaagaaga atgattttgt tgagattttg ctcgattccg gactcgatga   2580
ccagcagatt aatgccttgc tcatggaaat atttggtgcg ggaacagaga caagtgcatc   2640
tacaatagaa tgggcgttgt ctgagctcac aaaaaaccct caagtaacag ccaatatgcg   2700
gttggaattg ttatctgtgg tagggaagag gccggttaag gaatccgaca taccaaacat   2760
```

```
gccttatctt caagcttttg ttaaagaaac tctacggctt catccagcaa ctcctctgct    2820
gcttccacgt cgagcacttg agacctgcaa agttttgaac tatacgatcc cgaaagagtg    2880
tcagattatg gtgaacgcct ggggcattgg tcgggatcca aaaaggtgga ctgatccatt    2940
gaagttttca ccagagaggt tcttgaattc gagcattgat ttcaaaggga acgacttcga    3000
gttgatacca tttggtgcag ggagaaggat atgtcctggt gtgcccttgg caactcaatt    3060
tattagtctt attgtgtcta gtttggtaca gaattttgat tggggattac cgaagggaat    3120
ggatcctagc caactgatca tggaagagaa atttgggtga cactgcaaaa ggaaccacct    3180
ctgtatattg ttcctaaaac tcgggattaa gggagaattc gtcgactttg cggccgcatc    3240
gatactgcag gagctcggta ccttttacta gtgatatccc tgtgtgaaat tgttatccgc    3300
tacgcgtgat cgttcaaaca tttggcaata agtttctta agattgaatc ctgttgccgg    3360
tcttgcgatg attatcatat aatttctgtt gaattacgtt aagcatgtaa taattaacat    3420
gtaatgcatg acgttattta tgagatgggt ttttatgatt agagtcccgc aattatacat    3480
ttaatacgcg atagaaaaca aaatatagcg cgcaaactag gataaattat cgcgcgcggt    3540
gtcatctatg ttactagatc ccatgggaag ttcctattcc gaagttccta ttctctgaaa    3600
agtataggaa cttcagcgat cgctccaatc ccacaaaaat ctgagcttaa cagcacagtt    3660
gctcctctca gagcagaatc gggtattcaa caccctcata tcaactacta cgttgtgtat    3720
aacggtccac atgccggtat atacgatgac tggggttgta caaggcggc aacaaacggc     3780 gttcccggag ttgcacacaa gaaatttgcc actattacag aggcaagagc agcagctgac    3840
gcgtacacaa caagtcagca acagacagg ttgaacttca tccccaaagg agaagctcaa     3900
ctcaagccca gagctttgc taaggcccta acaagcccac caaagcaaaa agcccactgg     3960
ctcacgctag gaaccaaaag gcccagcagt gatccagccc caaagagac tcctttgccc     4020 cggagattac aatggacgat ttcctctatc tttacgatct aggaaggaag ttcgaaggtg    4080
aaggtgacga cactatgttc accactgata atgagaaggt tagcctcttc aatttcagaa    4140
agaatgctga cccacagatg gttagagagg cctacgcagc aggtctcatc aagacgatct    4200
acccgagtaa caatctccag gagatcaaat accttcccaa gaaggttaaa gatgcagtca    4260
aaagattcag gactaattgc atcaagaaca cagagaaaga catatttctc aagatcagaa    4320
gtactattcc agtatggacg attcaaggct tgcttcataa accaaggcaa gtaatagaga    4380
ttggagtctc taaaaaggta gttcctactg aatctaaggc catgcatgga gtctaagatt    4440
caaatcgagg atctaacaga actcgccgtg aagactggcg aacagttcat acagagtctt    4500
ttacgactca atgacaagaa gaaaatcttc gtcaacatgg tggagcacga cactctggtc    4560
tactccaaaa atgtcaaaga tacagtctca gaagaccaaa gggctattga acttttcaa     4620 caaaggataa tttcgggaaa cctcctcgga ttccattgcc cagctatctg tcacttcatc    4680
gaaaggacag tagaaaagga aggtggctcc tacaaatgcc atcattgcga taaaggaaag    4740
gctatcattc aagatctctc tgccgacagt ggtcccaaag atggacccccc acccacgagg    4800 agcatcgtgg aaaaagaaga cgttccaacc acgtcttcaa agcaagtgga ttgatgtgac    4860
atctccactg acgtaaggga tgacgcacaa tcccactatc cttcgcaaga cccttcctct    4920
atataaggaa gttcatttca tttggagagg acacgctcga gtataagagc tcatttttta    4980
caacaattac caacaacaac aaacaacaaa caacattaca attacattta caattaccat    5040
ggggcgcgcc ccttgtcctc aaccaaatct cgccatcggt cttacgtcgc actcggattt    5100
tggcggtttg acaatcctcc ttcaaatcaa cgaagtggaa ggattacaga taaaaagaga    5160
```

```
ggggacatgg atttcagtca aacctctacc taatgcgttc gtagtgaatg ttggagatat    5220
tttggagata atgactaatg gaatttacca tagtgtcgat caccgggcag tagtaaactc    5280
aacaaatgag aggctctcaa tcgcaacatt tcatgaccct agtctagagt cggtaatagg    5340
cccaatatca agcttgatta ctccagagac acctgctttg tttaaaagtg gaatttaaat    5400
ccccagatga acatggcatc gtggtgattg atgaaactgc tgctgtcggc tttaacctct    5460
ctttaggcat tggtttcgaa gcgggcaaca agccgaaaga actgtacagc gaagaggcag    5520
tcaacgggga aactcagcaa gcgcacttac aggcgattaa agagctgata gcgcgtgaca    5580
aaaaccaccc aagcgtggtg atgtggagta ttgccaacga accggatacc cgtccgcaag    5640
gtgcacggga atatttcgcg ccactggcgg aagcaacgcg taaactcgac ccgacgcgtc    5700
cgatcacctg cgtcaatgta atgttctgcg acgctcacac cgataccatc agcgatctct    5760 tgatgggga tcctccactt ttaaacaaag caggtgtctc tggagtaatc aagcttgata    5820
ttgggcctat taccgactct agactagggt catgaaatgt tgcgattgag agcctctcat    5880
ttgttgagtt tactactgcc cggtgatcga cactatggta aattccatta gtcattatct    5940
ccaaaatatc tccaacattc actacgaacg cattaggtag aggtttgact gaaatccatg    6000
tcccctctct ttttatctgt aatccttcca cttcgttgat ttgaaggagg attgtcaaac    6060
cgccaaaatc cgagtgcgac gtaagaccga tggcgagatt tggttgagga caaggactag    6120
tccctagagt cctgctttaa tgagatatgc gagacgccta tgatcgcatg atatttgctt    6180
tcaattctgt tgtgcacgtt gtaaaaaacc tgagcatgtg tagctcagat ccttaccgcc    6240
ggtttcggtt cattcaatg aatgaatata tcacccgtta ctatcgtatt tttatgaata    6300
atattctccg ttcaatttac tgattgtacc ctactactta tatgtacaat attaaaatga    6360
aaacaatata ttgtgctgaa taggtttata gcgacatcta tgatagagcg ccacaataac    6420
aaacaattgc gttttattat tacaaatcca attttaaaaa aagcggcaga accggtcaaa    6480
cctaaaagac tgattacata aatcttattc aaatttcaaa agtgccccag ggctagtat    6540 ctacgacaca ccgagcggcg aactaataac gctcactgaa gggaactccg gttccccgcc    6600
ggcgcgcatg ggtgagattc cttgaagttg agtattggcc gtccgctcta ccgaaagtta    6660
cgggcaccat tcaacccggt ccagcacggc ggccgggtaa ccgacttgct gccccgagaa    6720
ttatgcagca ttttttttggt gtatgtgggc cccaaatgaa gtgcaggtca aaccttgaca    6780
gtgacgacaa atcgttgggc gggtccaggg cgaattttgc gacaacatgt cgaggctcag    6840
cagggcgatc gcagacgtcg ggatcttctg caagcatctc tatttcctga aggtctaacc    6900
tcgaagattt aagatttaat tacgtttata attacaaaat tgattctagt atctttaatt    6960
taatgcttat acattattaa ttaatttagt actttcaatt tgttttcaga aattatttta    7020 ctattttta taaaataaaa gggagaaaat ggctatttaa atactagcct attttatttc    7080
aattttagct taaaatcagc cccaattagc cccaatttca aattcaaatg gtccagccca    7140
attcctaaat aacccacccc taacccgccc ggtttcccct tttgatccat gcagtcaacg    7200
cccagaattt ccctatataa tttttttaatt cccaaacacc cctaactcta tcccatttct    7260
caccaaccgc cacatagatc tatcctctta tctctcaaac tctctcgaac cttcccctaa    7320
ccctagcagc ctctcatcat cctcacctca aaacccaccg gggccggcca tgattgaaca    7380
agatggattg cacgcaggtt ctccggccgc ttgggtggag aggctattcg gctatgactg    7440
ggcacaacag acaatcggct gctctgatgc cgccgtgttc cggctgtcag cgcagggag    7500 gccggttctt tttgtcaaga ccgacctgtc cggtgccctg aatgaacttc aagacgaggc    7560
```

| | |
|---|---|
| agcgcggcta tcgtggctgg ccacgacggg cgttccttgc gcagctgtgc tcgacgttgt | 7620 |
| cactgaagcg ggaagggact ggctgctatt gggcgaagtg ccggggcagg atctcctgtc | 7680 |
| atctcacctt gctcctgccg agaaagtatc catcatggct gatgcaatgc ggcggctgca | 7740 |
| tacgcttgat ccggctacct gcccattcga ccaccaagcg aaacatcgca tcgagcgagc | 7800 |
| acgtactcgg atggaagccg gtcttgtcga tcaggatgat ctggacgaag agcatcaggg | 7860 |
| gctcgcgcca gccgaactgt tcgccaggct caaggcgcgc atgcccgacg gcgaggatct | 7920 |
| cgtcgtgact catggcgatg cctgcttgcc gaatatcatg gtggaaaatg gccgcttttc | 7980 |
| tggattcatc gactgtggcc ggctgggtgt ggcggaccgc tatcaggaca tagcgttggc | 8040 |
| tacccgtgat attgctgaag agcttggcgg cgaatgggct gaccgcttcc tcgtgcttta | 8100 |
| cggtatcgcc gctcccgatt cgcagcgcat cgccttctat cgccttcttg acgagttctt | 8160 |
| ctgaggcgcg ccgatcgttc aaacatttgg caataaagtt tcttaagatt gaatcctgtt | 8220 |
| gccggtcttg cgatgattat catataattt ctgttgaatt acgttaagca tgtaataatt | 8280 |
| aacatgtaat gcatgacgtt atttatgaga tgggttttta tgattagagt cccgcaatta | 8340 |
| tacatttaat acgcgataga aaacaaaata tagcgcgcaa actaggataa attatcgcgc | 8400 |
| gcggtgtcat ctatgttact agatccctag gaagttcct attccgaagt tcctattctc | 8460 |
| tgaaaagtat aggaacttct ttgcgtattg ggcgctcttg ccttttttgg ccaccggtcg | 8520 |
| tacggttaaa accaccccag tacattaaaa acgtccgcaa tgtgttatta agttgtctaa | 8580 |
| gcgtcaattt gtttacacca caatatatcc tgccaccagc cagccaacag ctccccgacc | 8640 |
| ggcagctcgg cacaaaatca ccactcgata caggcagccc atcagtcc | 8688 |

<210> SEQ ID NO 6
<211> LENGTH: 3238
<212> TYPE: DNA
<213> ORGANISM: Artificial Sequence
<220> FEATURE:
<223> OTHER INFORMATION: expression cassette including promoter

<400> SEQUENCE: 6

| | |
|---|---|
| gcgatcgctc caatcccaca aaaatctgag cttaacagca cagttgctcc tctcagagca | 60 |
| gaatcgggta ttcaacaccc tcatatcaac tactacgttg tgtataacgg tccacatgcc | 120 |
| ggtatatacg atgactgggg ttgtacaaag gcggcaacaa acggcgttcc cggagttgca | 180 |
| cacaagaaat ttgccactat tacagaggca agagcagcag ctgacgcgta cacaacaagt | 240 |
| cagcaaacag acaggttgaa cttcatcccc aaaggagaag ctcaactcaa gcccaagagc | 300 |
| tttgctaagg ccctaacaag cccaccaaag caaaaagccc actggctcac gctaggaacc | 360 |
| aaaaggccca gcagtgatcc agccccaaaa gagactcctt gcccccggag attacaatgg | 420 |
| acgatttcct ctatctttac gatctaggaa ggaagttcga aggtgaaggt gacgacacta | 480 |
| tgttcaccac tgataatgag aaggttagcc tcttcaattt cagaaagaat gctgacccac | 540 |
| agatggttag agaggcctac gcagcaggtc tcatcaagac gatctacccg agtaacaatc | 600 |
| tccaggagat caaataccct tccaagaagg ttaaagatgc agtcaaaaga ttcaggacta | 660 |
| attgcatcaa gaacacagag aaagacatat ttctcaagat cagaagtact attccagtat | 720 |
| ggacgattca aggcttgctt cataaaccaa ggcaagtaat agagattgga gtctctaaaa | 780 |
| aggtagttcc tactgaatct aaggccatgc atggagtcta agattcaaat cgaggatcta | 840 |
| acagaactcg ccgtgaagac tggcgaacag ttcatacaga gtcttttacg actcaatgac | 900 |

```
aagaagaaaa tcttcgtcaa catggtggag cacgacactc tggtctactc caaaaatgtc    960
aaagatacag tctcagaaga ccaaagggct attgagactt ttcaacaaag gataatttcg   1020
ggaaacctcc tcggattcca ttgcccagct atctgtcact tcatcgaaag gacagtagaa   1080
aaggaaggtg gctcctacaa atgccatcat tgcgataaag gaaaggctat cattcaagat   1140
ctctctgccg acagtggtcc caaagatgga cccccaccca cgaggagcat cgtggaaaaa   1200
gaagacgttc caaccacgtc ttcaaagcaa gtggattgat gtgacatctc cactgacgta   1260
agggatgacg cacaatccca ctatccttcg caagacccct cctctatata aggaagttca   1320
tttcatttgg agaggacacg ctcgagtata gagctctat ttttacaaca attaccaaca    1380
acaacaaaca acaaacaaca ttacaattac atttacaatt accatggggc gcgccccttg   1440
tcctcaacca aatctcgcca tcggtcttac gtcgcactcg gattttggcg gtttgacaat   1500
cctccttcaa atcaacgaag tggaaggatt acagataaaa agagagggga catggatttc   1560
agtcaaacct ctacctaatg cgttcgtagt gaatgttgga gatatttgg agataatgac    1620
taatggaatt taccatagtg tcgatcaccg ggcagtagta aactcaacaa atgagaggct   1680
ctcaatcgca acatttcatg accctagtct agagtcggta ataggcccaa tatcaagctt   1740
gattactcca gagacacctg ctttgtttaa aagtggaatt taaatcccca gatgaacatg   1800
gcatcgtggt gattgatgaa actgctgctg tcggctttaa cctctcttta ggcattggtt   1860
tcgaagcggg caacaagccg aaagaactgt acagcgaaga ggcagtcaac ggggaaactc   1920
agcaagcgca cttacaggcg attaaagagc tgatagcgcg tgacaaaaac cacccaagcg   1980
tggtgatgtg gagtattgcc aacgaaccgg atacccgtcc gcaaggtgca cgggaatatt   2040
tcgcgccact ggcggaagca acgcgtaaac tcgacccgac gcgtccgatc acctgcgtca   2100
atgtaatgtt ctgcgacgct cacaccgata ccatcagcga tctctttgat ggggatcctc   2160
cacttttaaa caaagcaggt gtctctggag taatcaagct tgatattggg cctattaccg   2220
actctagact agggtcatga aatgttgcga ttgagagcct ctcatttgtt gagtttacta   2280
ctgcccggtg atcgacacta tggtaaattc cattagtcat tatctccaaa atatctccaa   2340
cattcactac gaacgcatta ggtagaggtt tgactgaaat ccatgtcccc tctcttttta   2400
tctgtaatcc ttccacttcg ttgatttgaa ggaggattgt caaaccgcca aaatccgagt   2460
gcgacgtaag accgatggcg agatttggtt gaggacaagg actagtccct agagtcctgc   2520
tttaatgaga tatgcgagac gcctatgatc gcatgatatt tgctttcaat tctgttgtgc   2580
acgttgtaaa aaacctgagc atgtgtagct cagatcctta ccgccggttt cggttcattc   2640
taatgaatga atatatcacc cgttactatc gtattttat gaataatatt ctccgttcaa    2700
tttactgatt gtaccctact acttatatgt acaatattaa aatgaaaaca atatattgtg   2760
ctgaataggt ttatagcgac atctatgata gagcgccaca ataacaaaca attgcgtttt   2820
attattacaa atccaatttt aaaaaaagcg gcagaaccgg tcaaacctaa aagactgatt   2880
acataaatct tattcaaatt tcaaagtgc cccaggggct agtatctacg acacaccgag    2940
cggcgaacta ataacgctca ctgaagggaa ctccggttcc ccgccggcgc gcatgggtga   3000
gattccttga agttgagtat tggccgtccg ctctaccgaa agttacgggc accattcaac   3060
ccggtccagc acggcggccg ggtaaccgac ttgctgcccc gagaattatg cagcattttt   3120
ttggtgtatg tgggccccaa atgaagtgca ggtcaaacct tgacagtgac gacaaatcgt   3180
tgggcgggtc cagggcgaat tttgcgacaa catgtcgagg ctcagcaggg cgatcgca     3238
```

```
<210> SEQ ID NO 7
<211> LENGTH: 1067
<212> TYPE: DNA
<213> ORGANISM: Artificial Sequence
<220> FEATURE:
<223> OTHER INFORMATION: hairpin construct

<400> SEQUENCE: 7
ccccttgtcc tcaaccaaat ctcgccatcg gtcttacgtc gcactcggat tttggcggtt      60
tgacaatcct ccttcaaatc aacgaagtgg aaggattaca gataaaaaga gagggggacat    120 ggatttcagt caaacctcta cctaatgcgt tcgtagtgaa tgttggagat attttggaga    180
taatgactaa tggaatttac catagtgtcg atcaccgggc agtagtaaac tcaacaaatg    240
agaggctctc aatcgcaaca tttcatgacc ctagtctaga gtcggtaata ggcccaatat    300
caagcttgat tactccagag acacctgctt tgtttaaaag tggaatttaa atccccagat    360
gaacatggca tcgtggtgat tgatgaaact gctgctgtcg gctttaacct ctctttaggc    420
attggtttcg aagcgggcaa caagccgaaa gaactgtaca gcgaagaggc agtcaacggg    480
gaaactcagc aagcgcactt acaggcgatt aaagagctga tagcgcgtga caaaaaccac    540
ccaagcgtgg tgatgtggag tattgccaac gaaccggata cccgtccgca aggtgcacgg    600
gaatatttcg cgccactggc ggaagcaacg cgtaaactcg acccgacgcg tccgatcacc    660
tgcgtcaatg taatgttctg cgacgctcac accgatacca tcagcgatct ctttgatggg    720
gatcctccac ttttaaacaa agcaggtgtc tctggagtaa tcaagcttga tattgggcct    780
attaccgact ctagactagg gtcatgaaat gttgcgattg agagcctctc atttgttgag    840
tttactactg cccggtgatc gacactatgg taaattccat tagtcattat ctccaaaata    900
tctccaacat tcactacgaa cgcattaggt agaggtttga ctgaaatcca tgtcccctct    960
ctttttatct gtaatccttc cacttcgttg atttgaagga ggattgtcaa accgccaaaa   1020
tccgagtgcg acgtaagacc gatggcgaga tttggttgag gacaagg                  1067

<210> SEQ ID NO 8
<211> LENGTH: 342
<212> TYPE: DNA
<213> ORGANISM: Artificial Sequence
<220> FEATURE:
<223> OTHER INFORMATION: sense strand of hairpin construct

<400> SEQUENCE: 8
ccttgtcctc aaccaaatct cgccatcggt cttacgtcgc actcggattt tggcggtttg      60
acaatcctcc ttcaaatcaa cgaagtggaa ggattacaga taaaagaga ggggacatgg     120 atttcagtca aacctctacc taatgcgttc gtagtgaatg ttggagatat tttggagata    180
atgactaatg gaatttacca tagtgtcgat caccgggcag tagtaaactc aacaaatgag    240
aggctctcaa tcgcaacatt tcatgaccct agtctagagt cggtaatagg cccaatatca    300
agcttgatta ctccagagac acctgctttg tttaaaagtg ga                       342

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
taaccgactt gctgccccga                                                  20
```

```
<210> SEQ ID NO 10
<211> LENGTH: 27
<212> TYPE: DNA
<213> ORGANISM: Artificial Sequence
<220> FEATURE:
<223> OTHER INFORMATION: Synthetic primer

<400> SEQUENCE: 10
aaatagagat gcttgcagaa gatcccg                                          27

<210> SEQ ID NO 11
<211> LENGTH: 24
<212> TYPE: DNA
<213> ORGANISM: Artificial Sequence
<220> FEATURE:
<223> OTHER INFORMATION: Synthetic primer

<400> SEQUENCE: 11
cgtttgaatc ttgctggccg tgat                                             24

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
tagacgagct gcctttggaa gtgt                                             24

<210> SEQ ID NO 13
<211> LENGTH: 21
<212> TYPE: DNA
<213> ORGANISM: Artificial Sequence
<220> FEATURE:
<223> OTHER INFORMATION: Synthetic primer

<400> SEQUENCE: 13
cgtcttgcgc actgatttga a                                                21

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
cgtttgaatc ttgctggccg tgat                                             24

<210> SEQ ID NO 15
<211> LENGTH: 1386
<212> TYPE: DNA
<213> ORGANISM: Artificial Sequence
<220> FEATURE:
<223> OTHER INFORMATION: T6ODM RNA transcript

<400> SEQUENCE: 15
guucuuaauu cauuaauuaa uuuagaaaaa ucauggagaa agcaaaacuu augaagcuag      60
guaaugguau ggaaauacca aguguucaag aauuggcuaa acucacgcuu gccgaaauuc     120
caucucgaua cguaugcgcc aaugaaaacc uuuuguugcc uaugggugca ucugucauaa     180
augaucauga aaccauuccu gucaucgaua uagaaaauuu auuaucucca gaaccaauaa     240
ucggaaaguu agaauuagau aggcuucauu uugcuugcaa agaaugggguu uuuuucagg    300
```

| | |
|---|---|
| uagugaacca uggagucgac gcuucauugg uggauagugu aaaaucagaa auucaagguu | 360 |
| ucuuuaaccu uucuauggau gagaaaacua aauaugaaca ggaagaugga gauguggaag | 420 |
| gauuuggaca aggcuuuauu gaaucagagg accaaacacu ugauugggca gauauauuua | 480 |
| ugauguucac ucuuccacuc cauuuaagga agccucacuu auuuucaaaa cucccagugc | 540 |
| cucucaggga gacaaucgaa uccuacucau cagaaaugaa aaaguuaucc augguucucu | 600 |
| uuaauaagau ggaaaaagcu cuacaaguac aagcagccga gauuaagggu augucagagg | 660 |
| uguuuauaga ugggacacaa gcaaugagga ugaacuauua uccccuugu ccucaaccaa | 720 |
| aucucgccau cggucuuacg ucgcacucgg auuuuggcgg uuugacaauc uccuucaaa | 780 |
| ucaacgaagu ggaaggauua cagauaaaaa gagaggggac auggauuuca gucaaaccuc | 840 |
| uaccuaaugc guucguagug aauguuggag auauuuugga gauaaugacu aauggaauuu | 900 |
| accauagugu cgaucaccgg gcaguaguaa acucaacaaa ugagaggcuc ucaaucgcaa | 960 |
| cauuucauga cccuagucua gagucgguaa uaggcccaau aucaagcuug auuacuccag | 1020 |
| agacaccugc uuuguuuaaa aguggaucua cauuggggga ucuuguggag gaauguaaaa | 1080 |
| caaggaagcu cgauggaaaa ucauuucuug acuccaugag gauuugaaaa cucaagaaaa | 1140 |
| aauaauacga cgugauugca ugucagauuc aacuauccuu uugucguuuu uuggugcucg | 1200 |
| aguccuuaau uguuugauc auugcuuuug auucuaauua auaagacuuu ucucaagaac | 1260 |
| cacauguauu guaccuuuac uuucagaaaa uaaaaaguau ugaggcacaa augagaaaau | 1320 |
| ugagagagug cuugagaagu guaauuucuc gaaagugcgu uguguuugaa aaaaaaaaa | 1380 |
| aaaaaa | 1386 |

<210> SEQ ID NO 16
<211> LENGTH: 1452
<212> TYPE: RNA
<213> ORGANISM: Artificial Sequence
<220> FEATURE:
<223> OTHER INFORMATION: CODM RNA transcript

<400> SEQUENCE: 16

| | |
|---|---|
| guaaagauug auauaugauc ugaagaucug acaagaaagu caucaaaaua uagaguucau | 60 |
| ggagacacca auacuuauca agcuaggcaa ugguuuguca auaccaagug uucaggaauu | 120 |
| ggcuaaacuc acgcuugcag aaauuccauc ucgauacaca ugcaccggug aaagcccguu | 180 |
| gaauaauauu ggugcgucug uaacagauga ugaaacaguu ccugucaucg auuugcaaaa | 240 |
| uuuacuaucu ccagaacccg uaguggaaa guuagaauug auaagcuuc auucugcuug | 300 |
| caaagaaugg gguucuuuc agcugguuaa ccauggaguc gacgcuuuac ugauggacaa | 360 |
| uauaaaauca gaaauuaaag guucuuuaa ccuuccaaug aaugagaaaa cuaaaaucgg | 420 |
| acagcaagau ggagauuuug aaggauuugg acaacccuau auugaaucgg aggaccaaag | 480 |
| acuugauugg acugaagugu uuagcauguu aagcuuccu cuccauuuaa ggaagccuca | 540 |
| uuuguuucca gaacucccuc ugccuuucag ggagacacug gaauccuacc uaucaaaaau | 600 |
| gaaaaaacua ucaacgguug ucuuugagau guuggaaaaa ucucuacaau uaguugagau | 660 |
| uaaagguaug acagacuuau uugaagaugg guugcaaaca augaggauga acuauuaucc | 720 |
| uccuugaccu cgaccagagc uuguacuugg ucuuacguca cacucggauu uuagcgguuu | 780 |
| gacaauucuc cuucaacuua augaaguuga aggauuacaa auaagaaaag aagagaggug | 840 |
| gauuucaauc aaaccucuac cugaugcguu cauagugaau guuggagaca uuuuggagau | 900 |
| aaugacuaau gggauuuacc guagcgucga gcaccgggca guauaaacu caacaaagga | 960 |

```
gaggcucuca aucgcgacau uucaugacuc uaaacuagag ucagaaauag gcccaauuuc   1020
gagcuugguc acaccagaga caccugcuuu guucaaaaga gguagguaug aggauauuuu   1080
gaaggaaaau cuuucaagga agcuugaugg aaaaucauuu cucgacuaca ugaggaugug   1140
agaaagugug aacauauauu auacuccaca uuguguuuaa uauaugauga aauaaguugc   1200
uuuugaagua ugaugaaaua aguuggguuu gaagaauuca uauugugcuu aaauuucgug   1260
gaugacugag agauuuauua uguaauaaua auguauuggu uugaagauuc ucgucucacu   1320
auauguaaga cucuguuugg gucaagugau guaaucacgg uugaaauaag uugcuuuuga   1380
agaauucaua uggugcuuaa uauuauguaa uaaauaaugu auuggauuga aaaaaaaaaa   1440
aaaaaaaaaa aa                                                      1452
```